United States Patent
Pei

(10) Patent No.: US 12,281,181 B2
(45) Date of Patent: *Apr. 22, 2025

(54) BICYCLIC PEPTIDYL INHIBITORS

(71) Applicant: Ohio State Innovation Foundation, Columbus, OH (US)

(72) Inventor: Dehua Pei, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/333,516

(22) Filed: Jun. 12, 2023

(65) Prior Publication Data

US 2023/0322859 A1  Oct. 12, 2023

Related U.S. Application Data

(60) Continuation of application No. 17/750,966, filed on May 23, 2022, now Pat. No. 11,673,919, which is a division of application No. 16/753,681, filed as application No. PCT/US2018/054345 on Oct. 4, 2018, now Pat. No. 11,339,192.

(60) Provisional application No. 62/568,221, filed on Oct. 4, 2017.

(51) Int. Cl.
*C07K 7/64* (2006.01)
*A61P 35/00* (2006.01)

(52) U.S. Cl.
CPC ............... *C07K 7/64* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 5,523,308 A | 6/1996 | Costanzo et al. |
| 5,579,250 A | 11/1996 | Balaji et al. |
| 5,595,756 A | 1/1997 | Bally |
| 5,612,895 A | 3/1997 | Balaji et al. |
| 5,631,280 A | 5/1997 | Ciccarone et al. |
| 5,804,558 A | 9/1998 | Lehrer et al. |
| 5,965,536 A | 10/1999 | Cohen et al. |
| 6,110,889 A | 8/2000 | Miller et al. |
| 6,251,854 B1 | 6/2001 | Montal et al. |
| 6,355,619 B1 | 3/2002 | Miller et al. |
| 6,583,107 B2 | 6/2003 | Laby et al. |
| 6,593,292 B1 | 7/2003 | Rothbard et al. |
| 6,605,115 B1 | 8/2003 | Cooke et al. |
| 6,649,587 B1 | 11/2003 | Frydman et al. |
| 6,669,951 B2 | 12/2003 | Rothbard et al. |
| 6,730,293 B1 | 5/2004 | Rothbard et al. |
| 6,759,387 B2 | 7/2004 | Rothbard et al. |
| 6,794,545 B1 | 9/2004 | Frydman et al. |
| 6,809,176 B2 | 10/2004 | Blokhin et al. |
| 6,864,355 B1 | 3/2005 | May et al. |
| 6,960,648 B2 | 11/2005 | Bonny |
| 6,982,351 B2 | 1/2006 | Frydman et al. |
| 7,026,347 B2 | 4/2006 | Frydman et al. |
| 7,084,241 B2 | 8/2006 | Hogan et al. |
| 7,169,814 B2 | 1/2007 | Rothbard et al. |
| 7,186,825 B2 | 3/2007 | Frydman et al. |
| 7,229,961 B2 | 6/2007 | Rothbard et al. |
| 7,253,207 B2 | 8/2007 | Blokhin et al. |
| 7,279,502 B2 | 10/2007 | Frydman et al. |
| 7,312,244 B2 | 12/2007 | Frydman et al. |
| 7,495,103 B2 | 2/2009 | Hadida-Ruah et al. |
| 7,585,834 B2 | 9/2009 | Wender et al. |
| 7,816,490 B2 | 10/2010 | Hogan et al. |
| 7,850,949 B2 | 12/2010 | Fang |
| 7,862,807 B2 | 1/2011 | Goodman et al. |
| 8,507,534 B2 | 8/2013 | Keshavarz-Shokri et al. |
| 8,614,290 B2 | 12/2013 | Wester et al. |
| 8,623,833 B2 | 1/2014 | Rothbard et al. |
| 8,628,750 B2 | 1/2014 | Wester et al. |
| 8,629,112 B2 | 1/2014 | Gombert et al. |
| 8,754,224 B2 | 6/2014 | Hurter et al. |
| 8,883,718 B2 | 11/2014 | Warenius |
| 8,901,071 B2 | 12/2014 | O'Neil et al. |

(Continued)

FOREIGN PATENT DOCUMENTS

| | | |
|---|---|---|
| CA | 2455951 | 2/2003 |
| CA | 2417064 | 2/2022 |

(Continued)

OTHER PUBLICATIONS

International Search Report and Written Opinion issued by the International Searching Authority (ISA/US) in PCT Application No. PCT/US2018/054345 on Mar. 4, 2019. 14 pages.

(Continued)

*Primary Examiner* — Thomas S Heard

(74) *Attorney, Agent, or Firm* — Meunier Carlin & Curfman LLC

(57) ABSTRACT

The present disclosure provides a large combinatorial library of cell-permeable bicyclic peptides. The bicyclic peptides described herein include the first ring consisted of randomized peptide sequences for potential binding to a target of interest while the second ring featured a family of different cell-penetrating motifs, for both cell penetration and target binding. The library was screened against the IκB kinase α/β (IKKα/β)-binding domain of NF-κB essential modulator (NEMO), resulting in the discovery of several cell-permeable bicyclic peptides which inhibited the NEMO-IKKβ interaction, thereby selectively inhibiting canonical NF-κB signaling in mammalian cells and the proliferation of cisplatin-resistant ovarian cancer cells.

9 Claims, 5 Drawing Sheets

Figure 1:
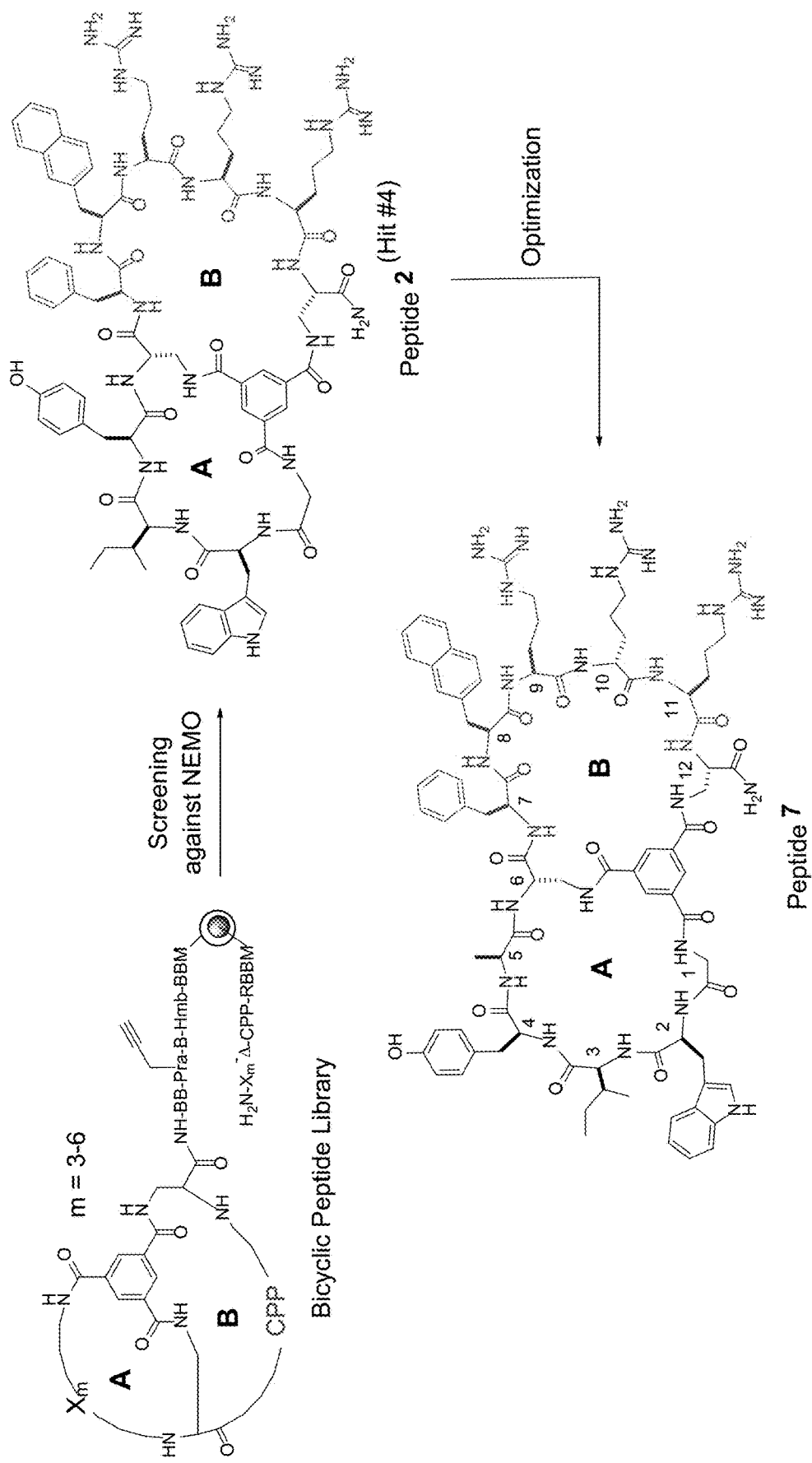

Specification includes a Sequence Listing.

(56) References Cited

U.S. PATENT DOCUMENTS

| | | |
|---|---|---|
| 8,999,919 B2 | 4/2015 | Madden et al. |
| 9,139,530 B2 | 9/2015 | Hurter et al. |
| 9,169,290 B2 | 10/2015 | O'Neil |
| 9,216,969 B2 | 12/2015 | Ruah et al. |
| 9,303,075 B2 | 4/2016 | Brinkmann et al. |
| 9,868,767 B2 | 1/2018 | Pei et al. |
| 10,501,496 B2 | 12/2019 | Pei et al. |
| 10,626,147 B2 | 4/2020 | Pei et al. |
| 10,738,093 B2 | 8/2020 | Qian et al. |
| 10,815,276 B2 | 10/2020 | Pei et al. |
| 10,913,773 B2 | 2/2021 | Pei |
| 11,225,506 B2 | 1/2022 | Pei et al. |
| 11,339,192 B2 | 5/2022 | Pei |
| 11,351,222 B2 | 6/2022 | Pei et al. |
| 11,352,394 B2 | 6/2022 | Pei et al. |
| 11,576,946 B2 | 2/2023 | Pei et al. |
| 2002/0009491 A1 | 1/2002 | Rothbard et al. |
| 2002/0035243 A1 | 3/2002 | Imfeld et al. |
| 2002/0120100 A1 | 8/2002 | Bonny |
| 2002/0127198 A1 | 9/2002 | Rothbard et al. |
| 2003/0022831 A1 | 1/2003 | Rothbard et al. |
| 2003/0032593 A1 | 2/2003 | Wender et al. |
| 2003/0032594 A1 | 2/2003 | Bonny |
| 2003/0072715 A1 | 4/2003 | Frydman et al. |
| 2003/0130356 A1 | 7/2003 | Frydman et al. |
| 2003/0138932 A1 | 7/2003 | Moller et al. |
| 2003/0167129 A1 | 9/2003 | Nestor, Jr. et al. |
| 2003/0194745 A1 | 10/2003 | McDowell et al. |
| 2004/0002117 A1 | 1/2004 | Hogan et al. |
| 2004/0014669 A1 | 1/2004 | Selsted et al. |
| 2004/0152687 A1 | 8/2004 | Frydman et al. |
| 2004/0192665 A1 | 9/2004 | Frydman et al. |
| 2004/0248783 A1 | 12/2004 | Kawabe et al. |
| 2005/0107289 A1 | 5/2005 | Ghadiri et al. |
| 2005/0192210 A1 | 9/2005 | Rothbard et al. |
| 2006/0128614 A1 | 6/2006 | Cheng et al. |
| 2006/0141514 A1 | 6/2006 | Rozzelle et al. |
| 2007/0041904 A1 | 2/2007 | Jiang et al. |
| 2007/0093427 A1 | 4/2007 | Matsui et al. |
| 2008/0234183 A1 | 9/2008 | Hallbrink et al. |
| 2009/0111799 A1 | 4/2009 | Chen et al. |
| 2009/0186802 A1 | 7/2009 | Alluis et al. |
| 2010/0221235 A1 | 9/2010 | Arranz |
| 2010/0292148 A1 | 11/2010 | Krippner et al. |
| 2012/0016005 A1 | 1/2012 | Samarsky et al. |
| 2012/0045393 A1 | 2/2012 | Linder et al. |
| 2012/0071504 A1 | 3/2012 | Yang et al. |
| 2013/0085736 A1 | 4/2013 | Reihsen et al. |
| 2014/0294942 A1 | 10/2014 | French et al. |
| 2014/0303071 A1 | 10/2014 | O'Neil |
| 2014/0342992 A1 | 11/2014 | Gait et al. |
| 2015/0038671 A1 | 2/2015 | Parang et al. |
| 2015/0284437 A1 | 10/2015 | Verdine et al. |
| 2015/0284455 A1 | 10/2015 | Springer et al. |
| 2015/0297742 A1 | 10/2015 | Strieker et al. |
| 2016/0031941 A1 | 2/2016 | Eckert et al. |
| 2016/0115202 A1 | 4/2016 | Pei et al. |
| 2016/0151512 A1 | 6/2016 | Kim |
| 2016/0235807 A1 | 8/2016 | Shailubhai |
| 2016/0271216 A1 | 9/2016 | Kemper et al. |
| 2016/0317679 A1 | 11/2016 | Baumhof et al. |
| 2017/0112896 A1 | 4/2017 | Briesewitz |
| 2017/0190743 A1 | 7/2017 | Pei et al. |
| 2017/0281723 A1 | 10/2017 | Pei et al. |
| 2017/0304383 A1 | 10/2017 | Brieswewitz et al. |
| 2017/0355730 A1 | 12/2017 | Pei et al. |
| 2018/0030094 A1 | 2/2018 | Pei et al. |
| 2019/0216752 A1 | 7/2019 | Im et al. |
| 2019/0282654 A1 | 9/2019 | Pei et al. |
| 2019/0284239 A1 | 9/2019 | Pei et al. |
| 2019/0284240 A1 | 9/2019 | Pei et al. |
| 2019/0309020 A1 | 10/2019 | Pei et al. |
| 2020/0276323 A1 | 9/2020 | Pei |
| 2020/0291070 A1 | 9/2020 | Pei et al. |
| 2020/0353092 A1 | 11/2020 | Foster et al. |
| 2020/0354697 A1 | 11/2020 | Sethuraman et al. |
| 2021/0038737 A1 | 2/2021 | Pei et al. |
| 2021/0070806 A1 | 3/2021 | Pei |
| 2021/0115088 A1 | 4/2021 | Pei |
| 2021/0169966 A1 | 6/2021 | Pei et al. |
| 2021/0244824 A1 | 8/2021 | Pei et al. |
| 2021/0261500 A1 | 8/2021 | Pei et al. |
| 2022/0160819 A1 | 5/2022 | Pei et al. |
| 2022/0281920 A1 | 9/2022 | Pei |
| 2022/0306693 A1 | 9/2022 | Pei et al. |
| 2022/0315631 A1 | 10/2022 | Pei |
| 2023/0106131 A1 | 4/2023 | Pei |
| 2023/0212235 A1 | 7/2023 | Pei |

FOREIGN PATENT DOCUMENTS

| | | |
|---|---|---|
| CN | 105440105 | 3/2016 |
| EP | 1185493 | 7/2005 |
| EP | 1574507 | 9/2005 |
| EP | 1797901 | 6/2007 |
| EP | 2420255 | 2/2012 |
| JP | 3791981 | 6/2006 |
| JP | 2010526091 | 7/2010 |
| JP | 2016065018 | 4/2016 |
| WO | 1999021877 | 5/1999 |
| WO | 2000011022 | 3/2000 |
| WO | 2001013957 | 3/2001 |
| WO | 01052875 | 7/2001 |
| WO | 0231109 | 4/2002 |
| WO | 2002057313 | 7/2002 |
| WO | 2002064091 | 8/2002 |
| WO | 2002067917 | 9/2002 |
| WO | 2002090503 | 11/2002 |
| WO | 2003059942 | 7/2003 |
| WO | 03/070755 | 8/2003 |
| WO | 2003092631 | 11/2003 |
| WO | 2003092632 | 11/2003 |
| WO | 2004050685 | 6/2004 |
| WO | 2006041805 | 4/2006 |
| WO | 2006058436 | 6/2006 |
| WO | 2006086773 | 8/2006 |
| WO | 2007040535 | 4/2007 |
| WO | 2007055578 | 5/2007 |
| WO | 2007070372 | 6/2007 |
| WO | 2007071396 | 6/2007 |
| WO | 2007072037 | 6/2007 |
| WO | 2007096662 | 8/2007 |
| WO | 2007106554 | 9/2007 |
| WO | 2007108749 | 9/2007 |
| WO | 2007111993 | 10/2007 |
| WO | 2008077194 | 7/2008 |
| WO | 2008134761 | 11/2008 |
| WO | 2009027706 | 3/2009 |
| WO | 2009092062 | 7/2009 |
| WO | 2009098450 | 8/2009 |
| WO | 2010039088 | 4/2010 |
| WO | 2010045335 | 4/2010 |
| WO | 2010072406 | 7/2010 |
| WO | 2010107832 | 9/2010 |
| WO | 2011095218 | 8/2011 |
| WO | 2011095607 | 8/2011 |
| WO | 2013123266 | 8/2013 |
| WO | 2013142184 | 9/2013 |
| WO | 2013150338 | 10/2013 |
| WO | 2014053629 | 4/2014 |
| WO | 2014053882 | 4/2014 |
| WO | 2014086835 | 6/2014 |
| WO | 2014190257 | 11/2014 |
| WO | 2014190313 | 11/2014 |
| WO | 2015051030 | 4/2015 |
| WO | 2015148620 | 10/2015 |
| WO | 2015153761 | 10/2015 |
| WO | 2015179434 | 11/2015 |
| WO | 2015179691 | 11/2015 |
| WO | 2016033368 | 3/2016 |
| WO | 2016044683 | 3/2016 |
| WO | 2016054510 | 4/2016 |
| WO | 2016177898 | 11/2016 |
| WO | 2017083637 | 5/2017 |

(56) References Cited

FOREIGN PATENT DOCUMENTS

| | | |
|---|---|---|
| WO | 2017/109076 | 6/2017 |
| WO | 2017114440 | 7/2017 |
| WO | 2017/147283 | 8/2017 |
| WO | 2018056530 | 3/2018 |
| WO | 2018/098231 | 5/2018 |
| WO | 2018089648 | 5/2018 |
| WO | 2018098226 | 5/2018 |
| WO | 2018098282 | 5/2018 |
| WO | 2019018898 | 1/2019 |
| WO | 2019051327 | 3/2019 |
| WO | 2019070962 | 4/2019 |
| WO | 2019084528 | 5/2019 |
| WO | 2019148194 | 8/2019 |
| WO | 2019148195 | 8/2019 |
| WO | 2019/217682 | 11/2019 |
| WO | 2019213662 | 11/2019 |
| WO | 2020010103 | 1/2020 |
| WO | 2021041895 | 3/2021 |
| WO | 2021138397 | 7/2021 |
| WO | 2022178379 | 8/2022 |
| WO | 2022271810 | 12/2022 |

OTHER PUBLICATIONS

International Preliminary Report on Patentability issued for Application No. Application No. PCT/US2018/054345, date Apr. 16, 2020.

Alonso, Andres, et al. "Protein tyrosine phosphatases in the human genome." Cell 117.6 (2004): 699-711.

Baud, Véronique, and Michael Karin. "Is NF-κB a good target for cancer therapy? Hopes and pitfalls." Nature reviews Drug discovery 8.1 (2009): 33-40.

Bedewy, Walaa, et al. "Generation of a cell-permeable cycloheptapeptidyl inhibitor against the peptidyl-prolyl isomerase Pin1." Organic & biomolecular chemistry 15.21 (2017): 4540-4543.

Bruno PA, et al., "A synthetic loop replacement peptide blocks canonical NF-κB signaling", Angew. Chem. Int. Ed. 2016, 55, 14997-15001.

Cardote, Teresa AF, and Alessio Ciulli. "Cyclic and macrocyclic peptides as chemical tools to recognise protein surfaces and probe protein-protein interactions." ChemMedChem 11.8 (2016): 787-794.

Chen, Ying, et al. "Inhibition of the nuclear export receptor XPO1 as a therapeutic target for platinum-resistant ovarian cancer." Clinical Cancer Research 23.6 (2017): 1552-1563.

Chen, Xianwen, et al. "On-bead screening of combinatorial libraries: reduction of nonspecific binding by decreasing surface ligand density." Journal of combinatorial chemistry 11.4 (2009): 604-611.

Chistiakov, Dimitry A., and Emma I. Chistiakova. "T-cell protein tyrosine phosphatase: A role in inflammation and autoimmunity." International Journal of Diabetes Mellitus 2.2 (2010): 114-118.

Cildir, Gökhan, Kee Chung Low, and Vinay Tergaonkar. "Noncanonical NF-κB signaling in health and disease." Trends in molecular medicine 22.5 (2016): 414-429.

Dai, Simon, et al. "The IκB kinase (IKK) inhibitor, NEMO-binding domain peptide, blocks osteoclastogenesis and bone erosion in inflammatory arthritis." Journal of Biological Chemistry 279.36 (2004): 37219-37222.

Davé, Shaival H., et al. "Amelioration of chronic murine colitis by peptide-mediated transduction of the IκB kinase inhibitor NEMO binding domain peptide." The Journal of Immunology 179.11 (2007): 7852-7859.

Delfin DA, et al., "Improvement of cardiac contractile function by peptide-based inhibition of NF-κB in the utrophin/dystrophin-deficient murine model of muscular dystrophy." J Transl Med. 2011;9:68. Published May 17, 2011. doi: 10.1186/1479-5876-9-68.

Dougherty, Patrick G., Ziqing Qian, and Dehua Pei. "Macrocycles as protein-protein interaction inhibitors." Biochemical Journal 474.7 (2017): 1109-1125.

Eisenberg, David, Robert M. Weiss, and Thomas C. Terwilliger. "The hydrophobic moment detects periodicity in protein hydrophobicity." Proceedings of the National Academy of Sciences 81.1 (1984): 140-144.

Elchebly, Mounib, et al. "Increased insulin sensitivity and obesity resistance in mice lacking the protein tyrosine phosphatase-1B gene." Science 283.5407 (1999): 1544-1548.

Engleman, et al. Ann. Rev. of Biophys. Biophys. Chem. 1986, 15):321-53.

Gaurnier-Hausser, Anita, et al. "NEMO-binding domain peptide inhibits constitutive NF-κB activity and reduces tumor burden in a canine model of relapsed, refractory diffuse large B-cell lymphoma." Clinical Cancer Research 17.14 (2011): 4661-4671.

Godwin, Peter, et al. "Targeting nuclear factor-kappa B to overcome resistance to chemotherapy." Frontiers in oncology 3 (2013): 120.

Gotoh, Yusuke, et al. "A homogeneous time-resolved fluorescence-based high-throughput screening system for discovery of inhibitors of IKKβ-NEMO interaction." Analytical biochemistry 405.1 (2010): 19-27.

Guo, Bingqian, et al. "Protein engineering of the N-terminus of NEMO: Structure stabilization and rescue of IKKβ binding." Biochemistry 53.43 (2014): 6776-6785.

Gupta, Subash C., et al. "Inhibiting NF-κB activation by small molecules as a therapeutic strategy." Biochimica et Biophysica Acta (BBA)-Gene Regulatory Mechanisms 1799.10-12 (2010): 775-787.

Ndikuyeze, Georges Habineza, et al. "A phase I clinical trial of systemically delivered NEMO binding domain peptide in dogs with spontaneous activated B-cell like diffuse large B-cell lymphoma." PloS one 9.5 (2014): e95404.

Hernandez, Lídia, et al. "Activation of NF-κB signaling by inhibitor of NF-κB kinase β increases aggressiveness of ovarian cancer." Cancer research 70.10 (2010): 4005-4014.

Herndon, Thomas M., et al. "US Food and Drug Administration approval: carfilzomib for the treatment of multiple myeloma." Clinical cancer research 19.17 (2013): 4559-4563.

Herrington, Felicity D., Ruaidhri J. Carmody, and Carl S. Goodyear. "Modulation of NF-κB signaling as a therapeutic target in autoimmunity." Journal of biomolecular screening 21.3 (2016): 223-242.

Hopp, Thomas P., and Kenneth R. Woods. "Prediction of protein antigenic determinants from amino acid sequences." Proceedings of the National Academy of Sciences 78.6 (1981): 3824-3828.

Ianaro, Angela, et al. "NEMO-binding domain peptide inhibits proliferation of human melanoma cells." Cancer letters 274.2 (2009): 331-336.

Janin, J. O. E. L. "Surface and inside volumes in globular proteins." Nature 277.5696 (1979): 491-492.

Jiang, Bisheng, and Dehua Pei. "A selective, cell-permeable nonphosphorylated bicyclic peptidyl inhibitor against peptidyl-prolyl isomerase Pin1." Journal of medicinal chemistry 58.15 (2015): 6306-6312.

Jimi, Eijiro, et al. "Selective inhibition of NF-κB blocks osteoclastogenesis and prevents inflammatory bone destruction in vivo." Nature medicine 10.6 (2004): 617-624.

Joo, Sang Hoon, et al. "High-throughput sequence determination of cyclic peptide library members by partial Edman degradation/mass spectrometry." Journal of the American Chemical Society 128.39 (2006): 13000-13009.

Karin, Michael. "Nuclear factor-κB in cancer development and progression." Nature 441.7092 (2006): 431-436.

Kornegay, Joe N., et al. "NBD delivery improves the disease phenotype of the golden retriever model of Duchenne muscular dystrophy." Skeletal muscle 4.1 (2014): 1-17.

Kyte, Jack, and Russell F. Doolittle. "A simple method for displaying the hydropathic character of a protein." Journal of molecular biology 157.1 (1982): 105-132.

Lian, Wenlong, et al. "Screening bicyclic peptide libraries for protein-protein interaction inhibitors: discovery of a tumor necrosis factor-α antagonist." Journal of the American Chemical Society 135.32 (2013): 11990-11995.

Lian, Wenlong, et al. "Cell-permeable bicyclic peptide inhibitors against intracellular proteins." Journal of the American Chemical Society 136.28 (2014): 9830-9833.

(56) References Cited

OTHER PUBLICATIONS

May, F. D'Acquisto, L. A. Madge, J. Glockner, J. S. Pober, S. Ghosh, Science 2000, 289, 1550.
Morrison, Kim L., and Gregory A. Weiss. "Combinatorial alanine-scanning." Current opinion in chemical biology 5.3 (2001): 302-307.
Oeckinghaus, Andrea, and Sankar Ghosh. "The NF-κB family of transcription factors and its regulation." Cold Spring Harbor perspectives in biology 1.4 (2009): a000034.
Passioura, Toby, et al. "Selection-based discovery of druglike macrocyclic peptides." Annual review of biochemistry 83 (2014): 727-752.
Peterson, Jennifer M., et al. "Peptide-based inhibition of NF-κB rescues diaphragm muscle contractile dysfunction in a murine model of Duchenne muscular dystrophy." Molecular Medicine 17.5 (2011): 508-515.
Qian, et al., "Enhancing the Cell Permeability and Metabolic Stability of Peptidyl Drugs by Reversible Bicyclization", Angew. Chem. Int. Ed. 2017, 56, 1525-1529.
Qian, Ziqing, et al. "Early endosomal escape of a cyclic cell-penetrating peptide allows effective cytosolic cargo delivery." Biochemistry 53.24 (2014): 4034-4046.
Qian, Ziqing, et al. "Discovery and mechanism of highly efficient cyclic cell-penetrating peptides." Biochemistry 55.18 (2016): 2601-2612.
Reay, M. Yang, J. F. Watchko, M. Daood, T. L. O'Day, K. K. Rehman, D. C. Guttridge, P. D. Robbins, P. R. Clemens, Neurobiol. Dis. 2011, 43, 598.
Rothwarf, David M., et al. "IKK-γ is an essential regulatory subunit of the IκB kinase complex." Nature 395.6699 (1998): 297-300.
Rushe, Mia, et al. "Structure of a NEMO/IKK-associating domain reveals architecture of the interaction site." Structure 16.5 (2008): 798-808.
Shibata, Wataru, et al. "Cutting edge: the IκB kinase (IKK) inhibitor, NEMO-binding domain peptide, blocks inflammatory injury in murine colitis." The Journal of Immunology 179.5 (2007): 2681-2685.
Shrake, Andrew, and John A. Rupley. "Environment and exposure to solvent of protein atoms. Lysozyme and insulin." Journal of molecular biology 79.2 (1973): 351-371.
Sun, Shao-Cong, Jae-Hoon Chang, and Jin Jin. "Regulation of nuclear factor-κB in autoimmunity." Trends in immunology 34.6 (2013): 282-289.
Thakkar, Amit, Anne-Sophie Wavreille, and Dehua Pei. "Traceless capping agent for peptide sequencing by partial Edman degradation and mass spectrometry." Analytical chemistry 78.16 (2006): 5935-5939.
Tien, Matthew Z., et al. "Maximum allowed solvent accessibilities of residues in proteins." PloS one 8.11 (2013): e80635.
Trinh, Thi B., et al. "Discovery of a direct Ras inhibitor by screening a combinatorial library of cell-permeable bicyclic peptides." ACS combinatorial science 18.1 (2016): 75-85.
Upadhyaya, Punit, et al. "Inhibition of Ras signaling by blocking Ras-effector interactions with cyclic peptides." Angewandte Chemie International Edition 54.26 (2015): 7602-7606.
Verma, Udit N., et al. "Nuclear role of IκB kinase-γ/NF-κB essential modulator (IKKγ/NEMO) in NF-κB-dependent gene expression." Journal of Biological Chemistry 279.5 (2004): 3509-3515.
Yamaoka, Shoji, et al. "Complementation cloning of NEMO, a component of the IKB kinase complex essential for NF-κB activation." Cell 93.7 (1998): 1231-1240.
Zhang, Zhong-Yin. "Drugging the undruggable: therapeutic potential of targeting protein tyrosine phosphatases." Accounts of chemical research 50.1 (2017): 122-129.
Zhang, Sheng, et al. "Acquisition of a potent and selective TC-PTP inhibitor via a stepwise fluorophore-tagged combinatorial synthesis and screening strategy." Journal of the American Chemical Society 131.36 (2009): 13072-13079.
Zugazagoitia, Jon, et al. "Current challenges in cancer treatment." Clinical therapeutics 38.7 (2016): 1551-1566.
Sporn, Michael B., and Nanjoo Suh. "Chemoprevention of cancer." Carcinogenesis 21.3 (2000): 525-530.
Alhakamy, N. A., Nigatu, A. S., Berkland, C. J., and Ramsey, J. D. (2013) Noncovalently associated cell-penetrating peptides for gene delivery applications. Ther. Deliv. 4, 741-757.
Ali, Syed Ausaf et al. "A review of methods available to estimate solvent-accessible surface areas of soluble proteins in the folded and unfolded states." Current Protein and Peptide Science 15.5 (2014): 456-476.
Ali, Ameena et al., Stapled Peptides Inhibitors: A New Window for Target Drug Discovery, Computational and Structural Biotechnology Journal, vol. 17, Jan. 1, 2019, pp. 263-281.
Almarsson, Örn, and Michael J. Zaworotko. "Crystal engineering of the composition of pharmaceutical phases. Do pharmaceutical co-crystals represent a new path to improved medicines?" Chemical communications 17 (2004): 1889-1896.
Altschul, Stephen F., et al. "Gapped BLAST and PSI-BLAST: a new generation of protein database search programs." Nucleic acids research 25.17 (1997): 3389-3402.
Altschul, Stephen F., et al. "Basic local alignment search tool." Journal of molecular biology 215.3 (1990): 403-410.
Alzani, R. et al. "Suramin induces deoligomerization of human tumor necrosis factor alpha." J. Biol. Chem. 268, (1993): 12526-12529.
Andaloussi, S. E. L. et al., "Design of a peptide-based vector, PepFect6, for efficient delivery of siRNA in cell culture and systemically in vivo," Noucleic Acids Research, May 2011, 39(9):3972-3987.
Ander, J. et al., "Chemical modification allows phallotoxins and amatoxins to be used as tools in cell biology," Beilstein Journal of Organic Chemistry, 2012, 8(233):2072-2084.
Angelini, Alessandro, et al. "Bicyclic peptide inhibitor reveals large contact interface with a protease target." ACS chemical biology 7.5 (2012): 817-821.
Appelbaum, Jacob S., et al. "Arginine topology controls escape of minimally cationic proteins from early endosomes to the cytoplasm." Chemistry & biology 19.7 (2012): 819-830.
Aramburu, J.; et al., "Selective inhibition of NFAT activation by a peptide spanning the calcineurin targeting site of NFAT." Mol. Cell 1998, 1, 627-637.
Aramburu, J.; et al., "Affinity-driven peptide selection of an NFAT inhibitor more selective than cyclosporine A." Science 1999, 285, 2129-2133.
Ardi, V. C., et al., "Macrocycles that inhibit the binding between heat shock protein 90 and TPR-containing proteins." ACS Chem. Biol. 6, (2011): 1357-1366.
Arthanari, Y.; Pluen, A.; Rajendran, R.; Aojula, H.; Demonacos, C. (2010) Delivery of therapeutic shRNA and siRNA by Tat fusion peptide targeting bcr-abl fusion gene in Chronic Myeloid Leukemia cells. J. Controlled Release 145, 272-280.
Assem, N., et al., (2015) "Acetone-linked peptides: a convergent approach for peptide macrocyclization and labeling". Angew. Chem. Int. Ed. 54, 8665-8668.
Barford, D. et al. "Crystal structure of human protein tyrosine phosphatase 1B." Science 263.5152 (1994): 1397-1404.
Baxevanis, et al., Bioinformatics A Practical Guide to the Analysis of Genes and Proteins, Wiley, 1998.
Beste, G. et al. "Small antibody-like proteins with prescribed ligand specificities derivedfrom the lipocalin fold." Proc. Natl. Acad. Sci. USA 96, (1999): 1898-1903.
Beutler, B. et al. "Purification of cachectin, a lipoprotein-lipase suppressing hormone secreted by endotoxin-induced RAW 264.7 cells." J. Exp. Med. 161, (1985): 984-995.
Bird, Gregory H., et al. "Biophysical determinants for cellular uptake of hydrocarbon-stapled peptide helices." Nature chemical biology 12.10 (2016): 845-852.
Birts, C. N. et al. "A cyclic peptide inhibitor of C-terminal binding protein dimerization links metabolism with mitotic fidelity in breast cancer cells." Chem. Sci., 4, (2013): 3046-3057.
Biswas, G., et al., "Synthesis of Ibuprofen Conjugated Molecular Transporter Capable of Enhanced Brain Penetration" Hindawi Journal of Chemistry, vol. 2017, Article ID 4746158, 2017, 10 pages.

(56) References Cited

OTHER PUBLICATIONS

Bockus, et al., Going Out on a Limb: Delineating the Effects of β-Branching, N-Methylation, and Side Chain Size on the Passive Permeability, Solubility, and Flexibility of Sanguinamide A Analogues J. Med. Chem. 2015, 58:7409.

Bold, G.; et al., "New aza-dipeptide analogues as potent and orally absorbed HIV-1 protease inhibitors: candidates for clinical development." J. Med. Chem. 1998, 41, 3387-3401. abstract.

Bolte, S. et al., A guided tour into subcellular colocalization analysis in light microscopy, J. Microsc., Dec. 2006, 224(Pt. 3), 213-232.

Borrelli, Antonella et al., Cell Penetrating Peptides as Molecular Carriers for Anti-Cancer Agents, Molecules, vol. 23, No. 2, Jan. 1, 2018.

Böttcher, Thomas, et al. "Synthesis and activity of biomimetic biofilm disruptors." Journal of the American Chemical Society 135.8 (2013): 2927-2930.

Bowie et al. Deciphering the message in protein sequences: tolerance to amino acid substitutions (Science, 1990, 247:1306-1310) (Year: 1990).

Buller, F., et al. "Discovery of TNF inhibitors from a DNA-encoded chemical library based on Diels-Alder cycloaddition." Chem. Biol. 16, (2009): 1075-1086.

Burgess et al. Possible dissociation of the heparin-binding and mitogenic activities of heparin-binding (acidic fibroblast) growth factor-1 from its receptor-binding activities by site-directed mutagenesis of a single lysine residue. (J. Cell Biol. 111:2129-2138, 1990) (Year: 1990).

Burke, T.R. Jr. et al., "Potent Inhibition of Insulin Receptor Dephosphorylation by a Hexamer Peptide Containing the Phosphotyrosyl Mimetic F2Pmp," Biochem. Biophys. Res. Commun., Oct. 1994, 204(1):129-134.

Buyanova, M. et al., Discovery of a Bicyclic Peptidyl Pan-Ras Inhibitor Sep. 9, 2021;64(17):13038-13053.

Calvo, Sarah E., and Vamsi K. Mootha. "The mitochondrial proteome and human disease." Annual review of genomics and human genetics 11 (2010): 25-44.

Carpenter, A E. et al., "CellProfiler: image analysis software for identifying and quantifying cell phenotypes," Genome Biology, 2006, 7:R100, 11 pages.

Cascales, L. et al., "Identification and Characterization of a New Family of Cell-Penetrating Peptides," J. Biol. Chem., Oct. 2011, 286(42):36932-36943.

Cerrato, Carmine Pasquale, et al. "Novel cell-penetrating peptide targeting mitochondria." The FASEB Journal 29.11 (2015): 4589-4599.

Chan, D. S. et al. "Structure-based discovery of natural-product-like TNF-a inhibitors." Angew. Chem. Int. Ed. Engl. 49, (2010): 2860-2864.

Chapman, J. R. "Chronic calcineurin inhibitor nephrotoxicity—lest we forget." Am. J. Transplant 2011, 11, 693-697.

Chatterjee, Jayanta, et al. "N-methylation of peptides: a new perspective in medicinal chemistry." Accounts of chemical research 41.10 (2008): 1331-1342.

Chen et al. "Bicyclic Peptide Ligands Pulled out of Cysteine-Rich Peptide Libraries," JACS, 135(17), (2013): 6562-6569.

Chen, G. & Goeddel, D. V. "TNF-R1 signaling: a beautiful pathway." Science 296, (2002): 1634-1635.

Chen, S., et al., "Structurally diverse cyclization linkers impose different backbone conformations in bicyclic peptides." ChemBioChem. 13, (2012): 1032-1038.

Chen, S. et al., "Dithiol amino acidscan structureally shape and enhance the ligand-binding properties of polypeptides." Nature chemistry 6.11 (2014): 1009-1016.

Chen, K. and Pei, D. "Engineering cell-permeable proteins through insertion of cell-penetrating motifs into surface loops." ACS chemical biology 15.9 (2020): 2568-2576.

Chen et al., Fusion protein linkers: property, design and functionality. Adv. Drug. Deliv. Rev. 65:1357-1369 (Year 2013).

Cheng, Seng H., et al. "Defective intracellular transport and processing of CFTR is the molecular basis of most cystic fibrosis." Cell 63.4 (1990): 827-834.

Chierici, S.; et al., "A case study of 2,2-dimethylthiazolidine as locked cis proline amide bond: synthesis, NMR and molecular modeling studies of a-conotoxin EVIA peptide analog." Org. Biomol. Chem. 2004, 2, 2436-2441.

Chinnery, P. F., et al. "Peptide nucleic acid delivery to human mitochondria." Gene therapy 6.12 (1999): 1919-1928.

Choi et al., "Cell permeable NFAT inhibitory peptide Sim-2-VIVIT inhibits sT-cell activation and alleviates allergic airways inflammation and hyper-responsiveness", Immunology Letters 143:2 pp. 170-176.

Choi, H., et al., "Discovery of the inhibitors of tumor necrosis factor alpha with structure-based virtual screening." Bioorg. Med. Chem. Lett. 20, (2010): 6195-6198.

Choi, Hee-Jung, Andrew H. Huber, and William I. Weis. "Thermodynamics of β-catenin-ligand interactions: the roles of the N- and C-terminal tails in modulating binding affinity." Journal of Biological Chemistry 281.2 (2006): 1027-1038.

Chu, Qian, et al. "Towards understanding cell penetration by stapled peptides." MedChemComm 6.1 (2015): 111-119.

clinicaltrials.gov identifier: NCT02264613, First Posted: Oct. 15, 2014.

Cochran, Andrea G., Nicholas J. Skelton, and Melissa A. Starovasnik. "Tryptophan zippers: Stable, monomeric β-hairpins." Proceedings of the National Academy of Sciences 98.10 (2001): 5578-5583.

Collins, M., and Thrasher, A. (2015) Gene therapy: progress and predictions. Proc. R. Soc. B 282, 20143003.

Cooley, Christina B., et al. "Oligocarbonate molecular transporters: oligomerization-based syntheses and cell-penetrating studies." Journal of the American Chemical Society 131.45 (2009): 16401-16403.

Crabtree, G. R. "Generic signals and specific outcomes: signaling through Ca2+, calcineurin, and NF-AT." Cell 1999, 96, 611-614.

Craik, David J., et al. "The future of peptide-based drugs." Chemical biology & drug design 81.1 (2013): 136-147.

Cromm, PM at al. Orthogonal ring-closing alkyne and olefin metathesis for the synthesis of small GTPase-targeting bicyclic peptides. Nature Communications, vol. 7, Apr. 14, 2016, publication 11300, doh 10.1038/ncomms11300, p. 1-7.

Cromm, P. et al., "Hydrocarbon stapled peptides as modulators of biological function." ACS chemical biology 10.6 (2015): 1362-1375.

Cushing, P. R. et al., "The Relative Binding Affinities of PDZ Partners for CFTR: A Biochemical Basis for Efficient Endocytic Recycling," Biochemistry, 2008, 47(38): 10084-10098.

Cushing, Patrick R., et al. "A Stabilizing Influence: CAL PDZ Inhibition Extends the Half-Life of ΔF508-CFTR." Angewandte Chemie International Edition 49.51 (2010): 9907-9911.

Dash, S at al. Deficiency of the RNA Binding Protein Caprin2 Causes Lens Defects and Features of Peters Anomaly. Developmental Dynamics, vol. 244, No. 10, Oct. 2015, published online Aug. 7, 2015, doi: 10.1002/dvdy.24303, pp. 1313-13127.

Davies, S. J.; et al., "Structure-activity relationships of the peptide deformylase inhibitor BB-3497: modification of the P2' and P3' side chains." Bioorg. Med. Chem. Lett. 2003, 13, 2715-2718.

DePaul, A. J.; et al., "Equilibrium conformational dynamics in an RNA tetraloop from massively parallel molecular dynamics." Nucleic Acids Res. 2010, 38, 4856-4867.

Deshayes, Sebastien, et al. "Cell-penetrating peptides: tools for intracellular delivery of therapeutics." Cellular and Molecular Life Sciences CMLS 62.16 (2005): 1839-1849.

Desimmie, B. A. et al. "Phage Display-directed Discovery of LEDGF/p75 Binding Cyclic Peptide Inhibitors of HIV Replication." Mol. Therapy 20, (2012): 2064-2075.

Dewan, V. et al. "Cyclic peptide inhibitors of HIV-I capsid-human lysyl-tRNA synthetase interaction." ACS Chem. Biol. 7, (2012):761-769.

Diderich, Philippe, et al., Phage Selection of Chemically Stabilized α-Helical Peptide Ligands, ACS Chemical Biology, vol. 11, No. 5, Mar. 11, 2016, pp. 1422-1427.

(56) References Cited

OTHER PUBLICATIONS

Dietrich, L. et al., "Cell permeable stapled peptide inhibitor of Wnt signaling that targets beta-catenin protein-protein interactions." Cell chemical biology 24.8 (2017): 958-968.
Do, H. et al., "Difatty acyl-conjugated linear and cyclic peptides for siRNA delivery." ACS omega 2.10 (2017): 6939-6957.
Dong et al., A Photocontrolled β-Hairpin Peptide. Chemistry—A European Journal. 2006, 12 (4): 1114-1120.
Doran, Todd M., et al. "Role of amino acid hydrophobicity, aromaticity, and molecular volume on IAPP (20-29) amyloid self-assembly." Proteins: Structure, Function, and Bioinformatics 80.4 (2012): 1053-1065.
D'Souza et al., Structural parameters modulating the cellular uptake of disulfide-rich cyclic cell-penetrating peptides: MCoTI-II and SFTI-1, European Journal of Medicinal Chemistry, vol. 88, 99 10-18, 2014.
Dougherty, Patrick et al., Enhancing the Cell Permeability of Stapled Peptides with a Cyclic Cell-Penetrating Peptide, Journal of Medicinal Chemistry, vol. 62, No. 22, Oct. 28, 2019, pp. 10098-10107.
Dowdy, S. F. (2017) Overcoming cellular barriers for RNA therapeutics. Nat. Biotechnol. 35, 222-229.
Doyle, D. A et al., "Crystal Structures of a Complexed and Peptide-Free Membrane Protein-Binding Domain: Molecular Basis of Peptide Recognition by PDZ," Cell, Jun. 1996, 85(7):1067-1076.
Driggers, E. M. et al., "The exploration of macrocycles for drug discovery—an underexploited structural class," Nat. Rev. Drug Discov., Jul. 2008, 7:608-624.
Drysdale, Martin J., et al. "Targeting Hsp90 for the treatment of cancer." Current opinion in drug discovery & development 9.4 (2006): 483-495. Abstract.
Duchardt, Falk, et al. "A comprehensive model for the cellular uptake of cationic cell-penetrating peptides." Traffic 8.7 (2007): 848-866.
Duchardt, F. et al., "A Cell-penetrating Peptide Derived from Human Lactoferrin with Conformation-dependent Uptake Efficiency," J. Biol. Chem., Dec. 2009, 284(52):36099-36108.
Dumy, P.; et al., "Pseudo-prolines as a molecular hinge: reversible induction of cis amide bonds into peptide backbones." J. Am. Chem. Soc. 1997, 119, 918-925.
Eguchi, Akiko, et al. "Protein transduction domain of HIV-1 Tat protein promotes efficient delivery of DNA into mammalian cells." Journal of Biological Chemistry 276.28 (2001): 26204-26210.
Eichler, J. et al., "Novel a-glucosidase inhibitors identified using multiple cyclic peptide combinatorial libraries," Molecular Diversity, Aug. 1996, 1(4):233-240.
El Andaloussi, Samir, et al. "Design of a peptide-based vector, PepFect6, for efficient delivery of siRNA in cell culture and systemically in vivo." Nucleic acids research 39.9 (2011): 3972-3987.
El-Sayed, Ayman, Shiroh Futaki, and Hideyoshi Harashima. "Delivery of macromolecules using arginine-rich cell-penetrating peptides: ways to overcome endosomal entrapment." The AAPS journal 11.1 (2009): 13-22.
Engel, Marisa, et al. "Regiospecific synthesis of 3, 5-bis (bromomethyl) benzoic acid, a cysteine crosslinking agent." Tetrahedron 49.39 (1993): 8761-8770.
Ernster, Lars, and Gottfried Schatz. "Mitochondria: a historical review." The Journal of cell biology 91.3 (1981): 227s-255s.
Esposito, E. & Cuzzocrea, S. "TNF-alpha as a therapeutic target in inflammatory diseases, ischemia-reperfusion injury and trauma." Curr. Med. Chem. 16, (2009): 3152-3167.
Fang, Shengyun, et al. "Mdm2 is a RING finger-dependent ubiquitin protein ligase for itself and p53." J. Biol. Chem. 275.12 (2000): 8945-8951.
Fernández-Carneado, Jimena, et al. "Highly efficient, nonpeptidic oligoguanidinium vectors that selectively internalize into mitochondria." Journal of the American Chemical Society 127.3 (2005): 869-874.

Fernandez-Lopez, S. et al., "Antibacterial agents based on the cyclic D,L-alpha-peptide architecture," Nature, Jul. 2001, 412:452-455 and Correction page, Nature, Nov. 2001, 414:329.
Ferrari, Aldo, et al. "Caveolae-mediated internalization of extracellular HIV-1 tat fusion proteins visualized in real time." Molecular therapy 8.2 (2003): 284-294.
Fittipaldi, Antonio, et al. "Cell membrane lipid rafts mediate caveolar endocytosis of HIV-1 Tat fusion proteins." Journal of Biological Chemistry 278.36 (2003): 34141-34149.
Fosgerau, Keld, and Torsten Hoffmann. "Peptide therapeutics: current status and future directions." Drug discovery today 20.1 (2015): 122-128.
Frackenpohl, J. et al., "The Outstanding Biological Stability of - and y-Peptides toward Proteolytic Enzymes: An In Vitro Investigation with Fifteen Peptidases," Chembiochem, Jun. 2001, 2(6):445-455.
Frankel, Alan D., and Carl O. Pabo. "Cellular uptake of the tat protein from human immunodeficiency virus." Cell 55.6 (1988): 1189-1193.
Frost, J. R. et al., "Macrocyclization of Organo-Peptide Hybrids through a Dual Bio-orthogonal Ligation: Insights from Structure-Reactivity Studies," ChemBioChem, Jan. 2013, 14(1):147-160.
Furka, A., et al. "General method for rapid synthesis of multicomponent peptide mixtures." Int. J. Pep. Prat. Res. 37, (1991): 487-493.
R. Furumai, et al., Potent histone deacetylase inhibitors built from trichostatin A and cyclic tetrapeptide antibiotics including trapoxin. Proc. Natl. Acad. Sci. U. S. A., 2001, 98:87.
Futaki, Shiroh. "Membrane-permeable arginine-rich peptides and the translocation mechanisms." Advanced drug delivery reviews 57.4 (2005): 547-558.
Futaki, S. et al., "Arginine-rich peptides. An abundant source of membrane-permeable peptides having potential as carriers for intracellular protein delivery." The Journal of Biological Chemistry, 2001, 276(8):5836-5840.
Gaj, T., Gersbach, C. A., and Barbas, C. F. (2013) ZFN, TALEN, and CRISPR/Cas-based methods for genome engineering. Trends Biotechnol. 31, 397-405.
GenBank: AEV23320.1. "Beta-fibrinogen, partial [Boana albopunctata]." Feb. 13, 2012. https://www.ncbi.nlm.nih.gov/protein/AEV23320.1?report-genbank&log$=protalign&blast_rank=3&RID=FMTADBYS014. 1 page.
Giacca, M., and Zacchigna, S. (2012) Virus-mediated gene delivery for human gene therapy. J. Controlled Release 161, 377-388.
GiebeL, L. B. et al., "Screening of cyclic peptide phage libraries identifies ligands that bind streptavidin with high affinities," Biochemistry, 1995, 34(47): 15430-15435.
Gobbo, M. et al., "Synthesis and biological activity of some linear and cyclic kinin analogues," International Journal of Peptide & Protein Research, Jul. 1994, 44(1):1-9.
Goncalves, E. et al., "Binding of Oligoarginine to Membrane Lipids and Heparan Sulfate: Structural and Thermodynamic Characterization of a Cell-Penetrating Peptide," Biochemistry, 2005, 44(7):2692-2702.
Goun, Elena A., et al. "Molecular transporters: synthesis of oligoguanidinium transporters and their application to drug delivery and real-time imaging." Chem Bio Chem 7.10 (2006): 1497-1515.
Green, Maurice, and Paul M. Loewenstein. "Autonomous functional domains of chemically synthesized human immunodeficiency virus tat trans-activator protein." Cell 55.6 (1988): 1179-1188.
Grigoriu, S.; et al., "The molecular mechanism of substrate engagement and immunosuppressant inhibition of calcineurin." PLoS Biol. 2013, 11, e1001492.
Gupta, Bhawna, Tatiana S. Levchenko, and Vladimir P. Torchilin. "Intracellular delivery of large molecules and small particles by cell-penetrating proteins and peptides." Advanced drug delivery reviews 57.4 (2005): 637-651.
Gwack, Y.; et al., "A genome-wide *Drosophila* RNAi screen identifies DYRK-family kinases as regulators of NFAT." Nature 2006, 441, 646-650.
Hamill, K. M. et al., "Polyrnyxins facilitate entry into mammalian cells" Chem. Sci., 2016, 7:5059-5068.
Hancock R., et al., Peptide inhibitors of the Keap1-Nrf2 protein-protein interaction. Free Radic. Biol. Med. 52, (2012):444-451.

(56) References Cited

OTHER PUBLICATIONS

Hardee, C., Arévalo-Soliz, L., Hornstein, B., and Zechiedrich, L. (2017) Advances in Non-Viral DNA Vectors for Gene Therapy. Genes 8, 65.

Hariton-Gazal, E. et al., "Functional Analysis of Backbone Cyclic Peptides Bearing the Arm Domain of the HIV-1 Rev Protein: Characterization of the Karyophilic Properties and Inhibition of Rev-Induced Gene Expression," Biochemistry, 2005, 44(34): 11555-11566.

He et al., Peptide Conjugates with Small Molecules Designed to Enhance Efficacy and Safety. Molecules, 2019, 24, 1855 (Year 2019).

He, M. M. et al. "Small-molecule inhibition of TNF-a." Science 310, (2005): 1022-1025.

He, R et al., "Recent Advances in PTP1B Inhibitor Development for the Treatment of Type 2 Diabetes and Obesity," Chapter 6 In: New Therapeutic Strategies for Type 2 Diabetes: Small Molecule Approaches, Jones, R. M. (ed.), RSC Drug Discovery Series No. 27, The Royal Society of Chemistry, 2012, pp. 142-176.

Heinis, C., Rutherford, T., Freund, S. & Winter, G. "Phage-encoded combinatorial chemical libraries based on bicyclic peptides." Nat. Chem. Biol. 5, (2009): 502-507.

Herce, H. D., et al. "Arginine-rich peptides destabilize the plasma membrane, consistent with a pore formation translocation mechanism of cell-penetrating peptides." Biophysical journal 97.7 (2009): 1917-1925.

Herce, Henry D., and Angel E. Garcia. "Molecular dynamics simulations suggest a mechanism for translocation of the HIV-1 TAT peptide across lipid membranes." Proceedings of the National Academy of Sciences 104.52 (2007): 20805-20810.

Hili, R. et al., "Macrocyclization of Linear Peptides Enabled by Amphoteric Molecules," J. Am. Chem. Soc., 2010, 132(9):2889-2891.

Hintersteiner, M. et al. "Single bead labeling method for combining confocal fluorescence on-bead screening and solution validation of tagged one-bead one-compound libraries." Chem. Biol. 16, (2009): 724-735.

Hirose, Hisaaki, et al. "Transient focal membrane deformation induced by arginine-rich peptides leads to their direct penetration into cells." Molecular Therapy 20.5 (2012): 984-993.

Hojo, M.; et al., "Cyclosporine induces cancer progression by a cell-autonomous mechanism." Nature 1999, 397, 530-534.

Holub, J. M. et al., "Improved assays for determining the cytosolic access of peptides, proteins, and their mimetics," Biochemistry, Dec. 2013, 52(50):9036-9046.

Horn, M. et al., "Tuning the properties of a novel short cell-penetrating peptide by intramolecular cyclization with a triazole bridge," Chem. Commun. 2016, 52:2261-2264.

Horton, Kristin L., et al. "Mitochondria-penetrating peptides." Chemistry & biology 15.4 (2008): 375-382.

Houghten, R. A et al. "Generation and use of synthetic peptide combinatorial libraries for basic research and drug discovery." Nature 354, (1991): 84-86.

Hoye, Adam T., et al. "Targeting mitochondria." Accounts of chemical research 41.1 (2008): 87-97.

Hoyer, J. A. N., and Ines Neundorf. "Peptide vectors for the nonviral delivery of nucleic acids." Accounts of chemical research 45.7 (2012): 1048-1056.

Hu, B. H., Jones, M. R. & Messersmith, P. B. "Method for screening and MALDI-TOF MS sequencing of encoded combinatorial libraries." Anal. Chem. 79, (2007): 7275-7285.

Hu, B., Gilkes, D. M., and Chen, J. (2007) Efficient p53 activation and apoptosis by simultaneous disruption of binding to MDM2 and MDMX. Cancer Res. 67, 8810-8817.

Huang, Xinghua, et al. "Slipping synthesis of cucurbit [7] uril-based [2] rotaxane in organic environment." Tetrahedron Letters 53.47 (2012): 6414-6417.

Huang, H-C., Truyen Nguyen, and Cecil B. Pickett. "Regulation of the antioxidant response element by protein kinase C-mediated phosphorylation of NF-E2-related factor 2." Proceedings of the National Academy of Sciences 97.23 (2000): 12475-12480.

Humphrey, W.; et al., "VMD: visual molecular dynamics." J. Mol. Graphics 1996, 14, 33-38.

Illsley, N. P. et al., "Membrane chloride transport measured using a chloride-sensitive fluorescent probe," Biochemistry, 1987, 26(5):1215-1219.

Inoyama, Daigo, et al. "Optimization of fluorescently labeled Nrf2 peptide probes and the development of a fluorescence polarization assay for the discovery of inhibitors of Keap1-Nrf2 interaction." Journal of biomolecular screening 17.4 (2012): 435-447.

Ishii, Tetsuro, et al. "Transcription factor Nrf2 coordinately regulates a group of oxidative stress-inducible genes in macrophages." Journal of Biological Chemistry 275.21 (2000): 16023-16029.

Isidro-Llobet, Albert, Mercedes Alvarez, and Fernando Albericio. "Amino acid-protecting groups." Chemical reviews 109.6 (2009): 2455-2504.

Jang, S. et al., "Cell-Penetrating, Dimeric a-Helical Peptides: Nanomolar Inhibitors of HIV-1 Transcription", Angew. Chem. Int. Ed. 2014, 53, 10086-10089.

Jean, Sae Rin, et al. "Peptide-mediated delivery of chemical probes and therapeutics to mitochondria." Accounts of chemical research 49.9 (2016): 1893-1902.

Jeong, Ji Hoon, et al. "siRNA conjugate delivery systems." Bioconjugate chemistry 20.1 (2008): 5-14.

Jha, D. et al., "CyLoP-1: A Novel Cysteine-Rich Cell-Penetrating Peptide for Cytosolic Delivery of Cargoes," Bioconj. Chem., 2011, 22(3):319-328.

Jo, Hyunil, et al. "Development of a-helical calpain probes by mimicking a natural protein-protein interaction." J. Am. Chem. Soc. 134.42 (2012): 17704-17713.

Johnson, Mark L., and Nalini Rajamannan. "Diseases of Wnt signaling." Reviews in Endocrine and Metabolic Disorders 7 (2006): 41-49.

Jójárt, B.; et al., "Performance of the general amber force field in modeling aqueous POPC membrane bilayers." J. Comput. Chem. 2007, 28, 2051-2058.

Joo, Sang Hoon. "Cyclic peptides as therapeutic agents and biochemical tools." Biomolecules & therapeutics 20.1 (2012): 19-26.

Jorgensen, W. L.; et al., "Solvation and Conformation of Methanol in Water." J. Am. Chem. Soc. 1983, 105, 1407-1413.

Josephson, Lee, et al. "High-efficiency intracellular magnetic labeling with novel superparamagnetic-Tat peptide conjugates." Bioconjugate chemistry 10.2 (1999): 186-191.

Joy, Stephen T., and Paramjit S. Arora. "An optimal hydrogen-bond surrogate for α-helices." Chemical Communications 52.33 (2016): 5738-5741.

Juliano, R. L. (2016) The delivery of therapeutic oligonucleotides. Nucleic Acids Res. 44(14): 6518-6548.

Junkes, Christof, et al. "Cyclic antimicrobial R-, W-rich peptides: the role of peptide structure and E. coli outer and inner membranes in activity and the mode of action." European Biophysics Journal 40.4 (2011): 515-528.

Kaduk, C.; et al., "Synthesis of Fmoc-amino acid fluorides via DAST, an alternative fluoridation agent." Lett. Pep. Sci. 1995, 2, 285-288.

Kang, Byoung Heon, et al. "Combinatorial drug design targeting multiple cancer signaling networks controlled by mitochondrial Hsp90." The Journal of clinical investigation 119.3 (2009): 454-464.

Kang, S.; et al., "Inhibition of the calcineurin-NFAT interaction by small organic molecules reflects binding at an allosteric site." J. Biol. Chem. 2005, 280, 37698-37706.

Kansanen, Emilia, et al. "The Keap1-Nrf2 pathway: mechanisms of activation and dysregulation in cancer." Redox biology 1.1 (2013): 45-49.

Kaplan, Ian M., Jehangir S. Wadia, and Steven F. Dowdy. "Cationic TAT peptide transduction domain enters cells by macropinocytosis." Journal of Controlled Release 102.1 (2005): 247-253.

Karpurapu et al., "Inhibition of nuclear factor of activated T cells (NFAT) c3 activation attenuates acute lung injury and pulmonary edema in murine models of sepsis", Oncotarget 9(12), pp. 10606-10620.

(56) References Cited

OTHER PUBLICATIONS

Kawakami, T. et al., "In Vitro Selection of Multiple Libraries Created by Genetic Code Reprogramming to Discover Macrocyclic Peptides That Antagonize VEGFR2 Activity in Living Cells," ACS Chem. Biol., Apr. 2013, 8(6):1205-1214.
Kawakami, M., & Cerami, A. Studies of endotoxin-induced decrease in lipoprotein-lipase activity. J. Exp. Med. 154, (1981): 631-639.
Kerem, Bat-sheva, et al. "Identification of the cystic fibrosis gene: genetic analysis." Science 245.4922 (1989): 1073-1080.
Khabar, K. S., Siddiqui, S. & Armstrong, J. A. "WEHI-13V AR: a stable and sensitive variant of WEHI 164 clone 13 fibrosarcoma for tumor necrosis factor bioassay." Immunol. Lett. 46, (1995): 107-110.
Khakshoor, Omid, and James S. Nowick. "Artificial β-sheets: chemical models of β-sheets." Current opinion in chemical biology 12.6 (2008): 722-729.
Kiani, A.; et al., "Manipulating immune responses with immuno-suppressive agents the target NFAT." Immunity 2000, 12, 359-372.
Kim, Young-Woo et al., "Synthesis of all-hydrocarbon stapled alpha-helical peptides by ring-closing olefin metathesis." Nature protocols 6.6 (2011): 761-772.
Kim, W. et al., "Protein tyrosine phosphotase conjugated with a novel transdermal delivery peptide, astrotactin 1-derived peptide recombinant protein tyrosine phosphatase (AP-rPTP), alleviates both atopic dermatitis-like and psoriasis-like dermatitis." Journal of Allergy and Clinical Immunology 141.1 (2018): 137-151.
Kimber, Matthew S., et al. "Structural basis for specificity switching of the Src SH2 domain." Molecular cell 5.6 (2000): 1043-1049.
Kodadek, T. & Bachhawat-Sikder, K. "Optimized protocols for the isolation of specific protein-binding peptides or peptoids from combinatorial libraries displayed on beads." Mol. BioSyst. 2, (2006): 25-35.
Kohli, R. M. et al., "Biomimetic synthesis and optimization of cyclic peptide antibiotics," Nature, Aug. 2002, 418:658-661.
Koide, A. et al. "The fibronectin type III domain as a scaffold for novel binding proteins." J. Mol. Biol. 284, (1998): 1141-1151.
Kriegler, M. et al. "A Novel Form of TNF/cachectin Is a Cell Surface Cytotoxic Transmembrane Protein: Ramifications for the Complex Physiology of TNF." Cell 53, (1988): 45-53.
Kritzer, J. A. et al., "Rapid selection of cyclic peptides that reduce a-synuclein toxicity in yeast and animal models," Nature Chemical Biology, Sep. 2009, 5(9):655-663.
Kundu, R. et al., "Hybrid Organic-Inorganic Inhibitors of a PDZ Interaction that Regulates the Endocytic Fate of CFTR," Angew. Chem. Int. Ed., Jul. 2012, 51(29):7217-7220.
Kwon, Y-U et al., "Quantitative Comparison of the Relative Cell Permeability of Cyclic and Linear Peptides," Chemistry & Biology, Jun. 2007, 14(6):671-677.
Lächelt, U., and Wagner., E. (2015) Nucleic Acid Therapeutics Using Polyplexes: A Journey of 50 Years (and Beyond). Chem. Rev. 115, 11043-11078.
Lai, Jonathan R., et al. "Design of non-cysteine-containing antimicrobial β-hairpins: Structure-activity relationship studies with linear protegrin-1 analogues." Biochemistry 41.42 (2002): 12835-12842.
Lalonde, M.S. et al., "Inhibition of Both HIV-1 Reverse Transcription and Gene Expression by a Cyclic Peptide that Binds the Tat-Transactivating Response Element (TAR) RNA", PLoS Pathogenes May 2011, 7(5) e1002038.
Lam, K. S. et al. "A new type of synthetic peptide library for identifying ligand-binding activity." Nature 354, (1991): 82-84.
Lamontagne, K. R. Jr. et al., "Protein tyrosine phosphatase PTP1B suppresses p210 bcr-abl-induced transformation of Rat-1 fibroblasts and promotes differentiation of K562 cells," Proc. Natl. Acad. Sci. U. S. A., Nov. 1998, 95(24):14094-14099.
Langham, Allison A., Alan J. Waring, and Y. N. Kaznessis. "Comparison of interactions between beta-hairpin decapeptides and SDS/DPC micelles from experimental and simulation data." BMC biochemistry 8.1 (2007): 1-13.
LaRochelle, Jonathan R., et al. "Fluorescence correlation spectroscopy reveals highly efficient cytosolic delivery of certain penta-arg proteins and stapled peptides." Journal of the American Chemical Society 137.7 (2015): 2536-2541.
Lättig-Tünnemann, Gisela, et al. "Backbone rigidity and static presentation of guanidinium groups increases cellular uptake of arginine-rich cell-penetrating peptides." Nature communications 2 (2011): 453.
Lau, Yu Heng, et al. "Peptide stapling techniques based on different macrocyclisation chemistries." Chemical Society Reviews 44.1 (2015): 91-102.
Law, M., Jafari, M., and Chen, P. (2008) Physicochemical characterization of siRNA-peptide complexes. Biotechnol Prog, 24, 957-963.
Lazar et al., (Mol. Cell Biol. 8:1247-1252, 1988).
Leduc, A. M. et al. "Helix-stabilized cyclic peptides as selective inhibitors of steroid receptor-coactivator interactions." Proc. Natl. Acad. Sci. USA 100, (2003): 11273-11278.
Lee, H. J. et al., "PDZ domains and their binding partners: structure, specificity, and modification," Cell Communication and Signaling, 2010, 8:8, 18 pages.
Lee, J. et al., "Using marine natural products to discover a protease that catalyzes peptide macrocyclization of diverse substrates," J. Am. Chem. Soc., Feb. 2009, 131(6):2122-2124.
Lee et al. Identification and Characterization of a Novel Integrin-Linked Kinase Inhibitor, Journal of Medicinal Chemistry, 2011, vol. 54, Iss. 18, p. 6364-6374, Publish Online Aug. 8, 2011.
Lessard, L. et al., "The two faces of PTP1B in cancer," Biochim. Biophys. Acta, Mar. 2010, 1804(3):613-619.
Leung, C. H. et al. "Structure-based repurposing of FDA-approved drugs as TNF-a inhibitors." ChemMedChem 6, (2011): 765-768.
Lewis, Kaitlyn N., et al. "Nrf2, a guardian of healthspan and gatekeeper of species longevity." Integrative and comparative biology 50.5 (2010): 829-843.
Li, H.; et al., "Interaction of calcineurin with substrates and targeting proteins." Trends Cell Biol. 2011, 21, 91-103.
Li, H.; et al., "Structural delineation of the calcineurin-NFAT interaction and its parallels to PP1 targeting interactions." J. Mol. Biol. 2004, 342, 1659-1674.
Li, H.; et al., "Structure of calcineurin in complex with PVIVIT peptide: portrait of a low-affinity signaling interaction." J. Mol. Biol. 2007, 369, 1296-1306.
Li, S. et al, "Photolithographic synthesis of cyclic peptide arrays using a differential deprotection strategy," Chem. Commun., 2005, 5:581-583.
Li, S. et al., "Fluoride enhances the activity of fungicides that destabilize cell membranes," Bioorganic & Medicinal Chemistry Letters, 2012, 22(9):3317-3322.
Liao et al., Cell-permeable bicyclic peptidyl inhibitors against T-cell protein tyrosine phosphates from a combinatorial library, Organic & Biomolecular Chemistry, vol. 15, pp. 9595-9598, 2017.
Lightfoot, H. et al., "Endogenous polyamine function—the RNA perspective." Nucleic acids research 42.18 (2014): 11275-11290.
Lin, K-J, et al., "QSAR studies of antimicrobial alpha, beta-polypeptides," Pharmaceutical Biotechnology, 2003, 10(5):299-303 (with English Abstract).
Lindgren M. et al., "Classes and Prediction of Cell-Penetrating Peptides," Chapter 1 In: Cell-Penetrating Peptides: Methods and Protocols, Methods in Molecular Biology, vol. 683, pp. 3-19, Springer Science+Business Media, LLC 2011.
Liu, et al., Cyclic Peptidyl Inhibitors against Human Peptidyl-Prolyl Isomerase Pin1. J Med Chem; 2010, 53: 2491-2501.
Liu, T. et al., "Membrane permeable cyclic peptidyl inhibitors against human Peptidylprolyl Isomerase Pin1." Journal of medicinal chemistry 53.6 (2010): 2494-2501.
Liu, Jianquan, et al. "Nanostructured materials designed for cell binding and transduction." Biomacromolecules 2.2 (2001): 362-368.
Liu, R., Maril, J. & Lam, K. S. "A novel peptide-based encoding system for "one-bead one-compound" peptidomimetic and small molecule combinatorial libraries." J. Am. Chem. Soc. 124, (2002): 7678-7680.
Liu, T. et al. "Synthesis and screening of a cyclic peptide library: Discovery of small-molecule ligands against human prolactin receptor." Bioorg. Med. Chem. 17, (2009): 1026-1033.

(56) References Cited

OTHER PUBLICATIONS

Liu, T., Qian, Z., Xiao, Q. & Pei, D. "High-throughput screening of one-bead-one compound libraries: identification of cyclic peptidyl inhibitors against calcineurin/NF AT interaction." ACS Comb. Sci. 13, (2011): 537-546.
Liu, T. et al., "Membrane Permeable Cyclic Peptidyl Inhibitors against Human Peptidylprolyl Isomerase Pin1," J. Med. Chem., 2010, 53(6):2494-2501.
Liu, X., Chen, C. & Hop, C. E. "Do we need to optimize plasma protein and tissue binding in drug discovery?" Curr. Top. Med. Chem. 11, (2011):450-466.
Liu, Y. et al., "Multifunctional Tandem Peptide Modified Paclitaxel-Loaded Liposomes for the Treatment of Vasculogenic Mimicry and Cancer Stem Cells in Malignant Glioma," ACS Applied Materials & Interfaces, 2015, 7(30):16792-16801.
Liu, J.; et al., "Calcineurin is a common target of cyclophilin-cyclosporine A and FKBP-FK506 complexes." Cell 1991, 66, 807-815.
Llinas-Brunet, M.; et al., "A systematic approach to the optimization of substrate-based inhibitors of the hepatitis C virus NS3 protease: discovery of potent and specific tripeptide inhibitors." J. Med. Chem. 2004, 47, 6584-6594.
Lo, Shih-Ching, et al. "Structure of the Keap1: Nrf2 interface provides mechanistic insight into Nrf2 signaling." The EMBO journal 25.15 (2006): 3605-3617.
Lu, K. P. et al., "The prolyl isomerase PIN1: a pivotal new twist in phosphorylation signalling and disease," Nat. Rev. Mol. Cell Biol., Nov. 2007, 8:904-916.
Lu et al., Linkers Having a Crucial Role in Antibody-Drug Conjugates. International Journal of Molecular Sciences, 2016, 17, 561, 1-22 (Year 2016).
Luechapanichkul, R.; et al., "Specificity profiling of dual specificity phosphatase vaccinia VH1-related (VHR) reveals two distinct substrate binding modes." J. Biol. Chem. 2013, 288, 6498-6510.
Luzi et al. Subunit disassembly and inhibition of TNFalpha by a semi-synthetic bicyclic peptide, Protein Engineering, Design, & Selection 28(2), (2015): 45-52.
Ma, Bing, et al. "Total synthesis of the antimitotic bicyclic peptide celogentin c." Journal of the American Chemical Society 132.3 (2009): 1159-1171.
Ma, L. et al. "A Novel Small-Molecule Tumor Necrosis Factor α Inhibitor Attenuates Inflammation in a Hepatitis Mouse Model." J. Biol. Chem. 289, (2014): 12457-12466.
Ma, Yan, et al. "Direct cytosolic delivery of cargoes in vivo by a chimera consisting of D- and L-arginine residues." Journal of controlled release 162.2 (2012): 286-294.
Madden, Michael M., et al. "Synthesis of cell-permeable stapled peptide dual inhibitors of the p53-Mdm2/Mdmx interactions via photoinduced cycloaddition." Bioorganic & Med. Chem. Lett. 21.5 (2011): 1472-1475.
Magzoub, M. et al., "Conformational states of the cell-penetrating peptide penetratin when interacting with phospholipid vesicles: effects of surface charge and peptide concentration," Biochim. Biophys. Acta, Jun. 2002, 1563(1-2):53-63.
Majer et al., Structure-based substitute specificity mappingh of human cathespin D using statine-based inhibitors, Protein Science, vol. 6, pp. 1458-1466, 1997.
Maiolo, et al. "Effects of cargo molecules on the cellular uptake of arginine-rich cell-penetrating peptides." Biochimica et Biophysica Acta (BBA)—Biomembranes 1712.2 (2005): 161-172.
Maiti, Kaustabh K., et al. "Guanidine-containing molecular transporters: sorbitol-based transporters show high intracellular selectivity toward mitochondria." Angewandte Chemie 119.31 (2007): 5984-5988.
Maly, D. J. et al., "Combinatorial Strategies for Targeting Protein Families: Application to the Proteases," Chembiochem, Jan. 2002, 3(1):16-37.
Maly, D. J. et al., "Expedient Solid-Phase Synthesis of Fluorogenic Protease Substrates Using the 7-Amino-4-carbamoylmethylcoumarin (ACC) Fluorophore," J. Org. Chem., 2002, 67(3):910-915.
Malty, Ramy H., et al. "Mitochondrial targets for pharmacological intervention in human disease." Journal of proteome research 14.1 (2015): 5-21.
Mancini, F., Toro, C. M., Mabilia, M., Giannangeli, M., Pinza, M. & Milanese, C. Inhibition of tumor necrosis factor-a (TNF-a)—TNF-a receptor binding by structural analogues of suramin. Biochem. Pharmocol. 58, (1999): 851-859.
Mandal, Deendayal, Amir Nasrolahi Shirazi, and Keykavous Parang. "Cell-penetrating homochiral cyclic peptides as nuclear-targeting molecular transporters." Angewandte Chemie International Edition 50.41 (2011): 9633-9637.
Markovac, Anica, and Maurice P. LaMontagne. "Antimalarials. 12. Preparation of carbon isosteres of selected 4-pyridinemethanols as suppressive antimalarials." Journal of medicinal chemistry 23.11 (1980): 1198-1201.
Marsault, E. et al., "Macrocycles Are Great Cycles: Applications, Opportunities, and Challenges of Synthetic Macrocycles in Drug Discovery," J. Med. Chem., 2011, 54(7): 1961-2004.
Martin, T. L., Mufson, E. J. & Mesulam, M. M. The light side of horseradish peroxidase histochemistry. J. Histochem. Cytochem. 32, (1984):793.
Matsson, P. et al., Cell permeability beyond the rule of 5. Adv. Drug Deliv. Rev. 2016, 101:42.
Meutermans, W. D. F. et al., "Synthesis of Difficult Cyclic Peptides by Inclusion of a Novel Photolabile Auxiliary in a Ring Contraction Strategy," J. Am. Chem. Soc., 1999, 121(42):9790-9796. Published Online: Oct. 8, 1999.
Meyer, Daniel, et al. "Aromatic interactions with naphthylalanine in a β-hairpin peptide." Journal of Peptide Science 19.5 (2013): 277-282.
Millward, S.W., et al., "Design of cyclic peptides that bind protein surfaces with antibody-like affinity." ACS Chem. Biol. 2, (2007): 625-634.
Millward, S. W. et al., "A General Route for Post-Translational Cyclization of mRNA Display Libraries," J. Am. Chem. Soc., 2005, 127(41):14142-14143. Published Online: Sep. 27, 2005.
Ming, Z. et al., ""Synthesis of RGD containing peptides and their vasodilation effect,"" Preparative Biochemistry 8 Biotechnology, 2000, 30(3):247-256.
Miranda, E. et al. "A Cyclic Peptide Inhibitor of HIF-1 Heterodimerization That Inhibits Hypoxia Signaling in Cancer Cells." J. Am. Chem. Soc. 135, (2013): 10418-10425.
Mishra, Abhijit, et al. "Translocation of HIV TAT peptide and analogues induced by multiplexed membrane and cytoskeletal interactions." Proceedings of the National Academy of Sciences 108.41 (2011): 16883-16888.
Miskolzie, M. et al., "An NMR conformational analysis of cyclic bradykinin mimics. Evidence for a-turn," Journal of Biomolecular Structure & Dynamics, 2000, 17(6):947-955.
Mitra, Sayantan, and Amy M. Barrios. "Highly sensitive peptide-based probes for protein tyrosine phosphatase activity utilizing a fluorogenic mimic of phosphotyrosine." Bioorganic & medicinal chemistry letters 15.23 (2005): 5142-5145.
Moore, J. D. et al., "Pin1 inhibitors: Pitfalls, progress and cellular pharmacology," Bioorg. Med. Chem. Lett., Aug. 2013, 23(15):4283-4291.
Morais Cabral, J. H. et al., "Crystal structure of a PDZ domain," Nature, Aug. 1996, 382:649-652.
Mosmann, T., "Rapid colorimetric assay for cellular growth and survival: Application to proliferation and cytotoxicity assays," J. Immunol. Methods, Dec. 1983, 65(1-2):55-63.
Mueller, Judith, et al. "Comparison of cellular uptake using 22 CPPs in 4 different cell lines." Bioconjugate chemistry 19.12 (2008): 2363-2374.
Muratovska, Aleksandra, and Michael R. Eccles. "Conjugate for efficient delivery of short interfering RNA (siRNA) into mammalian cells." FEBS letters 558.1-3 (2004): 63-68.
Murphy, M. P. "Biochimica et Biophysica Acta Targeting lipophilic cations to mitochondria." Biochim. Biophys. Acta Bioenerg 1777 (2008): 1028-1031.
Nair et al. A Dual-Targeting Octaguanidine-Doxorubicin Conjugate Transporter for Inducing Caspase-Mediated Apoptosis on Folate-Expressing Cancer Cells. (ChemMedChem, 2016, 11(7), 702.

(56) References Cited

OTHER PUBLICATIONS

Nair et al. (ChemMedChem, 2016, 11(7), 702. STN abstract.
Nair et al. (ChemMedChem, 2016, 11(7), 702, Supporting Information.
Nakase, Ikuhiko, et al. "Efficient intracellular delivery of nucleic acid pharmaceuticals using cell-penetrating peptides." Accounts of chemical research 45.7 (2011): 1132-1139.
Nakase, Ikuhiko, et al. "Interaction of arginine-rich peptides with membrane-associated proteoglycans is crucial for induction of actin organization and macropinocytosis." Biochemistry 46.2 (2007): 492-501.
Needleman, Saul B., and Christian D. Wunsch. "A general method applicable to the search for similarities in the amino acid sequence of two proteins." Journal of molecular biology 48.3 (1970): 443-453.
Nevola, Laura, and Ernest Giralt. "Modulating protein-protein interactions: the potential of peptides." Chemical Communications 51.16 (2015): 3302-3315.
Nguyen, Leonard T., et al. "Serum stabilities of short tryptophan- and arginine-rich antimicrobial peptide analogs." PloS one 5.9 (2010): e12684.
Ngu-Schwemlein, M. et al., "In vitro synergy between some cationic amphipathic cyclooctapeptides and antibiotics," Australian Journal of Chemistry, 2015, 68(2):218-223.
Nischan, N. et al., "Covalent Attachment of Cyclic TAT Peptides to GFP Results in Protein Delivery into Live Cells with Immediate Bioavailability," Angew. Chem. Int. Ed., 2015, 54:1950-1953, with Supporting Information pp. S1-S26.
Noguchi, H.; et al., "A new cell-permeable peptide allows successful allogeneic islet transplantation in mice." Nat. Med. 2004, 10, 305-309.
Nori, Aparna, et al. "Tat-conjugated synthetic macromolecules facilitate cytoplasmic drug delivery to human ovarian carcinoma cells." Bioconjugate chemistry 14.1 (2003): 44-50.
Ocampo-Garcia, B. E. et al., "Design and biological evaluation of 99mTc-N2S2-Tat(49-57)-c(RGDyK): A hybrid radiopharmaceutical for tumors expressing a(v)(3) integrins," Nuclear Medicine and Biology (2013), 40(4):481-487.
Oh, D. et al., "Antibacterial activities of amphiphilic cyclic cell-penetrating peptides against multidrug-resistant pathogens," Molecular Pharmaceutics, 2014, 11(10):3528-3536.
Oh, D. et al., "Amphiphilic Bicyclic Peptides as Cellular Delivery Agents," ChemMedChem, 2014, 9(11):2449-2453.
Oh, D. et al., "Enhanced cellular uptake of short polyarginine peptides through fatty acylation and cyclization." Molecular pharmaceutics 11.8 (2014): 2845-2854.
Okamoto, H. et al., "Conformational transitions of cyclic D,L-Peptides," Journal of Computational Chemistry, 2009, 30(6):962-973.
Orange et al. "Cell penetrating peptide inhibitors of Nuclear Factor-kappa B," Cell Mol Life Sci, 2008, 62(22), 3564-3591.
Palm-Apergi, Caroline, et al. "The membrane repair response masks membrane disturbances caused by cell-penetrating peptide uptake." The FASEB Journal 23.1 (2009): 214-223.
Pande et al., Synthesis and Antibacterial Evaluation of Carboxamide Derivatives of Amino Acids. (Pharmaceutical Chemistry Journal, vol. 48, No. 1, Apr. 2014).
Pathak, Rakesh K., Nagesh Kolishetti, and Shanta Dhar. "Targeted nanoparticles in mitochondrial medicine." Wiley Interdisciplinary Reviews: Nanomedicine and Nanobiotechnology 7.3 (2015): 315-329.
Pawson, T. et al., "Assembly of Cell Regulatory Systems Through Protein Interaction Domains," Science, Apr. 2003, 300(5618) :445-452.
Pelay-Gimeno, Marta, et al. "Structure-based design of inhibitors of protein-protein interactions: mimicking peptide binding epitopes." Angewandte Chemie International Edition 54.31 (2015): 8896-8927.
Pelay-Gimeno, Marta, et al. "Strukturbasierte Entwicklung von Protein-Protein-Interaktionsinhibitoren: Stabilisierung und Nachahmung von Peptidliganden." Angewandte Chemie 127.31 (2015): 9022-9054.
Peng, Q., Zhong, Z., and Zhuo, R. (2008) Disulfide Cross-Linked Polyethylenimines (PEI) Prepared via Thiolation of Low Molecular Weight PEI as Highly Efficient Gene Vectors. Bioconjugate Chem. 19, 499-506.
Pennica, D. et al. "Human Tumour Necrosis Factor: Precursor Structure, Expression and Homology to Lymphotoxin." Nature 312, (1984):724-729.
Perni, R. B.; et al., "Preclinical profile of VX-950, a potent, selective, and orally bioavailable inhibitor of hepatitis C Virus NS3-4A serine protease." Antimicrob. Agents Chemother. 2006, 50, 899-909.
Pettersen, E. F.; et al., "UCSF Chimera—a visualization system for exploratory research and analysis." J. Comput. Chem. 2004, 13, 1605-1612.
Pham, Wellington, et al. "Enhancing membrane permeability by fatty acylation of oligoarginine peptides." Chembiochem 5.8 (2004): 1148-1151.
Phan, Jason, et al. "Structure-based design of high affinity peptides inhibiting the interaction of p53 with MDM2 and MDMX." J. Biol. Chem. 285.3 (2010): 2174-2183.
Platz, K. P.; et al., "Nephrotoxicity following orthotopic liver transplantation. A comparison between cyclosporine and FK506." Transplantation 1994, 58, 170-178.
Pomilio, A B. et al., "Naturally-Occurring Cyclopeptides: Structures and Bioactivity," Current Organic Chemistry, Nov. 2006, 10(16):2075-2121.
Pooga, Margus, et al. "Cellular translocation of proteins by transportan." The FASEB Journal 15.8 (2001): 1451-1453.
Pritz, S. et al., "Synthesis of Biologically Active Peptide Nucleic Acid-Peptide Conjugates by Sortase-Mediated Ligation," Journal of Organic Chemistry, 2007, 72(10):3909-3912.
Qian, Ziqing, et al. "Efficient delivery of cyclic peptides into mammalian cells with short sequence motifs." ACS chemical biology 8.2 (2012): 423-431.
Qian, Ziqing, et al. "Intracellular delivery of peptidyl ligands by reversible cyclization: discovery of a PDZ domain inhibitor that rescues CFTR activity." Angewandte Chemie International Edition 54.20 (2015): 5874-5878. Angew. Chem. 2015, 127, 5972.
Qian, Ziqing, et al. "Monitoring the cytosolic entry of cell-penetrating peptides using a pH-sensitive fluorophore." Chemical Communications 51.11 (2015): 2162-2165.
Qian et al., "Structure-Based Optimization of a Peptidyl Inhibitor against Calcineurin-Nuclear Factor of Activated T Cell (NFAT) Interaction." J. Med. Chem. 2014, 57, 7792-7797.
Qin, C. et al., "Optimization of Antibacterial Cyclic Decapeptides," J. Comb. Chem., 2004, 6(3):398-406.
R-Group_SASA_and LogP_as Hydrophobicity Measure Claims 97 and 100; generated in ChemOffice Excel 2010 (Year 2022).
Rajendran, Peramaiyan, et al. "Antioxidants and human diseases." Clinica chimica acta 436 (2014): 332-347.
Rao, A.; et al., "Transcription factors of the NFAT family: regulation and function." Annu. Rev. Immunol. 1997, 15, 707-747.
Reineke, E.L. et al., Degradation of the Tumor Suppressor PML by Pin1 Contributes to the Cancer Phenotype of Breast Cancer MDA-MB-231 Cells. Mol. Cell. Biol., 2008, 28:997.
Ren, L. et al., "Substrate Specificity of Protein Tyrosine Phosphatases 18, RPTPa, SHP-1, and SHP-2," Biochemistry, 2011, 50(12):2339-2356.
Rezai, Taha, et al. "Conformational flexibility, internal hydrogen bonding, and passive membrane permeability: successful in silico prediction of the relative permeabilities of cyclic peptides." Journal of the American Chemical Society 128.43 (2006): 14073-14080.
Rezai, T. et al., "Testing the Conformational Hypothesis of Passive Membrane Permeability Using Synthetic Cyclic Peptide Diastereomers," J. Am. Chem. Soc., 2006, 128(8):2510-2511.
Rice, Peter, Ian Longden, and Alan Bleasby. "EMBOSS: the European molecular biology open software suite." Trends in genetics 16.6 (2000): 276-277.

(56) References Cited

OTHER PUBLICATIONS

Richard, Jean Philippe, et al. "Cellular uptake of unconjugated TAT peptide involves clathrin-dependent endocytosis and heparan sulfate receptors." Journal of Biological Chemistry 280.15 (2005): 15300-15306.
Ricouart, A et al., "Design of potent protein kinases inhibitors using the bisubstrate approach," Journal of Medicinal Chemistry, 1991, 34(1):73-78.
Riedl, S. J. et al., "Molecular mechanisms of caspase regulation during apoptosis," Nat. Rev. Mol. Cell Biol., Nov. 2004, 5:897-907.
Roberts, K. D. et al., "Efficient synthesis of thioether-based cyclic peptide libraries," Tetrahedron Letters, Nov. 1998, 39(45):8357-8360.
Roberts, K. E. et al., "Computational Design of a PDZ Domain Peptide Inhibitor that Rescues CFTR Activity," Plos Computational Biology, Apr. 2012, 8(4): e1002477, 12 pages.
Robinson, John A. "β-Hairpin peptidomimetics: design, structures and biological activities." Accounts of chemical research 41.10 (2008): 1278-1288.
Rothbard, Jonathan B., et al. "Conjugation of arginine oligomers to cyclosporin A facilitates topical delivery and inhibition of inflammation." Nature medicine 6.11 (2000): 1253.
Rotstein, B. H. et al., "Solvatochromic Reagents for Multicomponent Reactions and their Utility in the Development of Cell-Permeable Macrocyclic Peptide Vectors," 2011, Chem. Eur. J., 17:12257-12261.
Roy, J.; et al., "Cracking the phosphatase code: Docking interactions determine substrate specificity." Sci. Signal. 2009, 2, re9, 1-7.
Rueping, Magnus, et al. "Cellular uptake studies with β-peptides." ChemBioChem 3.2-3 (2002): 257-259.
Rusnati, M. et al., "Multiple Interactions of HIV-I Tat Protein with Size-defined Heparin Oligosaccharides," J. Biol. Chem., Oct. 1999, 274(40):28198-28205.
Rutledge, S.E., Volkman, H.M. & Schepartz,"A. Molecular recognition of protein surfaces: high affinity ligands for the CBPKIX domain." J. Am. Chem. Soc. 125, (2003): 14336-14347.
Saar, Külliki, et al. "Cell-penetrating peptides: a comparative membrane toxicity study." Analytical biochemistry 345.1 (2005): 55-65.
Sahin, U., Karikó, K., and Türeci, Ö. (2014) mRNA-based therapeutics—developing a new class of drugs. Nat. Rev. Drug Discov. 13, 759-780.
Saito, H. et al. "A tumor necrosis factor receptor loop peptide mimic inhibits bone destruction to the same extent as anti-tumor necrosis factor monoclonal antibody in murine collagen-induced arthritis." Arthritis Rheum. 56, (2007):1164-1174.
Sakamoto, K et al. Generation of KS 68 as the first K Ras(G120) inhibitory peptide presenting anti cancer activity in vivo. Scientific Reports, vol. 10, No. 1, Dec. 10, 2020, publication 21671, pp. 1-16.
Sako, Y., Morimoto, J., Murakami, H. & Suga, H. "Ribosomal synthesis of bicyclic peptides via two orthogonal inter-side-chain reactions." J. Am. Chem. Soc. 130, (2008): 7232-7234.
Salvado, I. et al., "Membrane-disrupting iridium(lll) oligocationic organometallopeptides," Chemical Communications, 2016, 52(73): 11008-11011.
Sandberg, Mats, et al. "NRF2-regulation in brain health and disease: implication of cerebral inflammation." Neuropharmacology 79 (2014): 298-306.
Schafmeister, C. E. et al., "An All-Hydrocarbon Cross-Linking System for Enhancing the Helicity and Metabolic Stability of Peptides," J. Am. Chem. Soc., 2000, 122(24):5891-5892.
Schmidt, Nathan, et al. "Arginine-rich cell-penetrating peptides." FEBS letters 584.9 (2010): 1806-1813.
Scholl, Markus, Zuzana Kadlecova, and Harm-Anton Klok. "Dendritic and hyperbranched polyamides." Progress in Polymer Science 34.1 (2009): 24-61.
Schwarze, Steven R., et al. "In vivo protein transduction: delivery of a biologically active protein into the mouse." Science 285.5433 (1999): 1569-1572.

Scott, C. P. et al., "Production of cyclic peptides and proteins in vivo," Proc. Natl. Acad. Sci. U. S. A., Nov. 1999, 96(24):13638-13643.
Seisel, Q. et al., "Optimization of the process of inverted peptides (PIPEPLUS) to screen PDZ domain ligands." Bioorganic & medicinal chemistry letters 27.14 (2017): 3111-3116.
Shair, Matthew D. "A closer view of an oncoprotein-tumor suppressor interaction." Chem. & Biol. 4.11 (1997): 791-794.
Shen, Q. et al., "De novo design of helical peptides to inhibit tumor necrosis factor-α by disrupting its trimer formation." Med. Chem. Commun. 7, (2016): 725-729.
Shepherd, Nicholas E., et al. "Single turn peptide alpha helices with exceptional stability in water." Journal of the American Chemical Society 127.9 (2005): 2974-2983.
Shi, B. et al. (2011) Biodistribution of Small Interfering RNA at the Organ and Cellular Levels after Lipid Nanoparticle-mediated Delivery. J Histochem Cytochem. 59(8): 727-740.
Shirazi, A. N. et al., "Cysteine and arginine-rich peptides as molecular carriers," Bioorg. Med. Chem. Lett., 2016, 26:656-661.
Shirazi, A. N. et al., "Cyclic Peptide-Capped Gold Nanoparticles as Drug Delivery Systems," Molecular Pharmaceutics, 2013, 11:500-511.
Shirazi, A. N. et al., "Design and Biological Evaluation of Cell-Penetrating Peptide-Doxorubicin Conjugates as Prodrugs," Molecular Pharmaceutics, 2013, 10:488-499.
Shirazi, A. N. et al., "Cyclic peptides containing tryptophan and arginine as Src kinase inhibitors", Bioorganic & Medicinal Chemistry Letters 23 (2013) 3230-3234.
Sieber, M.; et al., "Novel inhibitors of the calcineurin/NFATc hub—alternatives to CsA and FK506?" Cell Commun. Signal. 2009, 7, 25.
Sigal, N. H.; et al., "Is cyclophilin involved in the immunosuppressive and nephrotoxic mechanism of action of cyclosporine A?" J. Exp. Med. 1991, 173, 619-628.
Sigman, M. S.; et al., "Schiff base catalysts for the asymmetric Strecker reaction identified and optimized from parallel synthetic libraries." J. Am. Chem. Soc. 1998, 120, 4901-4902.
Skelton, Nicholas J., et al. "β-hairpin polypeptides by design and selection." Journal of Spectroscopy 17.2-3 (2003): 213-230.
Slee, E. A. et al., "Benzyloxycarbonyl-Val-Ala-Asp (OMe) fluoromethylketone (Z-VAD.FMK) inhibits apoptosis by blocking the processing of CPP32," Biochemical Journal, Apr. 1996, 315(1):21-24.
Songyang, Z. et al., "Recognition of Unique Carboxyl-Terminal Motifs by Distinct PDZ Domains," Science, Jan. 1997, 275(5296):73-77.
Sorin, E. J.; et al., "Exploring the helix-coil transition via all-atom equilibrium ensemble simulations." Biophys. J. 2005, 88, 2472-2493.
Sousa da Silva, A. W.; et al., "ACPYPE—AnteChamberPYthon Parser interfacE." BMC Res. Notes 2012, 5, 367.
Srinivas, et al., Biaryl amino acid templates in place of D-Pro-L-Pro in cyclic beta-hairpin cationic antimicrobial peptidemimetics, Organic and Biomolecular Chemistry vol. 5, pp. 3100-3105, 2007.
Stanford, Stephanie M., et al. "High-throughput screen using a single-cell tyrosine phosphatase assay reveals biologically active inhibitors of tyrosine phosphatase CD45." Proceedings of the National Academy of Sciences 109.35 (2012): 13972-13977.
Stebbins, Charles E., et al. "Crystal structure of an Hsp90-geldanamycin complex: targeting of a protein chaperone by an antitumor agent." Cell 89.2 (1997): 239-250.
Steiner, D., Forrer, P. & Plueckthun, A. "Efficient selection of DARPins with subnanomolar affinities using SRP phage display." J. Mol. Biol. 382, (2008):1211-1227.
Stewart, Kelly M., Kristin L. Horton, and Shana O. Kelley. "Cell-penetrating peptides as delivery vehicles for biology and medicine." Organic & biomolecular chemistry 6.13 (2008): 2242-2255.
Stewart, J. M. et al., "Bradykinin antagonists: Anti-cancer drugs for the new millennium?" Peptides for the New Millennium, Proceedings of the American Peptide Symposium, 16th, Minneapolis, MN, United States, Jun. 26-Jul. 1, 1999 (2000), Meeting Date 1999, 219-221. Fields, G. B. et al., (eds.), Kluwer Academic Publishers, Dordrecht, Neth.

(56) References Cited

OTHER PUBLICATIONS

Suhorutsenko, Julia, et al. "Cell-penetrating peptides, PepFects, show no evidence of toxicity and immunogenicity in vitro and in vivo." Bioconjugate chemistry 22.11 (2011): 2255-2262.
Sun, Y., Lu, G. & Tam, J. P. "A thioester ligation approach to amphipathic bicyclic peptide library." Org. Lett. 3, (2001): 1681-1684.
Sun, Y. et al., "Establishment of MicroRNA delivery system by PP7 bacteriophage-like particles carrying cell-penetrating peptide." Journal of bioscience and bioengineering 124.2 (2017): 242-249.
Sweeney, M. C et al. "Decoding protein-protein interactions through combinatorial chemistry: sequence specificity of SHP-1, SHP-2, and SHIP SH2 domains." Biochemistry 44, (2005): 14932-14947.
Taguchi, Keiko, Hozumi Motohashi, and Masayuki Yamamoto. "Molecular mechanisms of the Keap1-Nrf2 pathway in stress response and cancer evolution." Genes to cells 16.2 (2011): 123-140.
Tai, Z., Wang, X., Tian, J., Gao, Y., Zhang, L., Yao, C., Wu, X., Zhang, W., Zhu, Q., and Gao, S. (2015) Biodegradable Stearylated Peptide with Internal Disulfide Bonds for Efficient Delivery of siRNA In Vitro and In Vivo. Biomacromolecules 16, 1119-1130.
Takada, Y. et al. "Evodiamine Abolishes Constitutive and Inducible NF-κB Activation by Inhibiting IκBα Kinase Activation, Thereby Suppressing NF-κB-regulated Antiapoptotic and Metastatic Gene Expression, Up-regulating Apoptosis, and Inhibiting Invasion." J. Biol. Chem. 280, (2005): 17203-17212.
Takasaki,W.,et al., "Structure-based design and characterization of exocyclic peptidomimetics that inhibit TNF alpha binding to its receptor." Nat. Biotechnol. 15, (1997): 1266-1270.
Takeuchi, K.; et al., "Structure of the calcineurin-NFAT complex: defining a T cell activation switch using solution NMR and crystal coordinates." Structure 2007, 15, 587-597.
Tam, J. P. et al., "Disulfide bond formation in peptides by dimethyl sulfoxide. Scope and applications," J. Am. Chem. Soc., 1991, 113(17):6657-6662.
Tan, Yaw Sing, et al. "Stapled peptide design: principles and roles of computation." Drug Discovery Today 21.010 (2016): 1642-1653.
Tan, X. et al., "Closing the loop: constraining TAT peptide by γPNA hairpin for enhanced cellular delivery of biomolecules." Bioconjugate Chemistry 29.9 (2018): 2892-2898.
Tang, P. et al. "Human pro-Tumor Necrosis Factor Is a Homotrimer." Biochemistry (Mosc.) 35, (1995): 8216-8225.
Tavassoli, A., et al., "Inhibition of HN budding by a genetically selected cyclic peptide targeting the Gag-TSG 101 interaction." ACS Chem. Biol. 3, (2008): 757-764.
Thornberry, N. A. et al., "A Combinatorial Approach Defines Specificities of Members of the Caspase Family and Granzyme B. Functional Relationships Established for Key Mediators of Apoptosis," J. Biol. Chem., Jul. 1997, 272(29):17907-17911.
Tian, Yuan et al., "Achieving enhanced cell penetration of short conformationally constrained peptides through amphiphilicity tuning." Chemical science 8.11 (2017): 7576-7581.
Timmerman, P. et al. "A combinatorial approach for the design of complementarity determining region-derived peptidomimetics with in vitro anti-tumoral activity." J. Biol. Chem. 284, (2009): 34126-34134.
Tong, Kit I., et al. "Different electrostatic potentials define ETGE and DLG motifs as hinge and latch in oxidative stress response." Molecular and cellular biology 27.21 (2007): 7511-7521.
Tong, Kit I., et al. "Keap1 recruits Neh2 through binding to ETGE and DLG motifs: characterization of the two-site molecular recognition model." Molecular and cellular biology 26.8 (2006): 2887-2900.
Toogood, Peter L. "Mitochondrial drugs." Current opinion in chemical biology 12.4 (2008): 457-463.
Toro et al., "TAT-mediated intracellular delivery of purine nucleoside phosphorylase corrects its deficiency in mice." The Journal of clinical investigation 116.10 (2006): 2717-2726.
Traboulsi, H. et al., "Macrocyclic Cell Penetrating Peptides: A Study of Structure-Penetration Properties," Bioconjugate Chemistry, 2015, 26:405-411.

Tse, B. N. et al., "Translation of DNA into a Library of 13 000 Synthetic Small-Molecule Macrocycles Suitable for in Vitro Selection," J. Am. Chem. Soc., 2008, 130(46):15611-15626.
Turner, R. A. et al., "Click chemistry as a macrocyclization tool in the solid-phase synthesis of small cyclic peptides," Org. Lett., Nov. 2007, 9(24): 5011-5014. Epub Oct. 23, 2007.
Tyagi, M. et al., "Internalization of HIV-1 Tat requires cell surface heparan sulfate proteoglycans," J. Biol. Chem., Feb. 2001, 276(5):3254-3261. Epub Oct. 6, 2000.
Upadhyaya, et al. "Direct Ras inhibitors identified from a structurally ridigified bicyclic peptide library." Tetrahedron, 2014, 70(42), 7714-7720.
Varkouhi, Amir K., et al. "Endosomal escape pathways for delivery of biologicals." Journal of Controlled Release 151.3 (2011): 220-228.
Van Goor, F. et al., "Correction of the F508del-CFTR protein processing defect in vitro by the investigational drug VX-809," Proc. Natl. Acad. Sci. U. S. A., Nov. 2011, 108(46):18843-18848.
Varland, Sylvia, Camilla Osberg, and Thomas Arnesen. "N-terminal modifications of cellular proteins: The enzymes involved, their substrate specificities and biological effects." Proteomics 15.14 (2015): 2385-2401.
Vassilev, Lyubomir T., et al. "In vivo activation of the p53 pathway by small-molecule antagonists of MDM2." Science 303.5659 (2004): 844-848.
G. L. Verdine et al., Clin. Cancer Res., 2007, 13:7264.
Verdine, Gregory L., and Gerard J. Hilinski. "Stapled peptides for intracellular drug targets." Methods in enzymology. vol. 503. Academic Press, 2012. 3-33.
Virta, P. & Lonnberg, H. J. "Solid-supported synthesis of cryptand-like macrobicyclic peptides." J. Org. Chem. 68, (2003): 8534.
Vriens, Kim, Bruno Cammue, and Karin Thevissen. "Antifungal plant defensins: mechanisms of action and production." Molecules 19.8 (2014): 12280-12303.
Wade, Mark, Yao-Cheng Li, and Geoffrey M. Wahl. "MDM2, MDMX and p53 in oncogenesis and cancer therapy." Nature Reviews Cancer 13.2 (2013): 83-96.
Wadia, Jehangir S., and Steven F. Dowdy. "Transmembrane delivery of protein and peptide drugs by TAT-mediated transduction in the treatment of cancer." Advanced drug delivery reviews 57.4 (2005): 579-596.
Wajant, H. et al. "Tumor Necrosis Factor Signaling." Cell Death Differ 10, (2003): 45-65.
Walensky, Loren D., et al. "Activation of apoptosis in vivo by a hydrocarbon-stapled BH3 helix." Science 305.5689 (2004): 1466-1470.
Walensky, Loren D., and Gregory H. Bird. "Hydrocarbon-stapled peptides: principles, practice, and progress: miniperspective." Journal of medicinal chemistry 57.15 (2014): 6275-6288.
Wallbrecher, R. et al., "Exploration of the Design Principles of a Cell-Penetrating Bicylic Peptide Scaffold," Bioconjugate Chemistry, 2014, 25(5):955-964. Published Online: Apr. 3, 2014.
Wang, C-W. et al., "Increased potency of a novel D-beta-naphthylalanine-substituted antimicrobial peptide against fluconazole-resistant fungal pathogens," FEMS Yeast Research, 2009, 9(6):967-970.
Wang, J.; et al., "Automatic atom type and bond type perception in molecular mechanical calculations." J. Mol. Graphic. Model. 2006, 25, 247-260.
Wang, J.; et al., "Development and testing of a general AMBER force field." J. Comput. Chem. 2004, 25, 1157-1174.
Wedemeyer, W. J.; et al., "Proline cis-trans isomerization and protein folding." Biochemistry 2002, 41, 14637-14644.
Weissig, V., G. G. M. D'Souza, and V. P. Torchilin. "DQAsome/DNA complexes release DNA upon contact with isolated mouse liver mitochondria." Journal of controlled release 75.3 (2001): 401-408.
Wender, P. A. et al., "The design, synthesis, and evaluation of molecules that enable or enhance cellular uptake: Peptoid molecular transporters," Proc. Natl. Acad. Sci. U. S. A., Nov. 2000, 97(24):13003-13008.

(56) References Cited

OTHER PUBLICATIONS

Wells, James A., and Christopher L. McClendon. "Reaching for high-hanging fruit in drug discovery at protein-protein interfaces." Nature 450.7172 (2007): 1001.
White, Tina R., et al. "On-resin N-methylation of cyclic peptides for discovery of orally bioavailable scaffolds." Nature chemical biology 7.11 (2011): 810.
Wipf, Peter, et al. "Mitochondrial targeting of selective electron scavengers: Synthesis and biological analysis of hemigramicidin-TEMPO conjugates." Journal of the American Chemical Society 127.36 (2005): 12460-12461.
Wohr, T.; et al., "Pseudo-prolines as a solubilizing, structure-disrupting protection technique in peptide synthesis." J. Am. Chem. Soc. 1996, 118, 9218-9227.
Wolde, Michael, et al. "Targeting CAL as a negative regulator of ΔF508-CFTR cell-surface expression an rna interference and structure-based mutagenetic approach." Journal of Biological Chemistry 282.11 (2007): 8099-8109.
Wu, G. et al., "Structural basis of IAP recognition by Smac/DIABLO," Nature, Dec. 2000, 408(6815):1008-1012.
Wu, X., et al., "Inhibition of Ras-effector interactions by cyclic peptides." Med. Chem. Commun. 4, (2013): 378-382.
Wu et al., "Octa-guanidine morpholino restores dystrophin expression in cardiac and skeletal muscles and ameliorates pathology in dystrophic mdx mice." Molecular Therapy 17.5 (2009): 864-871.
Xie, L. et al., "Cellular Effects of Small Molecule PTP1B Inhibitors on Insulin Signaling," Biochemistry, 2003, 42(44):12792-12804.
Xu, L.H. et al. "Directed evolution of high-affinity antibody mimics using mRNA display." Chem. Biol. 9, (2002):933-942.
Yamada, Yuma, and Hideyoshi Harashima. "Delivery of bioactive molecules to the mitochondrial genome using a membrane-fusing, liposome-based carrier, DF-MITO-Porter." Biomaterials 33.5 (2012): 1589-1595.
Yamagishi, Y. et al. "Natural product-like macrocyclic N-methyl-peptide inhibitors against a ubiquitin ligase uncovered from a ribosome-expressed de novo library." Chem. Biol. 18, (2011):1562-1570.
Yin, H., Kanasty, R. L., Eltoukhy, A. A., Vegas, A. J., Dorkin, J. R., and Anderson, D. G. (2014) Non-viral vectors for gene-based therapy. Nat. Rev. Genet. 15, 541-555.
Yin, J. et al. "Genetically encoded short peptide tag for versatile protein labeling by Sfp phosphopantetheinyl transferase." Proc. Natl. Acad. Sci. USA 102 (2005): 15815-15820.
Yoo, J., Lee, D., Gujrati, V., Rejinold, N. S., Lekshmi, K. M., Uthaman, S., Jeong, C., Park, I.-K., Jon, S., and Kim, Y.-C. (2017) Bioreducible branched poly(modified nona-arginine) cell-penetrating peptide as a novel gene delivery platform. J. Controlled Release 246, 142-154.
Yu, H., "Therapeutic potential of VIVIT, a selective peptide inhibitor of nuclear factor of activated T cells, in cardiovascular disorders." Cardiovasc Drug Rev. 2007 Summer;25(2):175-87.
Yu, H. et al., "Selective modulation of nuclear factor of activated T-cell function in restenosis by a potent bipartite peptide inhibitor." Circulation research 110.2 (2012): 200-210.
Zabolotny, J. M. et al., "PTP1B regulates leptin signal transduction in vivo," Dev. Cell, Apr. 2002, 2(4):489-495.
Zhen-Dan, et al., Macrocyclization in the Design of Non-Phosphorus-Containing Grb2 SH2 Domain-Binding Ligands. J. Med. Chem., 2004, 47:2166.
Zhang, Z et al. GTP-State-Selective Cyclic Peptide Ligands of K Ras(G12D) Block Its Interaction with Rat ACS Central Science, vol. 6, No. 10, Oct. 28, 2020, doi: 10.1021/acscentso10c00514; pp. 1753-1761.
Zhang, Donna D., et al. "Distinct cysteine residues in Keap1 are required for Keap1-dependent ubiquitination of Nrf2 and for stabilization of Nrf2 by chemopreventive agents and oxidative stress." Molecular and cellular biology 23.22 (2003): 8137-8151.
Zhang, Meijuan, et al. "Emerging roles of Nrf2 and phase II antioxidant enzymes in neuroprotection." Progress in neurobiology 100 (2013): 30-47.
Zhang, Y. et al., Cyclic Peptidyl Inhibitors of Grb2 and Tensin SH2 Domains Identified from Combinatorial Libraries. J. Comb. Chem. 2008, 10:247.
Zhao, Bingchuan, et al. "A Thioether-Stabilized d-Proline-l-Proline-Induced β-Hairpin Peptide of Defensin Segment Increases Its Anti-Candida albicans Ability." ChemBioChem 17.15 (2016): 1416-1420.
Zhao, Kun, et al. "Enhanced activity of cyclic transporter sequences driven by phase behavior of peptide-lipid complexes." Soft Matter 8.24 (2012): 6430-6433.
Zhao, Kesheng, et al. "Cell-permeable peptide antioxidants targeted to inner mitochondrial membrane inhibit mitochondrial swelling, oxidative cell death, and reperfusion injury." Journal of Biological Chemistry 279.33 (2004): 34682-34690.
Zhao, Hui, et al. "Crosslinked aspartic acids as helix-nucleating templates." Angewandte Chemie 128.39 (2016): 12267-12272.
Zhou, H. et al. "Structure-based design of high-affinity macrocyclic peptidomimetics to block the menin-mixed lineage leukemia 1 (MLLI) protein-protein interaction." J. Med. Chem. (2013) 56, 1113-1123.
Zhou, X. Z. et al., The isomerase PIN1 controls numerous cancer-driving pathways and is a unique drug target. Nat. Rev. Cancer, 2016, 16:463.
Ziegler, A. et al., "Interaction of the protein transduction domain of HIV-1 TAT with heparan sulfate: binding mechanism and thermodynamic parameters," Biophys. J., Jan. 2004, 86(1):254-263.
Ziegler, A., "Thermodynamic studies and binding mechanisms of cell-penetrating peptides with lipids and glycosaminoglycans," Advanced Drug Delivery Reviews, Mar. 2008, 60(4-5):580-597. Epub Oct. 22, 2007.
International Preliminary Report on Patentability issued for Application No. PCT/US2017/062951 on Jun. 6, 2019.
International Search Report and Written Opinion. Issued by the International Searching Authority (US) in Application No. PCT/US2017/062951 on Apr. 30, 2018. 12 pages.
International Search Report and Written Opinion issued for Application No. PCT/US2017/060881 on Apr. 26, 2018.
International Preliminary Report on Patentability issued for Application No. PCT/US17/60881, dated May 23, 2019.
International Preliminary Report on Patentability issued for Application No. PCT/US2017/063020 dated Jun. 6, 2019.
International Search Report and Written Opinion issued for Application No. PCT/US2017/063020 dated May 4, 2018.
International Search Report and Written Opinion issued for Application No. PCT/US2019/031522, dated Sep. 27, 2019.
International Preliminary Report on Patentability issued for Application No. PCT/US2019/031522, dated Nov. 19, 2020.
International Search Report and Written Opinion issued for Application No. PCT/US2014/039332, dated May 23, 2014.
International Search Report and Written Opinion issued for Application No. PCT/US2014/039332, dated Dec. 3, 2014.
International Search Report and Written Opinion for International Application No. PCT/US2015/032043, mailed Jan. 14, 2016, 11 pages.
International Preliminary Report on Patentability for International Application No. PCT/US2015/032043, dated Nov. 22, 2016, 8 pages.
International Search Report and Written Opinion issued for Application No. PCT/US2017/062945, dated Feb. 16, 2018.
International Preliminary Report on Patentability issued for Application No. PCT/US2017/062945, dated Jun. 6, 2019.
International Search Report and Written Opinion issued in International Application No. PCT/US2015/47267, Dated Dec. 7, 2015.
International Preliminary Report on Patentability issued in International Application No. PCT/US2015/47267 dated Mar. 9, 2017.
International Search Report and Written Opinion issued for Application No. PCT/US2018/057894 dated Jan. 15, 2019, 10 pages.
International Preliminary Report on Patentability issued for Application No. PCT/US2018/057894 dated May 7, 2020.
International Search Report and Written Opinion issued by the International Searching Authority (ISA/US) in PCT Application No. PCT/US2019/015695 on Jul. 25, 2019, 14 pages.

(56) References Cited

OTHER PUBLICATIONS

International Preliminary Report on Patentability issued for Application No. PCT/US2019/015695, dated Aug. 13, 2020.
International Search Report and Written Opinion issued by the International Searching Authority (ISA/US) in PCT Application No. PCT/US20196/015697 on Jul. 19, 2019, 11 pages.
International Preliminary Report on Patentability issued for Application No. PCT/US20196/015697 dated Aug. 13, 2020, 7 pages.
International Search Report and Written Opinion issued by the International Searching Authority (ISA/US) in PCT Application No. PCT/US2019/030915 on Jul. 15, 2019, 8 pages.
International Preliminary Report on Patentability issued for Application No. PCT/US2019/030915, Nov. 19, 2020.
International Search Report and Written Opinion issued by the International Searching Authority (ISA/US) in PCT Application No. PCT/US2019/040335 on Nov. 6, 2019, 15 pages.
International Preliminary Report on Patentability issued for Application No. PCT/US2019/040335 dated Jan. 14, 2021.
International Search Report and Written Opinion issued by the International Searching Authority (ISA/US) in PCT Application No. PCT/US2020/048523 on Nov. 30, 2020, 9 pages.
International Preliminary Report on Patentability issued for Application No. PCT/US2020/048523 on Mar. 10, 2022.
International Search Report and Written Opinion issued in PCT Application No. PCT/US2020/067427 on Mar. 11, 2021, 3 pages.
Invitation to Pay Additional Fees issued in PCT Application No. PCT/US2020/067427 on Mar. 11, 2021, 3 pages.
International Preliminary Report on Patentability issued for Application No. PCT/US2020/067427 on Jul. 5, 2022.
International Search Report and Written Opinion for International Application No. PCT/US2022/034507 dated Jan. 25, 2023, 15 pages.
International Preliminary Report on Patentability issued for Application No. PCT/US2022/034507 dated Jan. 4, 2024, 9 pages.
International Search Report and Written Opinion for International Application No. PCT/US2022/17211 dated Jul. 7, 2022, 11 pages.
International Preliminary Report on Patentability issued for Application No. PCT/US2022/17211 dated Aug. 22, 2023, 7 pages.
Extended European Search Report issued for Application No. 15835788.9, dated Jun. 1, 2018.
Extended European Search Report issued Nov. 17, 2016 in European Application No. 14800563.
Communication pursuant to Article 94(3) EPC issued Jul. 13, 2017, in European Application No. 14800563.
Communication under Rule 71(3) EPC issued Dec. 14, 2017, in European Application No. 14800563.
Communication under Rule 71(3) EPC issued May 18, 2018, in European Application No. 14800563.
Decision to Grant a European Patent pursuant to Art 97(1) EPC issued Oct. 5, 2018, in European Application No. 14800563.
Extended European Search Report issued by the European Patent Office in European Application No. 18870802.8 on Jun. 22, 2021, 8 pages.
English translation of Office Action for Taiwanese Application No. 106140322 dated Jan. 6, 2022.
English translation of Office Action for Taiwanese Application No. 106140322 dated Aug. 4, 2022, 10 pages.
English translation of Office Action for Taiwanese Application No. 106140322 dated Feb. 5, 2024.
English translation of Office Action for Taiwanese Application No. 106138809 dated Nov. 5, 2021.
Extended European Search Report issued in EP 17870556.2, mailed Sep. 8, 2020.
Communication pursuant to Article 94(3) EPC for European Application No. 17870556.2 dated Sep. 1, 2022, 5 pages.
Extended European Search Report issued for Application No. 15796259.8, dated Jan. 22, 2018, 6 pages.
Communication Pursuant to Rule 164(1) EPC, issued for U.S. Appl. No. 17/874,485, dated Feb. 3, 2021.
Partial Supplementary Search Report issued for European Application No. 19743190 dated Jan. 19, 2022.
European Search Report issued for EP Application No. 19743190 dated Apr. 22, 2022.
Extended European Search Report for EP Application No. 19799961.8 dated Feb. 2, 2022.
Office Action for EP Application No. 17874485.0 dated May 10, 2021.
Office Action for EP Application No. 17874485.0 dated Nov. 16, 2022, 5 pages.
Extended European Search Report for EP Application No. 18870802.8 dated Jun. 22, 2021, 8 pages.
Extended European Search Report issued for European Application No. 19743545.6 dated Dec. 13, 2021.
Extended European Search Report issued May 18, 2022, received in connection with corresponding EP Patent Application No. 19796864.7.
Communication pursuant to Rule 164(1) EPC for Application No. 19831072.4 dated Jul. 29, 2022, 13 pages.
Extended European Search Report for Application No. 19831072.4 dated Nov. 3, 2022, 13 pages.
Extended European Search Report for EP Application 20857054.9 dated Sep. 7, 2023, 13 pages.
English translation of Office Action for Chinese Application No. 201780069098.8 dated Nov. 28, 2022, 9 pages.
English translation of Office Action for Chinese Application No. 20178006909887 dated Nov. 28, 2022, 15 pages.
English translation of the Office Action for Chinese Application No. 201780069098.8 dated Aug. 3, 2023.
English translation of Office Action for Chinese Application No. 201880070271.0 dated Mar. 6, 2023, 18 pages.
English translation of Search Report for Chinese Application No. 201880070271.0 dated Mar. 6, 2023, 3 pages.
Grant Notification for Chinese Application No. 201780069098.8 dated Oct. 25, 2023.
English translation of Office Action for Japanese Application No. 2019-524067 dated Oct. 5, 2021.
English translation of Office Action for Japanese Application No. 2019-524067 dated May 10, 2022.
English translation of Decision to Grant for Japanese Application No. 2019-524067 dated Oct. 11, 2022.
Japanese Application Serial No. 2020-543254, Notification of Reasons for Refusal filed Sep. 13, 2022, 3 pages.
English translation of Decision of Refusal for Japanese Application No. 2020 543254 dated Mar. 14, 2023, 6 pages.
English translation of Office Action for Japanese Application No. 2022-179784 dated Nov. 7, 2023, 5 pages.
Restriction Requirement issued in U.S. Appl. No. 14/893,203 dated Jun. 20, 2016.
Office Action issued in U.S. Appl. No. 14/893,203 dated Dec. 6, 2016.
Notice of Allowance issued in U.S. Appl. No. 14/893,203 dated May 9, 2017.
Restriction Requirement issued in U.S. Appl. No. 15/672,617 mailed Oct. 3, 2018.
Office Action issued in U.S. Appl. No. 15/672,617 dated Mar. 1, 2019.
Notice of Allowance issued in U.S. Appl. No. 15/672,617 dated Jul. 22, 2019.
Restriction Requirement for U.S. Appl. No. 15/506,877 dated Nov. 15, 2017.
Office Action for U.S. Appl. No. 15/506,877 dated Apr. 6, 2018.
Office Action for U.S. Appl. No. 15/506,877 dated Nov. 2, 2018.
Office Action for U.S. Appl. No. 15/506,877 dated Apr. 19, 2019.
Notice of Allowance for U.S. Appl. No. 15/506,877 dated Jun. 25, 2019.
Restriction Requirement for U.S. Appl. No. 17/136,578 dated Dec. 16, 2022, 8 pages.
Office Action for U.S. Appl. No. 17/136,578 dated Mar. 15, 2023, 13 pages.
Notice of Allowance for U.S. Appl. No. 17/136,578 dated Aug. 25, 2023, 16 pages.

(56) References Cited

OTHER PUBLICATIONS

Restriction Requirement for U.S. Appl. No. 16/348,706 dated May 14, 2020.
Office Action for U.S. Appl. No. 16/348,706 dated Mar. 1, 2021.
Notice of Allowance for U.S. Appl. No. 16/348,706 dated Aug. 30, 2021.
Notice of Allowance for U.S. Appl. No. 16/348,706 dated Apr. 15, 2022.
Office Action issued in U.S. Appl. No. 16/348,706, dated Nov. 16, 2020.
Restriction Requirement issued in U.S. Appl. No. 16/462,920, mailed Apr. 13, 2020.
Office Action issued in U.S. Appl. No. 16/462,920, mailed Aug. 18, 2020.
Office Action issued in U.S. Appl. No. 16/462,920, mailed Feb. 16, 2021.
Office Action issued in U.S. Appl. No. 16/462,920, mailed Jul. 6, 2021.
Notice of Allowance for U.S. Appl. No. 16/462,920 dated Feb. 2, 2022.
Restriction Requirement issued for U.S. Appl. No. 16/462,922 dated Dec. 14, 2020.
Office Action issued for U.S. Appl. No. 16/462,922 dated Sep. 13, 2021, 21 pages.
Office Action for U.S. Appl. No. 16/462,922 dated Jan. 31, 2022.
Office Action for U.S. Appl. No. 16/462,922 dated May 10, 2022.
Office Action for U.S. Appl. No. 16/462,922 dated Dec. 22, 2022, 11 pages.
Advisory Action for U.S. Appl. No. 16/462,922 dated Mar. 30, 2023.
Office Action for U.S. Appl. No. 16/462,922 dated Jul. 7, 2023.
Restriction Requirement for U.S. Appl. No. 16/753,681 dated Nov. 18, 2020.
Office Action for U.S. Appl. No. 16/753,681 dated Mar. 10, 2021.
Notice of Allowance for U.S. Appl. No. 16/753,681 dated Feb. 16, 2022.
Office Action for U.S. Appl. No. 17/750,966 dated Oct. 24, 2022.
Notice of Allowance for U.S. Appl. No. 17/750,966 dated Mar. 2, 2023.
Office Action for U.S. Appl. No. 16/759,600 dated Mar. 29, 2021.
Office Action for U.S. Appl. No. 16/759,600 dated Nov. 12, 2021.
Notice of Allowance for U.S. Appl. No. 16/759,600 dated May 6, 2022.
Notice of Allowance for U.S. Appl. No. 16/759,600 dated Oct. 28, 2022.
Restriction Requirement for U.S. Appl. No. 17/817,836 dated Sep. 7, 2023.
Non-Final Office Action for U.S. Appl. No. 17/817,836 dated Jan. 18, 2024.
Restriction Requirement for U.S. Appl. No. 16/965,713 dated Jul. 13, 2021.
Office Action for U.S. Appl. No. 16/965,713 dated Nov. 22, 2021.
Office Action for U.S. Appl. No. 16/965,713 dated May 26, 2022.
Office Action for U.S. Appl. No. 16/965,713 dated Sep. 29, 2022.
Office Action for U.S. Appl. No. 16/965,713 dated Aug. 11, 2022.
Office Action for U.S. Appl. No. 16/965,713 dated Mar. 23, 2023.
Notice of Allowance for U.S. Appl. No. 16/965,713 dated Jun. 14, 2023.
Restriction Requirement for U.S. Appl. No. 16/965,718 dated Oct. 7, 2021.
Office Action for U.S. Appl. No. 16/965,718 dated Jan. 27, 2022.
Notice of Allowance for U.S. Appl. No. 16/965,718 dated May 17, 2022.
Notice of Allowance for U.S. Appl. No. 16/965,718 dated Oct. 5, 2022.
Restriction Requirement for U.S. Appl. No. 17/257,224 dated Sep. 27, 2023.
Non-Final Office Action for U.S. Appl. No. 17/257,224 dated Dec. 22, 2023.
Restriction Requirement for U.S. Appl. No. 17/052,935 dated Feb. 18, 2022.
Office Action for U.S. Appl. No. 17/052,935 dated Apr. 14, 2022.
Office Action for U.S. Appl. No. 17/052,935 dated Dec. 6, 2022.
Advisory Action for U.S. Appl. No. 17/052,935 dated Feb. 1, 2023.
Office Action for U.S. Appl. No. 17/052,935 dated Mar. 16, 2023.
Notice of Allowance for U.S. Appl. No. 17/052,935 dated Jul. 6, 2023.
Restriction Requirement for U.S. Appl. No. 17/053,684 dated Aug. 6, 2021, 10 pages.
Office Action for U.S. Appl. No. 17/053,684 dated Apr. 1, 2022.
Office Action for U.S. Appl. No. 17/053,684 dated Aug. 5, 2022.
Advisory Action for U.S. Appl. No. 17/053,684 dated Nov. 2, 2022, 3 pages.
Office Action for U.S. Appl. No. 17/053,684 dated Jan. 20, 2023, 10 pages.
Office Action for U.S. Appl. No. 17/053,684 dated May 11, 2023, 7 pages.
Office Action for U.S. Appl. No. 17/053,684 dated Sep. 8, 2023.
Notice of Allowance for U.S. Appl. No. 17/053,684 dated Mar. 18, 2024.
Restriction Requirement for U.S. Appl. No. 17/538,330 dated Oct. 14, 2022, 8 pages.
Office Action for U.S. Appl. No. 17/538,330 dated Mar. 16, 2023, 11 pages.
Notice of Allowance for U.S. Appl. No. 17/538,330 dated Sep. 7, 2023, 11 pages.
Office Action for U.S. Appl. No. 16/462,914 dated Apr. 17, 2020.
Notice of Allowance for U.S. Appl. No. 16/462,914 dated Sep. 29, 2020.
Office Action for Canadian Application No. 3,043,464 dated Mar. 6, 2024.

BICYCLIC PEPTIDYL INHIBITORS

CROSS-REFERENCE TO RELATED APPLICATIONS

This application is a continuation of U.S. application Ser. No. 17/750,966, filed May 23, 2022, which is a divisional of U.S. application Ser. No. 16/753,681, filed Apr. 3, 2020, which is a national stage application filed under 35 U.S.C. § 371 of PCT/US2018/054345, filed Oct. 4, 2018, which claims the benefit of U.S. Provisional Application No. 62/568,221, filed on Oct. 4, 2017, which is incorporated by reference herein in its entirety.

ACKNOWLEDGMENT OF GOVERNMENT SUPPORT

This invention was made with government support under GM110208, GM122459, and GM008512 awarded by the National Institutes of Health. The government has certain rights in the invention.

DESCRIPTION OF THE TEXT FILE SUBMITTED ELECTRONICALLY

A sequence listing conforming to the rules of WIPO Standard ST.26 is hereby incorporated by reference. Said Sequence Listing has been filed as an electronic document via Patent Center encoded as XML in UTF-8 text. The electronic document, created on Nov. 6, 2024, is entitled "10336-371US3_ST26.xml", and is 317,727 bytes in size.

BACKGROUND

Protein-protein interaction (PPI) is a fundamental aspect of biological processes, and such interactions mediate numerous disease. However, intracellular PPIs are challenging targets for current drug modalities (i.e., small molecules and biologics) and represent the largest untapped opportunity for therapeutic development.

NF-κB essential modulator (NEMO) s a regulatory protein of the canonical NF-κB signaling pathway. During canonical NF-κB signaling, receptor activation at the cell surface results in the formation of an active inhibitor of κB (IκB)-kinase (IKK) complex consisting of IKKα, IKKβ, and NEMO (which is also called IKKγ). Aberrant activation of the canonical pathway is implicated in many inflammatory and autoimmune diseases, as well as cancer.

The NEMO-IKK complex has been a challenging target for drug discovery. Small molecule inhibitors do not display high enough potency against the NEMO-IKK interaction to be a viable therapeutic strategy. Therefore, there is still need for developing potent peptidyl inhibitors of the NEMO-IKK interaction as a novel class of anti-inflammatory and anti-cancer drugs.

BRIEF DESCRIPTIONS OF THE FIGURES

FIG. 1 depicts structures of the bicyclic peptide library, hit No. 4, and peptide 7. Amino acid residues in peptide 7 are numbered from N- to C-terminus. The CPP sequence is shown in red, whereas the residues modified during optimization are shown in blue color. B, β-alanine; CPP, cell-penetrating peptide; Hmb, hydroxylmethylbenzoyl; Pra, propargylglycine; Δ, L-2,3-diaminopropionic acid (Dap).

Figure 2A:
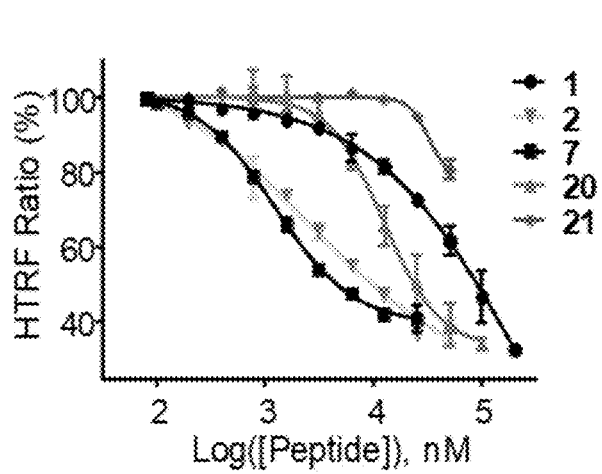
Figure 2B:
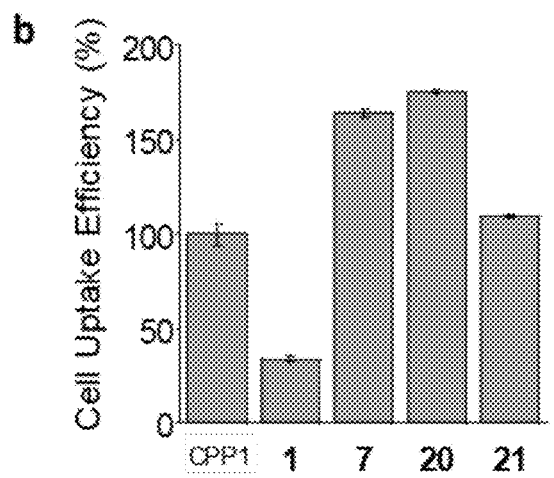
Figure 2C:
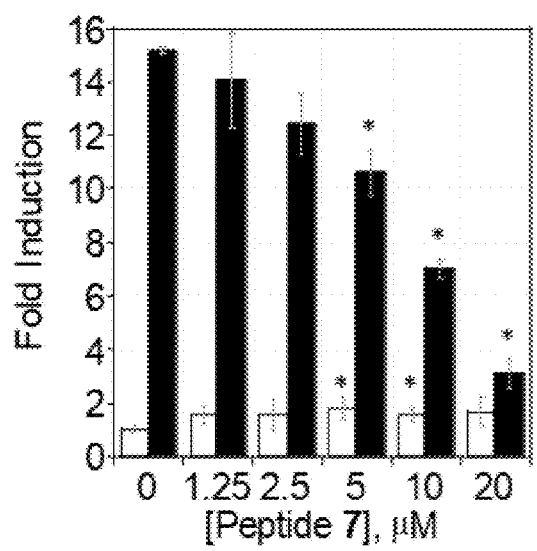
Figure 2D:
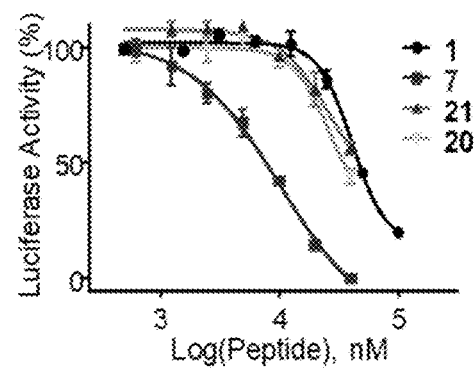
Figure 2E:
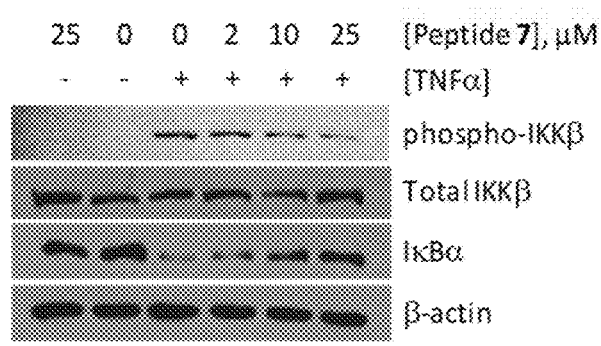

FIGS. 2A-2E illustrate the inhibition of the NEMO-IKK$_{α/β}$ interaction and NF-κB signaling by peptide 7 and control peptides. FIG. 2A shows the inhibition of the NEMO-IKKβ interaction as monitored by the HTRF assay. FIG. 2B shows the cellular uptake efficiency of FITC-labeled peptides into HeLa cells as determined by flow cytometry. All values are relative to that of CPP1 (100%). FIG. 2C shows differential effects of pep-tide 7 on the basal (open bars) and TNFα-induced NF-κB activation (closed bars) in HEK293(Luc) cells. *, p<0.001 using Student's t-test. FIG. 2D compares peptides 1, 7, 20, and 21 for inhibition of TNFα-induced luciferase activity in HEK293 (Luc) cells. FIG. 2E is a western blot showing the effect of peptide 7 on IκBα and IKKβ levels in HT29 colon cancer cells in the absence and presence of TNFα.

Figures 3A, 3B, 3C:
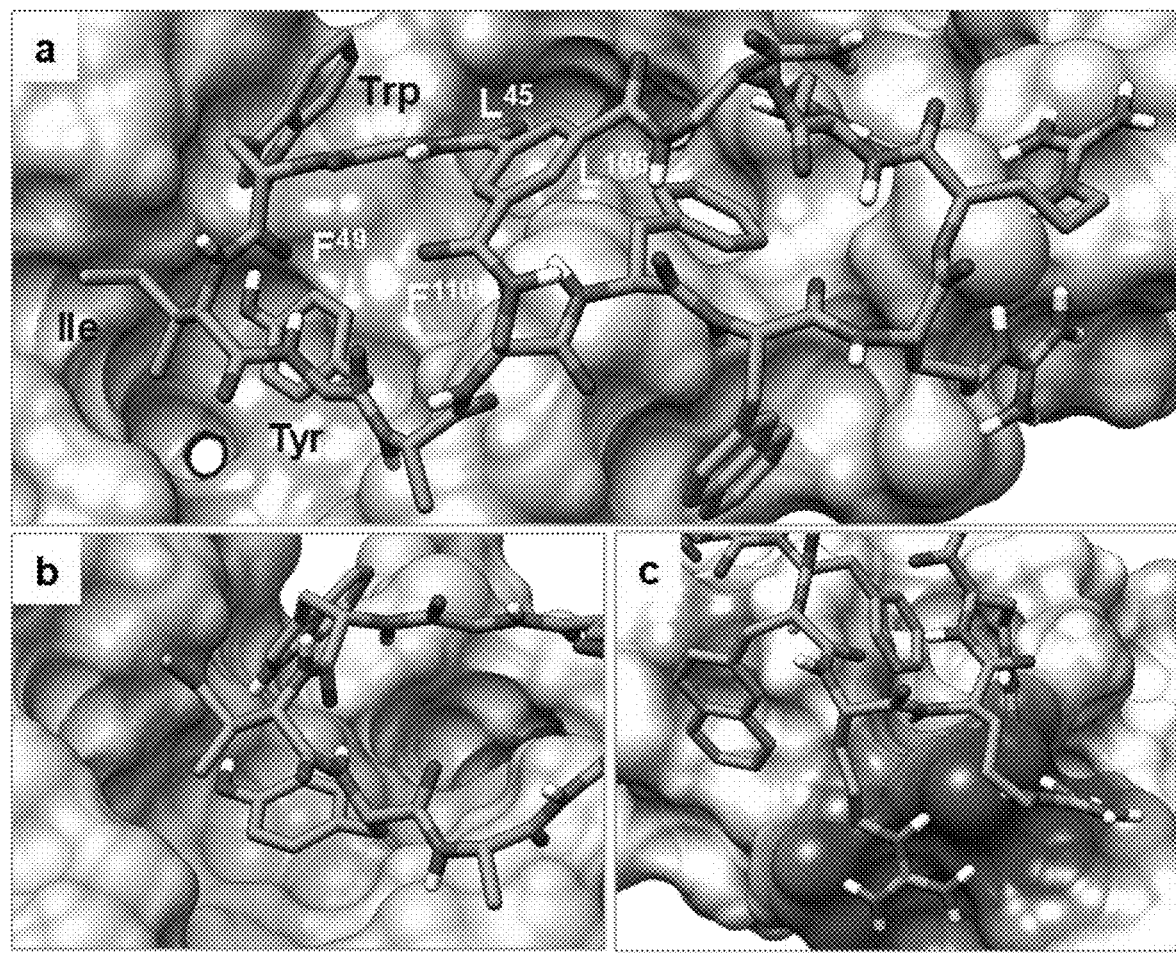

FIGS. 3A-3C show in silico model of the NEMO-peptide 7 complex. FIG. 3A shows the overall complex between peptide 7 (shown as green sticks) and NEMO (PDBID: 3BRT; shown as van der Waals surface) with residues critical for the NEMO-IKKβ interaction shaded pink. FIG. 3B is a close-up of the interaction between the A ring (in green) and NEMO including the insertion of Tyr-4 into a hydrophobic pocket. FIG. 3C shows a zoom-in view of the charge-charge interactions between the three arginine residues of peptide 7 and acidic residues on NEMO. Basic and acidic residues of NEMO are shown in blue and red, respectively.

Figure 4A:
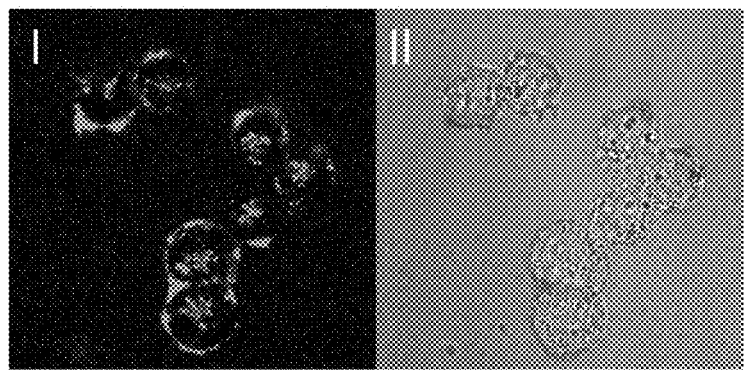
Figure 4B:
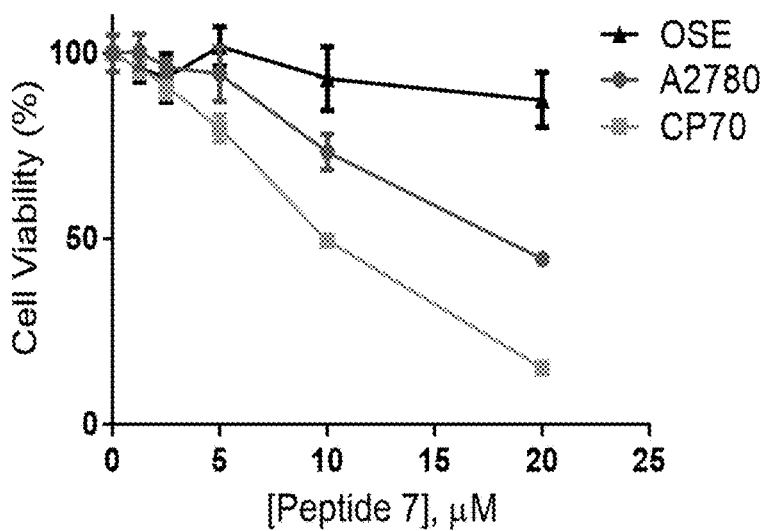
Figure 4C:
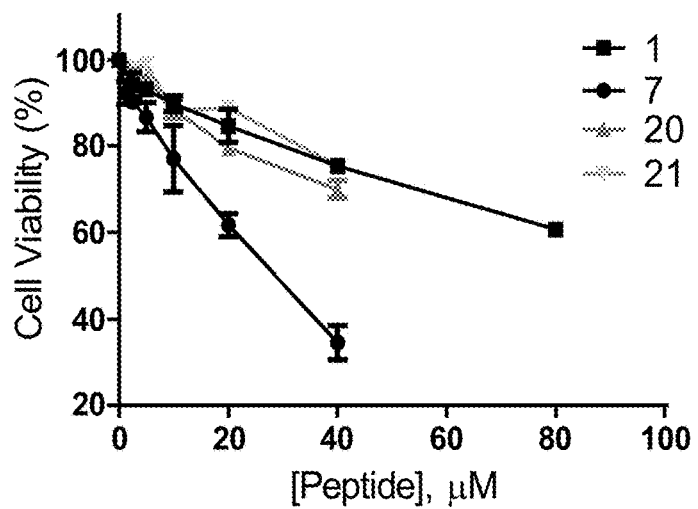
Figure 4D:
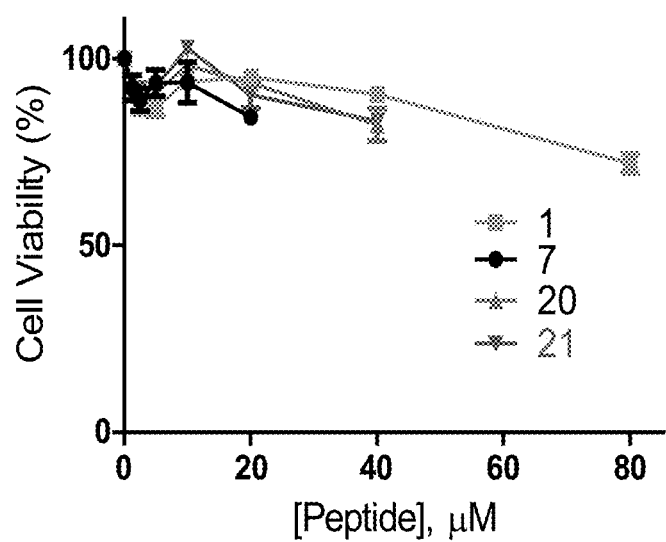

FIGS. 4A-4D show the anticancer activity of peptide 7. FIG. 4A shows live-cell confocal microscopic image of A2780 ovarian cancer cells after 2-hour treatment with 5 μM FITC-peptide 7. I, FITC fluorescence; II, DIC. FIG. 4B shows viability of ovarian cancer cells (A2780 and CP70) and non-cancerous ovarian cells (OSE) in the presence of increasing concentrations of peptide 7, as determined by the methylene blue assay. FIG. 4C compares peptide 7 and control peptides for their effect on the viability of A2780 cells. FIG. 4D shows the effect of peptide 7 and control peptides on non-cancerous OSE cells. Viability tests in panel (c) and (d) were performed by the MTT assay.

DETAILED DESCRIPTION

Bicyclic Polypeptides

Disclosed herein, in various embodiments, are bicyclic polypeptides. The bicyclic polypeptides have a first polypeptide sequence which forms a first ring (referred to herein as the "A ring"), and a second polypeptide sequence which forms a second ring (referred to herein as the "B ring"). In some embodiments, the bicyclic polypeptides disclosed herein penetrate the cell membrane and are capable of inhibiting intracellular protein-protein interactions.

In some embodiments, the bicyclic polypeptides comprise a first sequence which is capable of inhibiting a protein-protein interaction (referred to herein as the "Xm" sequence), and a second sequence which is capable of penetrating a cell membrane (referred to herein as the "CPP" sequence). In various embodiments, the Xm sequence may include amino acids which influence or participate in cellular penetration. Similarly, in embodiments, the CPP sequence may include amino acids which participate in inhibiting a protein-protein interaction.

In various embodiments, the disclosure provides for bicyclic polypeptides according to Formula 1A or 1B:

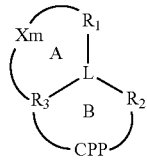
(1A)

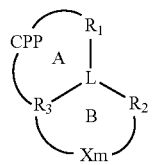
(1B)

wherein:
CPP is a cell-penetrating peptide sequence;
Xm is a peptide sequence that binds to a NF-κB essential modulator (NEMO) protein;
L is a linker moiety; and
each of $R_1$, $R_2$, and $R_3$ are, independently, a bonding moiety,
wherein the bonding moiety is formed when Xm, CPP, or a combination thereof, covalently bind to L to form the bicyclic polypeptide.

In various embodiments, the disclosure provides for bicyclic polypeptides according to Formula 1C or 1D:

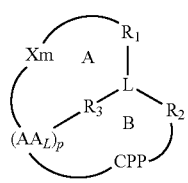
(1C)

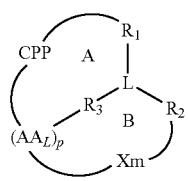
(1D)

wherein:
CPP is a cell-penetrating peptide sequence;
Xm is a peptide sequence that binds to a NF-κB essential modulator (NEMO) protein;
$AA_L$ at each instance is an amino acid;
p is selected from a number from 0 to 3 (e.g., 0, 1, 2, or 3);
L is a linker moiety; and
each of $R_1$, $R_2$, and $R_3$ are independently, a bonding moiety,
wherein the bonding moiety is formed when Xm, CPP, $AA_L$ or a combination thereof, covalently bind to L to form the bicyclic polypeptide.

Non-limiting examples of bicyclic polypeptides of the present disclosure are provided in Example 1.

Xm Sequence

As discussed above, the bicyclic polypeptides disclosed herein comprise a sequence which is capable of binding to a NEMO protein ("Xm"). In further embodiments, the Xm sequence binds the IKKα/β-binding domain on NEMO. In such embodiments, the Xm sequence can be an appropriate combination of amino acids that binds to IKKα/β-binding domain on NEMO Suitable amino acid sequences in the Xm sequence for use in the bicyclic polypeptides and methods described herein can include naturally occurring sequences, modified sequences, and synthetic sequences. In embodiments, the total number of amino acids in the Xm may be in the range of from 3 to about 20 amino acids, e.g., about 4, about 5, about 6, about 7, about 8, about 9, about 10, about 11, about 12, about 13, about 14, about 15, about 16, about 17, about 18, and about 19 amino acids, inclusive of all ranges and subranges therebetween. In some embodiments, the Xm disclosed herein comprise about 4 to about to about 13 amino acids. In particular embodiments, the Xm disclosed herein comprise about 4 to about 10 amino acids, or about 4 to about 8 amino acids. In other particular embodiments, the Xm disclosed herein comprise about 6 amino acids.

Each amino acid in the Xm may be a natural or non-natural amino acid. The term "non-natural amino acid" refers to an organic compound that is a congener of a natural amino acid in that it has a structure similar to a natural amino acid so that it mimics the structure and reactivity of a natural amino acid. The non-natural amino acid can be a modified amino acid, and/or amino acid analog, that is not one of the 20 common naturally occurring amino acids or the rare natural amino acids selenocysteine or pyrrolysine. Non-natural amino acids can also be the D-isomer of the natural amino acids. Examples of suitable amino acids include, but are not limited to, alanine, allosoleucine, arginine, asparagine, aspartic acid, cysteine, glutamine, glutamic acid, glycine, histidine, isoleucine, leucine, lysine, methionine, napthylalanine, phenylalanine, proline, pyroglutamic acid, serine, threonine, tryptophan, tyrosine, valine, a derivative, or combinations thereof. These, and others, are listed in the Table 1 along with their abbreviations used herein.

TABLE 1

Amino Acid Abbreviations

| Amino Acid | Abbreviations* L-amino acid | Abbreviations* D-amino acid |
|---|---|---|
| alanine | Ala (A) | ala (a) |
| allosoleucine | AIle | aile |
| arginine | Arg (R) | arg (r) |
| asparagine | Asn (N) | asn (n) |
| aspartic acid | Asp (D) | asp (d) |
| cysteine | Cys (C) | cys (c) |
| cyclohexylalanine | Cha | cha |
| 2,3-diaminopropionic acid | Dap | dap |
| 4-fluorophenylalanine | Fpa (Σ) | fpa |
| glutamic acid | Glu (E) | glu (e) |
| glutamine | Gln (Q) | gln (q) |
| glycine | Gly (G) | gly (g) |
| histidine | His (H) | his (h) |
| homoproline (aka pipecolic acid) | Pip (Θ) | pip (Θ) |
| isoleucine | Ile (I) | ile (i) |
| leucine | Leu (L) | leu (l) |
| lysine | Lys (K) | lys (k) |
| methionine | Met (M) | met (m) |
| napthylalanine | Nal (Φ) | nal (φ) |
| norleucine | Nle (Ω) | nle |
| phenylalanine | Phe (F) | phe (F) |

TABLE 1-continued

Amino Acid Abbreviations

| Amino Acid | Abbreviations* L-amino acid | Abbreviations* D-amino acid |
|---|---|---|
| phenylglycine | Phg (Ψ) | phg |
| 4-(phosphonodifluoromethyl) phenylalanine | F$_2$Pmp (Λ) | f$_2$pmp |
| proline | Pro (P) | pro (p) |
| sarcosine | Sar (Ξ) | sar |
| selenocysteine | Sec (U) | sec (u) |
| serine | Ser (S) | ser (s) |
| threonine | Thr (T) | thr (y) |
| tyrosine | Tyr (Y) | tyr (y) |
| tryptophan | Trp (W) | trp (w) |
| valine | Val (V) | val (v) |

*single letter abbreviations: when shown in capital letters herein it indicates the L-amino acid form, when shown in lower case herein it indicates the D-amino acid form.

In particular embodiments, the Xm sequence includes one or more amino acids selected from G, g, W, w, I, i, Y, y, A, and a. In certain embodiments Xm is a 3-7 amino acid sequence comprising at least one W or w. In certain embodiments Xm is a 3-7 amino acid sequence comprising at least one I or i. In certain embodiments Xm is a 3-7 amino acid sequence comprising a sequence selected from WI, IW, Wi, iW, wI, Iw, iw, wi. In certain embodiments Xm is a 3-7 amino acid sequence comprising WI. In further embodiments, the Xm is a 4-7 amino acid sequence comprising a sequence selected from the group consisting of: GWIY (SEQ ID NO:1); GWIYA (SEQ ID NO:2); GWIYa (SEQ ID NO:50); AGWIY (SEQ ID NO:3); aGWIY (SEQ ID NO:51); AWIYA (SEQ ID NO:4); GAIYA (SEQ ID NO:5); GWAYA (SEQ ID NO:6); GWIAA (SEQ ID NO:7); GWIYA (SEQ ID NO:8); GAIAA (SEQ ID NO:9); and GAAAA (SEQ ID NO:10), and the inverse of such sequences (SEQ ID NOs: 52-63).

Cell-Penetrating Peptide Sequence

As discussed above, the bicyclic polypeptides disclosed herein comprise a cell penetrating peptide sequence ("CPP"). The CPP includes any amino sequence which facilitates cellular uptake of the polypeptide conjugates disclosed herein.

In some embodiments, the CPPs may include any combination of at least two arginines and at least two hydrophobic amino acids.

In some embodiments, the CPP used in polypeptide conjugates described herein has a structure comprising Formula 2:

$$(AA_u)_m\text{-}AA_1\text{-}AA_2\text{-}AA_3\text{-}AA_4\text{-}(AA_z)_n \qquad 2$$

wherein:
  each of $AA_1$, $AA_2$, $AA_3$, and $AA_4$, are independently selected from a D or L amino acid,
  each of $AA_u$ and $AA_z$, at each instance and when present, are independently selected from a D or L amino acid, and
  m and n are independently selected from a number from 0 to 6; and wherein:
  at least two of $AA_u$, when present, $AA_1$, $AA_2$, $AA_3$, $AA_4$, and $AA_z$, when present, are independently arginine, and
  at least two of $AA_u$, when present, $AA_1$, $AA_2$, $AA_3$, $AA_4$, and $AA_z$, when present, are independently a hydrophobic amino acid.

(i) In some embodiments, each hydrophobic amino acid is independently selected from is independently selected from glycine, alanine, valine, leucine, isoleucine, methionine, phenylalanine, tryptophan, proline, naphthylalanine, phenylglycine, homophenylalanine, tyrosine, cyclohexylalanine, piperidine-2-carboxylic acid, cyclohexylalanine, norleucine, 3-(3-benzothienyl)-alanine, 3-(2-quinolyl)-alanine, O-benzylserine, 3-(4-(benzyloxy)phenyl)-alanine, S-(4-methylbenzyl)cysteine, N-(naphthalen-2-yl)glutamine, 3-(1,1'-biphenyl-4-yl)-alanine, tert-leucine, or nicotinoyl lysine, each of which is optionally substituted with one or more substituents. The structures of certain of these non-natural aromatic hydrophobic amino acids (prior to incorporation into the peptides disclosed herein) are provided below. In particular embodiments, each hydrophobic amino acid is independently a hydrophobic aromatic amino acid. In some embodiments, the aromatic hydrophobic amino acid is naphthylalanine, 3-(3-benzothienyl)-alanine, phenylglycine, homophenylalanine, phenylalanine, tryptophan, or tyrosine, each of which is optionally substituted with one or more substituents.

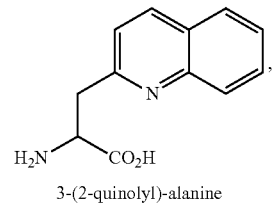

3-(2-quinolyl)-alanine

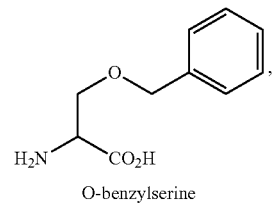

O-benzylserine

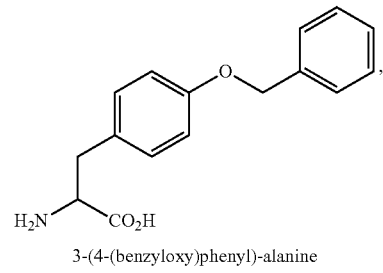

3-(4-(benzyloxy)phenyl)-alanine

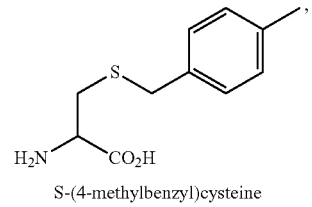

S-(4-methylbenzyl)cysteine

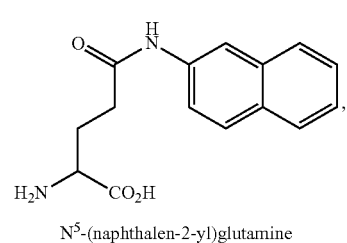

N$^5$-(naphthalen-2-yl)glutamine

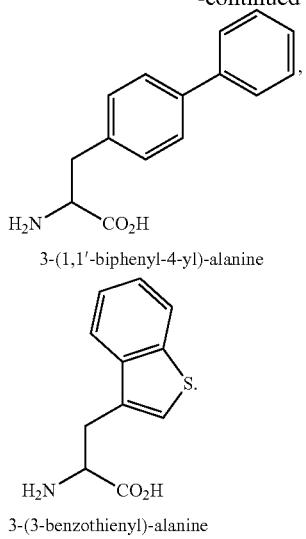

3-(1,1'-biphenyl-4-yl)-alanine 3-(3-benzothienyl)-alanine

In particular embodiments, the hydrophobic amino acid is piperidine-2-carboxylic acid, naphthylalanine, tryptophan, or phenylalanine, each of which is optionally substituted with one or more substituents.

The optional substituent can be any atom or group which does not significantly reduce the cytosolic delivery efficiency of the CPP, e.g., a substituent that does not reduce relative cytosolic delivery efficiency to less than that of c(FΦRRRRQ) (SEQ ID NO: 65). In some embodiments, the optional substituent can be a hydrophobic substituent or a hydrophilic substituent. In certain embodiments, the optional substituent is a hydrophobic substituent. In some embodiments, the substituent increases the solvent-accessible surface area (as defined herein) of the hydrophobic amino acid. In some embodiments, the substituent can be a halogen, alkyl, alkenyl, alkynyl, cycloalkyl, cycloalkenyl, cycloalkynyl, heterocyclyl, aryl, heteroaryl, alkoxy, aryloxy, acyl, alkylcarbamoyl, alkylcarboxamidyl, alkoxycarbonyl, alkylthio, or arylthio. In some embodiments, the substituent is a halogen.

Amino acids having higher hydrophobicity values can be selected to improve cytosolic delivery efficiency of a CPP relative to amino acids having a lower hydrophobicity value. In some embodiments, each hydrophobic amino acid independently has a hydrophobicity value which is greater than that of glycine. In other embodiments, each hydrophobic amino acid independently is a hydrophobic amino acid having a hydrophobicity value which is greater than that of alanine. In still other embodiments, each hydrophobic amino acid independently has a hydrophobicity value which is greater or equal to phenylalanine. Hydrophobicity may be measured using hydrophobicity scales known in the art. Table 2 below lists hydrophobicity values for various amino acids as reported by Eisenberg and Weiss (Proc. Natl. Acad. Sci. U.S.A. 1984; 81(1):140-144), Engleman, et al. (Ann. Rev. of Biophys. Biophys. Chem. 1986; 1986(15):321-53), Kyte and Doolittle (J. Mol. Biol. 1982; 157(1):105-132), Hoop and Woods (Proc. Natl. Acad. Sci. U.S.A. 1981; 78(6):3824-3828), and Janin (Nature. 1979; 277(5696):491-492), the entirety of each of which is herein incorporated by reference in its entirety. In particular embodiments, hydrophobicity is measured using the hydrophobicity scale reported in Engleman, et al.

TABLE 2

| Amino Acid | Group | Eisenberg and Weiss | Engleman et al. | Kyrie and Doolittle | Hoop and Woods | Janin |
|---|---|---|---|---|---|---|
| Ile | Nonpolar | 0.73 | 3.1 | 4.5 | −1.8 | 0.7 |
| Phe | Nonpolar | 0.61 | 3.7 | 2.8 | −2.5 | 0.5 |
| Val | Nonpolar | 0.54 | 2.6 | 4.2 | −1.5 | 0.6 |
| Leu | Nonpolar | 0.53 | 2.8 | 3.8 | −1.8 | 0.5 |
| Trp | Nonpolar | 0.37 | 1.9 | −0.9 | −3.4 | 0.3 |
| Met | Nonpolar | 0.26 | 3.4 | 1.9 | −1.3 | 0.4 |
| Ala | Nonpolar | 0.25 | 1.6 | 1.8 | −0.5 | 0.3 |
| Gly | Nonpolar | 0.16 | 1.0 | −0.4 | 0.0 | 0.3 |
| Cys | Unch/Polar | 0.04 | 2.0 | 2.5 | −1.0 | 0.9 |
| Tyr | Unch/Polar | 0.02 | −0.7 | −1.3 | −2.3 | −0.4 |
| Pro | Nonpolar | −0.07 | −0.2 | −1.6 | 0.0 | −0.3 |
| Thr | Unch/Polar | −0.18 | 1.2 | −0.7 | −0.4 | −0.2 |
| Ser | Unch/Polar | −0.26 | 0.6 | −0.8 | 0.3 | −0.1 |
| His | Charged | −0.40 | −3.0 | −3.2 | −0.5 | −0.1 |
| Glu | Charged | −0.62 | −8.2 | −3.5 | 3.0 | −0.7 |
| Asn | Unch/Polar | −0.64 | −4.8 | −3.5 | 0.2 | −0.5 |
| Gln | Unch/Polar | −0.69 | −4.1 | −3.5 | 0.2 | −0.7 |
| Asp | Charged | −0.72 | −9.2 | −3.5 | 3.0 | −0.6 |
| Lys | Charged | −1.10 | −8.8 | −3.9 | 3.0 | −1.8 |
| Arg | Charged | −1.80 | −12.3 | −4.5 | 3.0 | −1.4 |

The chirality of the amino acids can be selected to improve cytosolic uptake efficiency. In some embodiments, at least two of the amino acids have the opposite chirality. In some embodiments, the at least two amino acids having the opposite chirality can be adjacent to each other. In some embodiments, at least three amino acids have alternating stereochemistry relative to each other. In some embodiments, the at least three amino acids having the alternating chirality relative to each other can be adjacent to each other. In some embodiments, at least two of the amino acids have the same chirality. In some embodiments, the at least two amino acids having the same chirality can be adjacent to each other. In some embodiments, at least two amino acids have the same chirality and at least two amino acids have the opposite chirality. In some embodiments, the at least two amino acids having the opposite chirality can be adjacent to the at least two amino acids having the same chirality. Accordingly, in some embodiments, adjacent amino acids in the CPP can have any of the following sequences: D-L; L-D; D-L-L-D; L-D-D-L; L-D-L-L-D; D-L-D-D-L; D-L-L-D-L; or L-D-D-L-D.

In some embodiments, an arginine is adjacent to a hydrophobic amino acid. In some embodiments, the arginine has the same chirality as the hydrophobic amino acid. In some embodiments, at least two arginines are adjacent to each other. In still other embodiments, three arginines are adjacent to each other. In some embodiments, at least two hydrophobic amino acids are adjacent to each other. In other embodiments, at least three hydrophobic amino acids are adjacent to each other. In other embodiments, the CPPs described herein comprise at least two consecutive hydrophobic amino acids and at least two consecutive arginines. In further embodiments, one hydrophobic amino acid is adjacent to one of the arginines. In still other embodiments, the CPPs described herein comprise at least three consecutive hydrophobic amino acids and there consecutive arginines. In further embodiments, one hydrophobic amino acid is adjacent to one of the arginines. These various combinations of amino acids can have any arrangement of D and L amino acids, e.g., the sequences described above.

In some embodiments, any four adjacent amino acids in the CPPs described herein (e.g., the CPPs according to Formula 2) can have one of the following sequences: $AA_{H2}$-$AA_{H1}$-R-r, $AA_{H2}$-$AA_{H1}$-r-R, R-r-$AA_{H1}$-$AA_{H2}$, or r-R-$AA_{H1}$-$AA_{H2}$, wherein each of $AA_{H1}$ and $AA_{H2}$ are independently a hydrophobic amino acid. Accordingly, in some embodiments, the CPPs used in the polypeptide conjugates described herein have a structure according any of Formula 3A-D:

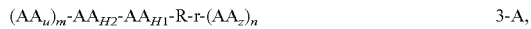  3-A,

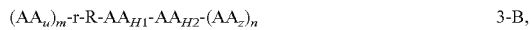  3-B,

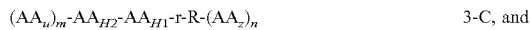  3-C, and

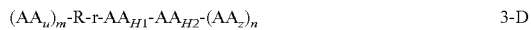  3-D wherein:
each of $AA_{H1}$ and $AA_{H2}$ are independently a hydrophobic amino acid;
at each instance and when present, each of $AA_u$ and $AA_z$ are independently any amino acid; and
m and n are independently selected from a number from 0 to 6.

In some embodiments, the total number of amino acids (including r, R, $AA_{H1}$, $AA_{H2}$), in the CPPs of Formula 3-A to 3-D are in the range of 4 to 10, e.g., 6. In some embodiments, the total number of amino acids is 4. In some embodiments, the total number of amino acids is 5. In some embodiments, the total number of amino acids is 6. In some embodiments, the total number of amino acids is 7. In some embodiments, the total number of amino acids is 8. In some embodiments, the total number of amino acids is 9. In some embodiments, the total number of amino acids is 10.

In some embodiments, the sum of m and n is from 2 to 6. In some embodiments, the sum of m and n is 2. In some embodiments, the sum of m and n is 3. In some embodiments, the sum of m and n is 4. In some embodiments, the sum of m and n is 5. In some embodiments, the sum of m and n is 6. In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, n is 0. In some embodiments, n is 1. In some embodiments, n is 2. In some embodiments, n is 3. In some embodiments, n is 4. In some embodiments, n is 5. In some embodiments, n is 6.

In some embodiments, each hydrophobic amino acid is independently selected from glycine, alanine, valine, leucine, isoleucine, methionine, phenylalanine, tryptophan, proline, naphthylalanine, phenylglycine, homophenylalanine, tyrosine, cyclohexylalanine, piperidine-2-carboxylic acid, or norleucine, each of which is optionally substituted with one or more substituents. In particular embodiments, each hydrophobic amino acid is independently a hydrophobic aromatic amino acid. In some embodiments, the aromatic hydrophobic amino acid is piperidine-2-carboxylic acid, naphthylalanine, phenylglycine, homophenylalanine, phenylalanine, tryptophan, or tyrosine, each of which is optionally substituted with one or more substituents. In particular embodiments, the hydrophobic amino acid is piperidine-2-carboxylic acid, naphthylalanine, tryptophan, or phenylalanine, each of which is optionally substituted with one or more substituents.

In some embodiments, each of $AA_{H1}$ and $AA_{H2}$ are independently a hydrophobic amino acid having a hydrophobicity value which is greater than that of glycine. In other embodiments, each of $AA_{H1}$ and $AA_{H2}$ are independently a hydrophobic amino acid having a hydrophobicity value which is greater than that of alanine. In still other embodiments, each of $AA_{H1}$ and $AA_{H2}$ are independently an hydrophobic amino acid having a hydrophobicity value which is greater than that of phenylalanine, e.g., as measured using the hydrophobicity scales described above, including Eisenberg and Weiss (Proc. Natl. Acad. Sci. U.S.A. 1984; 81(1): 140-144), Engleman, et al. (Ann. Rev. of Biophys. Biophys. Chem. 1986; 1986(15):321-53), Kyte and Doolittle (J. Mol. Biol. 1982; 57(1):105-132), Hoop and Woods (Proc. Natl. Acad. Sci. U.S.A. 1981; 78(6):3824-3828), and Janin (Nature. 1979; 277(5696):491-492), (see Table 1 above). In particular embodiments, hydrophobicity is measured using the hydrophobicity scale reported in Engleman, et al.

The presence of a hydrophobic amino acid on the N- or C-terminal of a D-Arg or L-Arg, or a combination thereof, has also found to improve the cytosolic uptake of the CPP (and the attached cargo). For example, in some embodiments, the CPPs disclosed herein may include $AA_{H1}$-D-Arg or D-Arg-$AA_{H1}$. In other embodiments, the CPPs disclosed herein may include $AA_{H1}$-L-Arg or L-Arg-$AA_{H1}$. In some embodiments, the presence of the hydrophobic amino acid on the N- or C-terminal of the D-Arg or L-Arg, or a combination thereof, in the CPP improves the cytosolic delivery efficiency by about 1.1 fold to about 30 fold, compared to an otherwise identical sequence, e.g., about 1.2, about 1.3, about 1.4, about 1.5, about 1.6, about 1.7, about 1.8, about 1.9, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 10, about 10.5, about 11.0, about 11.5, about 12.0, about 12.5, about 13.0, about 13.5, about 14.0, about 14.5, about 15.0, about 15.5, about 16.0, about 16.5, about 17.0, about 17.5, about 18.0, about 18.5, about 19.0, about 19.5, about 20, about 20.5, about 21.0, about 21.5, about 22.0, about 22.5, about 23.0, about 23.5, about 24.0, about 24.5, about 25.0, about 25.5, about 26.0, about 26.5, about 27.0, about 27.5, about 28.0, about 28.5, about 29.0, or about 29.5 fold, inclusive of all values and subranges therebetween. In some embodiments, the presence of the hydrophobic amino acid on the N- and/or C-terminal of the D-Arg and/or L-Arg in the CPP improves the cytosolic uptake efficiency by about 20 fold.

The size of the hydrophobic amino acid on the N- or C-terminal of the D-Arg or an L-Arg, or a combination thereof (i.e., $AA_{H1}$), may be selected to improve cytosolic delivery efficiency of the CPP. For example, a larger hydrophobic amino acid on the N- or C-terminal of a D-Arg or L-Arg, or a combination thereof, improves cytosolic delivery efficiency compared to an otherwise identical sequence having a smaller hydrophobic amino acid. The size of the hydrophobic amino acid can be measured in terms of molecular weight of the hydrophobic amino acid, the steric effects of the hydrophobic amino acid, the solvent-accessible surface area (SASA) of the side chain, or combinations thereof. In some embodiments, the size of the hydrophobic amino acid is measured in terms of the molecular weight of the hydrophobic amino acid, and the larger hydrophobic amino acid has a side chain with a molecular weight of at least about 90 g/mol, or at least about 130 g/mol, or at least about 141 g/mol. In other embodiments, the size of the amino acid is measured in terms of the SASA of the hydrophobic side chain, and the larger hydrophobic amino acid has a side chain with a SASA greater than alanine, or greater than glycine. In other embodiments, $AA_{H1}$ has a hydrophobic side chain with a SASA greater than or equal to about piperidine-2-carboxylic acid, greater than or equal to about tryptophan, greater than or equal to about phenylalanine, or equal to or greater than about naphthylalanine. In some embodiments, $AA_{H1}$ has a side chain side with a SASA of at least about 200 Å$^2$, at least about 210 Å$^2$, at least about 220 Å$^2$, at least about 240 Å$^2$, at least about 250 Å$^2$, at least about 260 Å$^2$, at least about 270 Å$^2$, at least about 280 Å$^2$, at least about 290 Å$^2$, at least about 300 Å$^2$, at least about 310 Å$^2$, at least about 320 Å$^2$, or at least about 330 Å$^2$. In some embodiments, AA$_{H2}$ has a side chain side with a SASA of at least about 200 Å$^2$, at least about 210 Å$^2$, at least about 220 Å$^2$, at least about 240 Å$^2$, at least about 250 Å$^2$, at least about 260 Å$^2$, at least about 270 Å$^2$, at least about 280 Å$^2$, at least about 290 Å$^2$, at least about 300 Å$^2$, at least about 310 Å$^2$, at least about 320 Å$^2$, or at least about 330 Å$^2$. In some embodiments, the side chains of AAR_ and AA$_{H2}$ have a combined SASA of at least about 350 Å$^2$, at least about 360 Å$^2$, at least about 370 Å$^2$, at least about 380 Å$^2$, at least about 390 Å$^2$, at least about 400 Å$^2$, at least about 410 Å$^2$, at least about 420 Å$^2$, at least about 430 Å$^2$, at least about 440 Å$^2$, at least about 450 Å$^2$, at least about 460 Å$^2$, at least about 470 Å$^2$, at least about 480 Å$^2$, at least about 490 Å$^2$, greater than about 500 Å$^2$, at least about 510 Å$^2$, at least about 520 Å$^2$, at least about 530 Å$^2$, at least about 540 Å$^2$, at least about 550 Å$^2$, at least about 560 Å$^2$, at least about 570 Å$^2$, at least about 580 Å$^2$, at least about 590 Å$^2$, at least about 600 Å$^2$, at least about 610 Å$^2$, at least about 620 Å$^2$, at least about 630 Å$^2$, at least about 640 Å$^2$, greater than about 650 Å$^2$, at least about 660 Å$^2$, at least about 670 Å$^2$, at least about 680 Å$^2$, at least about 690 Å$^2$, or at least about 700 Å$^2$. In some embodiments, AA$_{H2}$ is a hydrophobic amino acid with a side chain having a SASA that is less than or equal to the SASA of the hydrophobic side chain of AA$_{H1}$. By way of example, and not by limitation, a CPP having a Nal-Arg motif exhibits improved cytosolic delivery efficiency compared to an otherwise identical CPP having a Phe-Arg motif; a CPP having a Phe-Nal-Arg motif exhibits improved cytosolic delivery efficiency compared to an otherwise identical CPP having a Nal-Phe-Arg motif; and a phe-Nal-Arg motif exhibits improved cytosolic delivery efficiency compared to an otherwise identical CPP having a nal-Phe-Arg motif.

As used herein, "hydrophobic surface area" or "SASA" refers to the surface area (reported as square Ångstroms; Å2) of an amino acid side chain that is accessible to a solvent. In particular embodiments, SASA is calculated using the 'rolling ball' algorithm developed by Shrake & Rupley (*J Mol Biol.* 79 (2): 351-71), which is herein incorporated by reference in its entirety for all purposes. This algorithm uses a "sphere" of solvent of a particular radius to probe the surface of the molecule. A typical value of the sphere is 1.4 Å, which approximates to the radius of a water molecule.

SASA values for certain side chains are shown below in Table 3. In certain embodiments, the SASA values described herein are based on the theoretical values listed in Table 3 below, as reported by Tien, et al. (PLOS ONE 8(11): e80635. https://doi.org/10.1371/journal.pone.0080635, which is herein incorporated by reference in its entirety for all purposes.

TABLE 3

| Residue | Theoretical | Empirical | Miller et al. (1987) | Rose et al. (1985) |
|---|---|---|---|---|
| Alanine | 129.0 | 121.0 | 113.0 | 118.1 |
| Arginine | 274.0 | 265.0 | 241.0 | 256.0 |
| Asparagine | 195.0 | 187.0 | 158.0 | 165.5 |
| Aspartate | 193.0 | 187.0 | 151.0 | 158.7 |
| Cysteine | 167.0 | 148.0 | 140.0 | 146.1 |
| Glutamate | 223.0 | 214.0 | 183.0 | 186.2 |
| Glutamine | 225.0 | 214.0 | 189.0 | 193.2 |
| Glycine | 104.0 | 97.0 | 85.0 | 88.1 |

TABLE 3-continued

| Residue | Theoretical | Empirical | Miller et al. (1987) | Rose et al. (1985) |
|---|---|---|---|---|
| Histidine | 224.0 | 216.0 | 194.0 | 202.5 |
| Isoleucine | 197.0 | 195.0 | 182.0 | 181.0 |
| Leucine | 201.0 | 191.0 | 180.0 | 193.1 |
| Lysine | 236.0 | 230.0 | 211.0 | 225.8 |
| Methionine | 224.0 | 203.0 | 204.0 | 203.4 |
| Phenylalanine | 240.0 | 228.0 | 218.0 | 222.8 |
| Proline | 159.0 | 154.0 | 143.0 | 146.8 |
| Serine | 155.0 | 143.0 | 122.0 | 129.8 |
| Threonine | 172.0 | 163.0 | 146.0 | 152.5 |
| Tryptophan | 285.0 | 264.0 | 259.0 | 266.3 |
| Tyrosine | 263.0 | 255.0 | 229.0 | 236.8 |
| Valine | 174.0 | 165.0 | 160.0 | 164.5 |

In some embodiments, the CPP does not include a hydrophobic amino acid on the N- and/or C-terminal of AA$_{H2}$-AA$_{H1}$-R-r, AA$_{H2}$-AA$_{H1}$-r-R, R-r-AA$_{H1}$-AA$_{H2}$, or r-R-AA$_{H1}$-AA$_{H2}$. In alternative embodiments, the CPP does not include a hydrophobic amino acid having a side chain which is larger (as described herein) than at least one of AA$_{H1}$ or AA$_{H2}$. In further embodiments, the CPP does not include a hydrophobic amino acid with a side chain having a surface area greater than AA$_{H1}$. For example, in embodiments in which at least one of AA$_{H1}$ or AA$_{H2}$ is phenylalanine, the CPP does not further include a naphthylalanine (although the CPP include at least one hydrophobic amino acid which is smaller than AA$_{H1}$ and AA$_{H2}$, e.g., leucine). In still other embodiments, the CPP does not include a naphthylalanine in addition to the hydrophobic amino acids in AA$_{H2}$-AA$_{H1}$-R-r, AA$_{H2}$-AA$_{H1}$-r-R, R-r-AA$_{H1}$-AA$_{H2}$, or r-R-AA$_{H1}$-AA$_{H2}$.

The chirality of the amino acids (i.e., D or L amino acids) can be selected to improve cytosolic delivery efficiency of the CPP (and the attached cargo as described below). In some embodiments, the hydrophobic amino acid on the N- or C-terminal of an arginine (e.g., AA$_{H1}$) has the same or opposite chirality as the adjacent arginine. In some embodiments, AA$_{H1}$ has the opposite chirality as the adjacent arginine. For example, when the arginine is D-arg (i.e. "r"), AA$_{H1}$ is a D-AA$_{H1}$, and when the arginine is L-Arg (i.e., "R"), AA$_{H1}$ is a L-AA$_{H1}$. Accordingly, in some embodiments, the CPPs disclosed herein may include at least one of the following motifs: D-AA$_{H1}$-D-arg, D-arg-D-AA$_{H1}$, L-AA$_{H1}$-L-Arg, or L-Arg-LAA$_{H1}$. In particular embodiments, when arginine is D-arg, AA$_H$ can be D-nal, D-trp, or D-phe. In another non-limiting example, when arginine is L-Arg, AA$_H$ can be L-Nal, L-Trp, or L-Phe.

In some embodiments, the CPPs described herein include three arginines. Accordingly, in some embodiments, the CPPs described herein include one of the following sequences: AA$_{H2}$-AA$_{H1}$-R-r-R, AA$_{H2}$-AA$_{H1}$-R-r-r, AA$_{H2}$-AA$_{H1}$-r-R-R, AA$_{H2}$-AA$_{H1}$-r-R-r, R-R-r-AA$_{H1}$-AA$_{H2}$, r-R-r-AA$_{H1}$-AA$_{H2}$, r-r-R-AA$_{H1}$-AA$_{H2}$, or, R-r-R-AA$_{H1}$-AA$_{H2}$. In particular embodiments, the CPPs have one of the following sequences AA$_{H2}$-AA$_{H1}$-R-r-R, AA$_{H2}$-AA$_{H1}$-r-R-r, r-R-r-AA$_{H1}$-AA$_{H2}$, or R-r-R-AA$_{H1}$-AA$_{H2}$. In some embodiments, the chirality of AA$_{H1}$ and AA$_{H2}$ can be selected to improve cytosolic uptake efficiency, e.g., as described above, where AA$_{H1}$ has the same chirality as the adjacent arginine, and AA$_{H1}$ and AA$_{H2}$ have the opposite chirality.

In some embodiments, the CPPs described herein include three hydrophobic amino acids. Accordingly, in some embodiments, the CPPs described herein include one of the following sequences: AA$_{H3}$-AA$_{H2}$-AA$_{H1}$-R-r, AA$_{H3}$-AA$_{H2}$-AA$_{H1}$-R-r, AA$_{H3}$-AA$_{H2}$-AA$_{H1}$-r-R, AA$_{H3}$-AA$_{H2}$-AA$_{H1}$-r-R, R-r-AA$_{H1}$-AA$_{H2}$-AA$_{H3}$, R-r-AA$_{H1}$-AA$_{H2}$-AA$_{H3}$, r-R-

AA$_{H1}$-AA$_{H2}$-AA$_{H3}$, or, r-R-AA$_{H1}$-AA$_{H2}$-AA$_{H3}$, wherein AA$_{H3}$ is any hydrophobic amino acid described above, e.g., piperidine-2-carboxylic acid, naphthylalanine, tryptophan, or phenylalanine. In some embodiments, the chirality of AA$_{H1}$, AA$_{H2}$, and AA$_{H3}$ can be selected to improve cytosolic uptake efficiency, e.g., as described above, where AA$_{H1}$ has the same chirality as the adjacent arginine, and AA$_{H1}$ and AA$_{H2}$ have the opposite chirality. In other embodiments, the size of AA$_{H1}$, AA$_{H2}$, and AA$_{H3}$ can be selected to improve cytosolic uptake efficiency, e.g., as described above, where AA$_{H3}$ has a SAS of less than or equal to AA$_{H1}$ and/or AA$_{H2}$.

In some embodiments, AA$_{H1}$ and AA$_{H2}$ have the same or opposite chirality. In certain embodiments, AA$_{H1}$ and AA$_{H2}$ have the opposite chirality. Accordingly, in some embodiments, the CPPs disclosed herein include at least one of the following sequences: D-AA$_{H2}$-L-AA$_{H1}$-R-r; L-AA$_{H2}$-D-AA$_{H1}$-r-R; R-r-D-AA$_{H1}$-L-AA$_{H2}$; or r-R-L-AA$_{H1}$-D-AA$_{H1}$, wherein each of D-AA$_{H1}$ and D-AA$_{H2}$ is a hydrophobic amino acid having a D configuration, and each of L-AA$_{H1}$ and L-AA$_{H2}$ is a hydrophobic amino acid having an L configuration. In some embodiments, each of D-AA$_{H1}$ and D-AA$_{H2}$ is independently selected from the group consisting of D-pip, D-nal, D-trp, and D-phe. In particular embodiments, D-AA$_{H1}$ or D-AA$_{H2}$ is D-nal. In other particular embodiments, D-AA$_{H1}$ is D-nal. In some embodiments, each of L-AA$_{H1}$ and L-AA$_{H2}$ is independently selected from the group consisting of L-Pip, L-Nal, L-Trp, and L-Phe. In particular embodiments, each of L-AA$_{H1}$ and L-AA$_{H2}$ is L-Nal. In other particular embodiments, L-AA$_{H1}$ is L-Nal.

As discussed above, the disclosure provides for various modifications to a cyclic peptide sequence which may improve cytosolic delivery efficiency. In some embodiments, improved cytosolic uptake efficiency can be measured by comparing the cytosolic delivery efficiency of the CPP having the modified sequence to a proper control sequence. In some embodiments, the control sequence does not include a particular modification (e.g., matching chirality of R and AA$_{H1}$) but is otherwise identical to the modified sequence. In other embodiments, the control has the following sequence: cyclic(FΦRRRRQ) (SEQ ID NO: 65).

As used herein cytosolic delivery efficiency refers to the ability of a CPP to traverse a cell membrane and enter the cytosol. In embodiments, cytosolic delivery efficiency of the CPP is not dependent on a receptor or a cell type. Cytosolic delivery efficiency can refer to absolute cytosolic delivery efficiency or relative cytosolic delivery efficiency.

Absolute cytosolic delivery efficiency is the ratio of cytosolic concentration of a CPP (or a CPP-cargo conjugate) over the concentration of the CPP (or the CPP-cargo conjugate) in the growth medium. Relative cytosolic delivery efficiency refers to the concentration of a CPP in the cytosol compared to the concentration of a control CPP in the cytosol. Quantification can be achieved by fluorescently labeling the CPP (e.g., with a FTIC dye) and measuring the fluorescence intensity using techniques well-known in the art.

In particular embodiments, relative cytosolic delivery efficiency is determined by comparing (i) the amount of a CPP of the invention internalized by a cell type (e.g., HeLa cells) to (ii) the amount of the control CPP internalized by the same cell type. To measure relative cytosolic delivery efficiency, the cell type may be incubated in the presence of a cell-penetrating peptide of the invention for a specified period of time (e.g., 30 minutes, 1 hour, 2 hours, etc.) after which the amount of the CPP internalized by the cell is quantified using methods known in the art, e.g., fluorescence microscopy. Separately, the same concentration of the control CPP is incubated in the presence of the cell type over the same period of time, and the amount of the control CPP internalized by the cell is quantified.

In other embodiments, relative cytosolic delivery efficiency can be determined by measuring the IC$_{50}$ of a CPP having a modified sequence for an intracellular target, and comparing the IC$_{50}$ of the CPP having the modified sequence to a proper control sequence (as described herein).

Non-limiting examples of suitable cyclic cell penetrating peptide are provided in Table 4. The CPP sequence in the polypeptides of the present disclosure can include any of the CPP sequences provided in Table 4, or a subset of amino acids in the CPPs provided in Table 4.

TABLE 4

| ID | CPP Sequence |
|---|---|
| PCT 1 | FΦRRR (SEQ ID NO: 66) |
| PCT 2 | FΦRRRC (SEQ ID NO: 67) |
| PCT 3 | FΦRRRU (SEQ ID NO: 68) |
| PCT 4 | RRRΦF (SEQ ID NO: 69) |
| PCT 5 | RRRRΦF (SEQ ID NO: 70) |
| PCT 6 | FΦRRRR (SEQ ID NO: 71) |
| PCT 7 | FφrRrR (SEQ ID NO: 72) |
| PCT 8 | FφrRrR (SEQ ID NO: 72) |
| PCT 9 | FΦRRRR (SEQ ID NO: 71) |
| PCT 10 | fΦRrRr (SEQ ID NO: 73) |
| PCT 11 | RRFRΦR (SEQ ID NO: 74) |
| PCT 12 | FRRRRΦ (SEQ ID NO: 75) |
| PCT 13 | rRFRΦR (SEQ ID NO: 76) |
| PCT 14 | RRΦFRR (SEQ ID NO: 77) |
| PCT 15 | CRRRRFW (SEQ ID NO: 11) |
| PCT 16 | FfΦRrRr (SEQ ID NO: 78) |
| PCT 17 | FFΦRRRR (SEQ ID NO: 79) |
| PCT 18 | RFRFRΦR (SEQ ID NO: 80) |
| PCT 19 | URRRRFW (SEQ ID NO: 12) |
| PCT 20 | CRRRRFW (SEQ ID NO: 13) |
| PCT 21 | FΦRRRRQK (SEQ ID NO: 81) |
| PCT 22 | FΦRRRRQC (SEQ ID NO: 82) |
| PCT 23 | fΦRrRrR (SEQ ID NO: 83) |
| PCT 24 | FΦRRRRR (SEQ ID NO: 84) |
| PCT 25 | RRRRΦFDΩC (SEQ ID NO: 85) |
| PCT 26 | FΦRRR (SEQ ID NO: 66) |

TABLE 4-continued

| ID | CPP Sequence |
|---|---|
| PCT 27 | FWRRR (SEQ ID NO: 14) |
| PCT 28 | RRRΦF (SEQ ID NO: 69) |
| PCT 29 | RRRWF (SEQ ID NO: 15) |
| SAR 1 | FΦRRRR (SEQ ID NO: 71) |
| SAR 19 | FFRRR (SEQ ID NO: 16) |
| SAR 20 | FFrRr (SEQ ID NO: 86) |
| SAR 21 | FFRrR (SEQ ID NO: 87) |
| SAR 22 | FRFRR (SEQ ID NO: 17) |
| SAR 23 | FRRFR (SEQ ID NO: 18) |
| SAR 24 | FRRRF (SEQ ID NO: 19) |
| SAR 25 | GΦRRR (SEQ ID NO: 88) |
| SAR 26 | FFFRA (SEQ ID NO: 20) |
| SAR 27 | FFFRR (SEQ ID NO: 21) |
| SAR 28 | FFRRRR (SEQ ID NO: 22) |
| SAR 29 | FRRFRR (SEQ ID NO: 23) |
| SAR 30 | FRRRFR (SEQ ID NO: 24) |
| SAR 31 | RFFRRR (SEQ ID NO: 25) |
| SAR 32 | RFRRFR (SEQ ID NO: 26) |
| SAR 33 | FRFRRR (SEQ ID NO: 27) |
| SAR 34 | FFFRRR (SEQ ID NO: 28) |
| SAR 35 | FFRRRF (SEQ ID NO: 29) |
| SAR 36 | FRFFRR (SEQ ID NO: 30) |
| SAR 37 | RRFFFR (SEQ ID NO: 31) |
| SAR 38 | FFRFRR (SEQ ID NO: 32) |
| SAR 39 | FFRRFR (SEQ ID NO: 33) |
| SAR 40 | FRRFFR (SEQ ID NO: 34) |
| SAR 41 | FRRFRF (SEQ ID NO: 35) |
| SAR 42 | FRFRFR (SEQ ID NO: 36) |
| SAR 43 | RFFRFR (SEQ ID NO: 37) |
| SAR 44 | GΦRRRR (SEQ ID NO: 89) |
| SAR 45 | FFFRRRR (SEQ ID NO: 38) |
| SAR 46 | RFFRRRR (SEQ ID NO: 39) |
| SAR 47 | RRFFRRR (SEQ ID NO: 40) |
| SAR 48 | RFFFRRR (SEQ ID NO: 41) |
| SAR 49 | RRFFFRR (SEQ ID NO: 42) |
| SAR 50 | FFRRFRR (SEQ ID NO: 43) |
| SAR 51 | FFRRRRF (SEQ ID NO: 44) |
| SAR 52 | FRRFFRR (SEQ ID NO: 45) |
| SAR 53 | FFFRRRRR (SEQ ID NO: 46) |
| SAR 54 | FFFRRRRRR (SEQ ID NO: 47) |
| SAR 55 | FΦRrRr (SEQ ID NO: 90) |
| SAR 56 | XXRRRR (SEQ ID NO: 48) |
| SAR 57 | FfFRrR (SEQ ID NO: 91) |
| SAR 58 | fFfRrR (SEQ ID NO: 92) |
| SAR 59 | fFfRrR (SEQ ID NO: 93) |
| SAR 60 | FfFrRr (SEQ ID NO: 94) |
| SAR 61 | fFΦrRr (SEQ ID NO: 95) |
| SAR 62 | fΦfrRr (SEQ ID NO: 96) |
| SAR 63 | ΦFfrRr (SEQ ID NO: 97) |
| SAR 64 | FΦrRr (SEQ ID NO: 98) |
| SAR 65 | fΦrRr (SEQ ID NO: 99) |
| SAR 66 | Ac-(Lys-fFRrRrD) (SEQ ID NO: 100) |
| SAR 67 | Ac-(Dap-fFRrRrD) (SEQ ID NO: 101) |
| SAR 68 | CWWRRRRC (SEQ ID NO: 102)<br>└─S─S─┘ |
| SAR 69 | CWWVRRRRC (SEQ ID NO: 103)<br>└─S─S─┘ |
| SAR 70 | CFWRRRRC (SEQ ID NO: 104)<br>└─S─S─┘ |
| SAR 71 | CWWWRRRC (SEQ ID NO: 105)<br>└─S─S─┘ |

TABLE 4-continued

| ID | CPP Sequence |
|---|---|
| Pin1 15 | Pip-Nal-Arg-Glu-arg-arg-glu (SEQ ID NO: 106) |
| Pin1 16 | Pip-Nal-Arg-Arg-arg-arg-glu (SEQ ID NO: 107) |
| Pin1 17 | Pip-Nal-Nal-Arg-arg-arg-glu (SEQ ID NO: 108) |
| Pin1 18 | Pip-Nal-Nal-Arg-arg-arg-Glu (SEQ ID NO: 109) |
| Pin1 19 | Pip-Nal-Phe-Arg-arg-arg-glu (SEQ ID NO: 110) |
| Pin1 20 | Pip-Nal-Phe-Arg-arg-arg-Glu (SEQ ID NO: 111) |
| Pin1 21 | Pip-Nal-phe-Arg-arg-arg-glu) (SEQ ID NO: 112) |
| Pin1 22 | Pip-Nal-phe-Arg-arg-arg-Glu (SEQ ID NO: 113) |
| Pin1 23 | Pip-Nal-nal-Arg-arg-arg-Glu (SEQ ID NO: 114) |
| Pin1 24 | Pip-Nal-nal-Arg-arg-arg-glu (SEQ ID NO: 115) |
| Rev-13 | [Pim-RQRR-Nlys]GRRR[b] (SEQ ID NO: 116) |
| hLF | KCFQWQRNMRKVRGPPVSC (SEQ ID NO: 117) |
| cTat | [KrRrGrKkRrE][c] (SEQ ID NO: 118) |
| cR10 | [KrRrRrRrRrRrE][c] (SEQ ID NO: 119) |
| L-50 | [RVRTRGKRRIRRpP] (SEQ ID NO: 120) |
| L-51 | [RTRTRGKRRIRVpP] (SEQ ID NO: 121) |
| [WR]4 | [WRWRWRWR] (SEQ ID NO: 49) |
| MCoTI-II | [GGVCPKILKKCRRDSDCPGACICRGNGYCGSGSD] (SEQ ID NO: 122) |
| Rotstein et al. Chem. Eur. J. 2011 | [P-Cha-r-Cha-r-Cha-r-Cha-r-G][d] (SEQ ID NO: 123) |
| Lian et al. J. Am. Chem. Soc. 2014 | Tm(SvP-F$_2$Pmp-H)-Dap-(FΦRRRRR-Dap)][f] (SEQ ID NO: 124) |
| Lian et al. J Am. Chem. Soc. 2014 | [Tm(a-Sar-D-pThr-Pip-ΦRAa)-Dap-(FΦRRRRR-Dap)][f] (SEQ ID NO: 125) |
| IA8b | [CRRSRRGCGRRSRRCG][g] (SEQ ID NO: 127) |
| Dod-[R5] | [K(Dod)RRRR] (SEQ ID NO: 128) |
| LK-3 | LKKLCKLLKKLCKLAG (SEQ ID NO: 129) |
| | LKKLCKLLKKLCKLAG (SEQ ID NO: 129) |
| | RRRR-[KRRRE][c] (SEQ ID NO: 130) |
| | RRR-[KRRRRE][c] (SEQ ID NO: 131) |
| | RR-[KRRRRRE][c] (SEQ ID NO: 132) |
| | R-[KRRRRRRE][c] (SEQ ID NO: 133) |
| [CR]4 | [CRCRCRCR] (SEQ ID NO: 134) |
| cyc3 | [Pra-LRKRLRKFRN-AzK][h] (SEQ ID NO: 135) |
| PMB | T-Dap-[Dap-Dap-f-L-Dap-Dap-T] (SEQ ID NO: 136) |
| GPMB | T-Agp-[Dap-Agp-f-L-Agp-Agp-T] (SEQ ID NO: 137) |
| CPP1 | FΦRRRRR (SEQ ID NO: 71) |
| CPP12 | FfΦRrRr (SEQ ID NO: 78) |
| CPP9 | fΦRrRr (SEQ ID NO: 73) |
| CPP11 | fΦRrRrR (SEQ ID NO: 83) |
| CPP18 | FφrRrR (SEQ ID NO: 72) |
| CPP13 | FφrRrR (SEQ ID NO: 72) |
| CPP6 | FΦRRRRRR (SEQ ID NO: 84) |
| CPP3 | RRFRΦR (SEQ ID NO: 74) |
| CPP7 | FFΦRRRR (SEQ ID NO: 79) |
| CPP8 | RFRFRΦR (SEQ ID NO: 80) |
| CPP5 | FΦRRR (SEQ ID NO: 66) |
| CPP4 | FRRRRΦ (SEQ ID NO: 75) |

TABLE 4-continued

| ID | CPP Sequence |
|---|---|
| CPP10 | rRFRΦR (SEQ ID NO: 76) |
| CPP2 | RRΦFRR (SEQ ID NO: 77) |

Φ, L-2-naphthylalanine;
Pim, pimelic acid;
Nlys, lysine peptoid residue;
D-pThr, D-phosphothreonine;
Pip, L-piperidine-2-carboxylic acid;
Cha, L-3-cyclohexyl-alanine;
Tm, trimesic acid;
Dap, L-2,3-diaminopropionic acid;
Sar, sarcosine;
F$_2$Pmp, L-difluorophosphonomethyl phenylalanine;
Dod, dodecanoyl;
Pra, L-propargylglycine;
AzK, L-6-Azido-2-amino-hexanoic;
Agp, L-2-amino-3-guanidinylpropionic acid;
[b]Cyclization between Pim and Nlys;
[c]Cyclization between Lys and Glu;
[d]Macrocyclization by multicomponent reaction with aziridine aldehyde and isocyanide;
[e]Cyclization between the main-chain of Gln residue;
[f]N-terminal amine and side chains of two Dap residues bicyclized with Tm;
[g]Three Cys side chains bicyclized with tris(bromomethyl)benzene;
[h]Cyclization by the click reaction between Pra and Azk.

The cell-penetrating peptide sequences of the present disclose can include any of those disclosed in US 2017/0355730 A1, WO/2018/098231 (and the US patent application publication related thereto), and U.S. Provisional application No. 62/669,146 (and the US patent application publication related thereto), each of which are herein incorporated by reference in its entirety for all purposes.

In certain embodiments, the cytosolic delivery efficiency of a particular CPP used in the bicyclic polypeptide of the claimed invention, may also be dependent on the sequence of Xm. In further embodiments of the invention, a particular CPP/Xm bicyclic polypeptide may have an improved cytosolic delivery efficiency of about 1.1 fold to about 30 fold, compared to an bicyclic polypeptide having an identical CPP and a different Xm, e.g., about 1.2, about 1.3, about 1.4, about 1.5, about 1.6, about 1.7, about 1.8, about 1.9, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 10, about 10.5, about 11.0, about 11.5, about 12.0, about 12.5, about 13.0, about 13.5, about 14.0, about 14.5, about 15.0, about 15.5, about 16.0, about 16.5, about 17.0, about 17.5, about 18.0, about 18.5, about 19.0, about 19.5, about 20, about 20.5, about 21.0, about 21.5, about 22.0, about 22.5, about 23.0, about 23.5, about 24.0, about 24.5, about 25.0, about 25.5, about 26.0, about 26.5, about 27.0, about 27.5, about 28.0, about 28.5, about 29.0, or about 29.5 fold inclusive of all values and subranges therebetween. In further embodiments of the invention, a particular CPP/Xm bicyclic polypeptide may have an improved cytosolic delivery efficiency of about 1.1 fold to about 30 fold, compared to an bicyclic polypeptide having an identical Xm and a different CPP, e.g., about 1.2, about 1.3, about 1.4, about 1.5, about 1.6, about 1.7, about 1.8, about 1.9, about 2.0, about 2.5, about 3.0, about 3.5, about 4.0, about 4.5, about 5.0, about 5.5, about 6.0, about 6.5, about 7.0, about 7.5, about 8.0, about 8.5, about 9.0, about 10, about 10.5, about 11.0, about 11.5, about 12.0, about 12.5, about 13.0, about 13.5, about 14.0, about 14.5, about 15.0, about 15.5, about 16.0, about 16.5, about 17.0, about 17.5, about 18.0, about 18.5, about 19.0, about 19.5, about 20, about 20.5, about 21.0, about 21.5, about 22.0, about 22.5, about 23.0, about 23.5, about 24.0, about 24.5, about 25.0, about 25.5, about 26.0, about 26.5, about 27.0, about 27.5, about 28.0, about 28.5, about 29.0, or about 29.5 fold inclusive of all values and subranges therebetween.

In certain embodiments, L-2,3-diaminopropionic acid may be conjugated to the C-terminal of the CPP sequences in Table 4 to facilitate conjugation to the L. In other embodiments, the C-terminal amino acid of the CPP sequences in listed in Table 4 may be substituted with L-2,3-diaminopropionic acid to facilitate conjugation to the L.

Additionally, the CPP used in the polypeptide conjugates and methods described herein can include any sequence disclosed in: U.S. application Ser. No. 15/312,878; U.S. application Ser. No. 15/360,719; U.S. App. No. 62/438,141, and U.S. App. No. 62/507,483, each of which is incorporated by reference in its entirety for all purposes.

Linker

In various embodiments, the polypeptides disclosed herein comprise a linker ("L"). The L may be any appropriate moiety which is capable of forming a covalent bond to the Xm, CPP, or a combination thereof, to form the bicyclic peptides of the present disclosure. In certain embodiments, the L is a pharmaceutically acceptable moiety. In some embodiments, the L is any appropriate trivalent radical.

In some embodiments, the L is may be an alkylene, alkenylene, alkynylene, aryl, cycloalkyl, cycloalkenyl, cycloalkynyl, heterocyclyl, heteroaryl, or N-alkyl, each of which can be optionally substituted as defined herein.

"Alkylene" or "alkylene chain" refers to a fully saturated, straight or branched trivalent hydrocarbon chain radical, having from one to forty carbon atoms. Non-limiting examples of $C_2$-$C_{40}$ alkylene include ethylene, propylene, n-butylene, ethenylene, propenylene, n-butenylene, propynylene, n-butynylene, and the like. Unless stated otherwise specifically in the specification, an alkylene chain can be optionally substituted as described herein.

"Alkenylene" or "alkenylene chain" refers to a straight or branched trivalent hydrocarbon chain radical, having from two to forty carbon atoms, and having one or more carbon-carbon double bonds. Non-limiting examples of $C_2$-$C_{40}$ alkenylene include ethene, propene, butene, and the like.

Unless stated otherwise specifically in the specification, an alkenylene chain can be optionally substituted.

"Alkynylene" or "alkynylene chain" refers to a straight or branched trivalent hydrocarbon chain radical, having from two to forty carbon atoms, and having one or more carbon-carbon triple bonds. Non-limiting examples of $C_2$-$C_{40}$ alkynylene include ethynylene, propargylene and the like. Unless stated otherwise specifically in the specification, an alkynylene chain can be optionally substituted.

"Aryl" refers to a hydrocarbon ring system trivalent radical comprising hydrogen, 6 to 40 carbon atoms and at least one aromatic ring. For purposes of this invention, the aryl trivalent radical can be a monocyclic, bicyclic, tricyclic or tetracyclic ring system, which can include fused or bridged ring systems. Aryl trivalent radicals include, but are not limited to, aryl trivalent radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl group can be optionally substituted.

"Cycloalkyl" refers to a stable non-aromatic monocyclic or polycyclic fully saturated hydrocarbon trivalent radical having from 3 to 40 carbon atoms and at least one ring, wherein the ring consists solely of carbon and hydrogen atoms, which can include fused or bridged ring systems. Monocyclic cycloalkyl trivalent radicals include, for example, cyclopropyl, cyclobutyl, cyclopentyl, cyclohexyl, cycloheptyl, and cyclooctyl. Polycyclic cycloalkyl trivalent radicals include, for example, adamantyl, norbornyl, decalinyl, 7,7-dimethyl-bicyclo[2.2.1]heptanyl, and the like. Unless otherwise stated specifically in the specification, a cycloalkyl group can be optionally substituted.

"Cycloalkenyl" refers to a stable non-aromatic monocyclic or polycyclic hydrocarbon trivalent radical having from 3 to 40 carbon atoms, at least one ring having, and one or more carbon-carbon double bonds, wherein the ring consists solely of carbon and hydrogen atoms, which can include fused or bridged ring systems. Monocyclic cycloalkenyl radicals include, for example, cyclopentenyl, cyclohexenyl, cycloheptenyl, cyclooctenyl, and the like. Polycyclic cycloalkenyl radicals include, for example, bicyclo[2.2.1]hept-2-enyl and the like. Unless otherwise stated specifically in the specification, a cycloalkenyl group can be optionally substituted.

"Cycloalkynyl" refers to a stable non-aromatic monocyclic or polycyclic hydrocarbon trivalent radical having from 3 to 40 carbon atoms, at least one ring having, and one or more carbon-carbon triple bonds, wherein the ring consists solely of carbon and hydrogen atoms, which can include fused or bridged ring systems. Monocyclic cycloalkynyl radicals include, for example, cycloheptynyl, cyclooctynyl, and the like. Unless otherwise stated specifically in the specification, a cycloalkynyl group can be optionally substituted.

"Heterocyclyl," "heterocyclic ring" or "heterocycle" refers to a stable 3- to 20-membered non-aromatic ring trivalent radical which consists of two to twelve carbon atoms and from one to six heteroatoms selected from the group consisting of nitrogen, oxygen and sulfur. Heterocyclyl or heterocyclic rings include heteroaryls as defined below. Unless stated otherwise specifically in the specification, the heterocyclyl radical can be a monocyclic, bicyclic, tricyclic or tetracyclic ring system, which can include fused or bridged ring systems; and the nitrogen, carbon or sulfur atoms in the heterocyclyl radical can be optionally oxidized; the nitrogen atom can be optionally quaternized; and the heterocyclyl radical can be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless stated otherwise specifically in the specification, a heterocyclyl group can be optionally substituted.

"Heteroaryl" refers to a 5- to 20-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical can be a monocyclic, bicyclic, tricyclic or tetracyclic ring system, which can include fused or bridged ring systems; and the nitrogen, carbon or sulfur atoms in the heteroaryl radical can be optionally oxidized; the nitrogen atom can be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group can be optionally substituted.

"N-alkyl" refers to a alkyl radical as defined above containing at least one nitrogen and where a point of attachment of the alkyl radical to the rest of the molecule is through a nitrogen atom in the N-alkyl radical. Unless stated otherwise specifically in the specification, a N-alkyl group can be optionally substituted.

The term "substituted" used herein means any of the above groups (i.e., alkylene, alkenylene, alkynylene, aryl, carbocyclyl, cycloalkyl, cycloalkenyl, cycloalkynyl, heterocyclyl, and/or heteroaryl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —NR$_g$R$_h$, —NR$_g$C(=O)R$_h$, —NR$_g$C(=O)NR$_g$R$_h$, —NR$_g$C(=O)OR$_h$, —NR$_g$SO$_2$R$_h$, —OC(=O)NR$_g$R$_h$, —OR$_g$, —SR$_g$, —SOR$_g$, —SO$_2$R$_g$, —OSO$_2$R$_g$, —SO$_2$OR$_g$, =NSO$_2$R$_g$, and —SO$_2$NR$_g$R$_h$. "Substituted also means any of the above groups in which one or more hydrogen atoms are replaced with —C(=O)R$_g$, —C(=O)OR$_g$, —C(=O)NR$_g$R$_h$, —CH$_2$SO$_2$R$_g$, —CH$_2$SO$_2$NR$_g$R$_h$. In the foregoing, R$_g$ and R$_h$ are the same or different and independently hydrogen, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkenyl, alkynyl, alkoxy, alkylamino, thioalkyl, aryl, aralkyl, cycloalkyl, cycloalkenyl, cycloalkynyl, cycloalkylalkyl, haloalkyl, haloalkenyl, haloalkynyl, heterocyclyl, N-heterocyclyl, heterocyclylalkyl, heteroaryl, N-heteroaryl and/or heteroarylalkyl group. In addition, each of the foregoing substituents can also be optionally substituted with one or more of the above substituents. Further, those skilled in the art will recognize that "substituted" also encompasses instances in which one or more hydrogen atoms on any of the above groups are replaced by a substituent listed in this paragraph, and the substituent forms a covalent bond with the CPP or the Xm. For example, in certain embodiments, any of the above groups (i.e., alkylene, alkenylene, alkynylene, aryl, carbocyclyl, cycloalkyl, cycloalkenyl, cycloalkynyl, heterocyclyl, and/or heteroaryl) can be substituted at one or more positions with a carboxylic acid (i.e., —C(=O)OH) which forms an amide bond with an amino group in the CPP and/or Xm (e.g., the N-terminus of the CPP or the Xm, or an amino group on a side chain of an amino acid in the CPP and/or Xm).

In some embodiments, the L is an aryl ring, which is independently substituted at three separate locations on the aryl ring. In certain embodiments, the aryl ring is a phenyl ring.

In some embodiments, the L forms a covalent bond with an amino acid in the Xm and/or the CPP. The resulting moiety, when L forms a bond to Xm and/or the CPP, to form the bicyclic polypeptides described herein, are referred to as R1, R2, and R3. In other embodiments, the L forms a covalent bond with the N- or C-terminus of an amino acid in the Xm and/or the CPP, or the side chain of an amino acid in the Xm and/or the CPP.

In some embodiments, each of R1, R2, and R3 are independently selected form an amide, an ester, and triazole, and combinations thereof. In further embodiments, each of R1, R2, and R3 are and an amide.

In certain embodiments, the bicyclic polypeptide has the structure of Formula 1A, 1B, 1C. or 1D, wherein each AA$_L$, when present, is, independently, selected from a D or L amino acid.

Each AA$_L$ may be a natural or non-natural amino acid as described above. In particular embodiments, p is one and AA$_L$ is Dap.

In some embodiments, the precursor to L (i.e., the moiety before L forms one or more covalent bonds to the Xm and/or CPP) is L-(C(O)OH)$_3$. In some such embodiments, the precursor to L has a structure according to Formula 4:

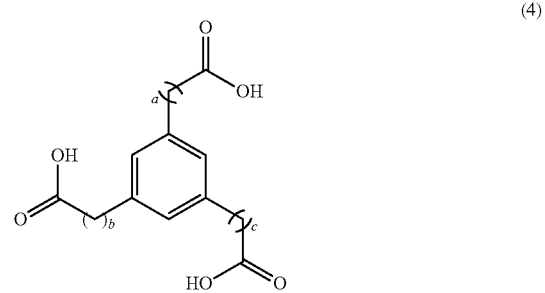

(4)

wherein a, b, and c are independently selected from a number from 0 to 10.

In various embodiments, the disclosure provides for bicyclic polypeptides according to Formula 5A or 5B:

(5A)

(5B)

wherein:
the CPP comprises a sequence according to Formula 2:

$(AA_u)_m$-AA$_1$-AA$_2$-AA$_3$-AA$_4$-$(AA_z)_n$       2 wherein:
each of AA$_1$, AA$_2$, AA$_3$, and AA$_4$, are independently selected from a D or L amino acid,
each of AA$_u$ and AA$_z$, at each instance and when present, are independently selected from a D or L amino acid, and
m and n are independently selected from a number from 0 to 6; and wherein:
at least two of AA$_u$, when present, AA$_1$, AA$_2$, AA$_3$, AA$_4$, and AA$_z$, when present, are independently arginine, and
at least two of AA$_u$, when present, AA$_1$, AA$_2$, AA$_3$, AA$_4$, and AA$_z$, when present, are independently a hydrophobic amino acid;

Xm is a peptide sequence is a 3-10 amino acid sequence comprising one or more amino acids selected from G, g, W, w, I, i, Y, y, A, and a (SEQ ID NO: 64);
L is a linker moiety; and
each of R$_1$, R$_2$, and R$_3$ are independently, a bonding moiety,
wherein the bonding moiety is formed when Xm, CPP, or a combination thereof, covalently bind to L to form the bicyclic polypeptide.

In various embodiments, the disclosure provides for bicyclic polypeptides according to Formula 5C or 5D:

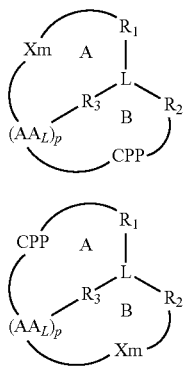

(5C)

(5D)

wherein:
the CPP comprises a sequence according to Formula 2:

$$(AA_u)_m\text{-}AA_1\text{-}AA_2\text{-}AA_3\text{-}AA_4\text{-}(AA_z)_n \qquad 2$$

wherein:
each of $AA_1$, $AA_2$, $AA_3$, and $AA_4$, are independently selected from a D or L amino acid,
each of $AA_u$ and $AA_z$, at each instance and when present, are independently selected from a D or L amino acid, and
m and n are independently selected from a number from 0 to 6; and
wherein:
at least two of $AA_u$, when present, $AA_1$, $AA_2$, $AA_3$, $AA_4$, and $AA_z$, when present, are independently arginine, and
at least two of $AA_u$, when present, $A_{A1}$, $AA_2$, $AA_3$, $AA_4$, and $AA_z$, when present, are independently a hydrophobic amino acid;
Xm is a peptide sequence is a 3-10 amino acid sequence comprising one or more amino acids selected from G, g, W, w, I, i, Y, y, A, and a (SEQ ID NO: 64);
$AA_L$ at each instance is an amino acid;
p is selected from a number from 0 to 3 (e.g., 0, 1, 2, or 3);
L is a linker moiety; and
each of $R_1$, $R_2$, and $R_3$ are independently, a bonding moiety,
wherein the bonding moiety is formed when Xm, CPP, or a combination thereof, covalently bind to L to form the bicyclic polypeptide.
In further embodiments of the invention, the CPP of the bicyclic polypeptide of Formula 5A-5D comprises a sequence according to Formula 3A-D:

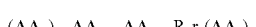  3-A,

  3-B,

  3-C, and

  3-D wherein:
each of $AA_{H1}$ and $AA_{H2}$ are independently a hydrophobic amino acid;

at each instance and when present, each of $AA_u$ and $AA_z$ are independently any amino acid; and
m and n are independently selected from a number from 0 to 6.

In still further embodiments of the invention the Xm peptide sequence of the bicyclic polypeptide of Formulae 1A-1D and 5A-5D is a 3-7 amino acid sequence comprising a sequence selected from WI, IW, Wi, iW, wI, Iw, iw, wi.

In yet further embodiments of the invention, the Xm peptide sequence of the bicyclic polypeptide of Formulae 1A-1D and 5A-5D is a 4-7 amino acid sequence comprising a sequence selected from the group consisting of: GWIY (SEQ ID NO:1); GWIYA (SEQ ID NO:2); GWIYa (SEQ ID NO: 50); AGWIY (SEQ ID NO:3); aGWIY (SEQ ID NO: 51); AWIYA (SEQ ID NO:4); GAIYA (SEQ ID NO:5); GWAYA (SEQ ID NO:6); GWIAA (SEQ ID NO:7); GWIYA (SEQ ID NO:8); GAIAA (SEQ ID NO:9); and GAAAA (SEQ ID NO:10), and the inverse of such sequences (SEQ ID NOs: 52-63).

Methods of Treatment

In some embodiments, the polypeptides disclosed herein inhibit the NEMO-IKKα/β interaction by at least about 10%, e.g., about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, and about 100%, inclusive of all values and subranges therebetween.

As used herein, the terms "inhibit," inhibited," "inhibition," "inhibiting" or other derivations or variations thereof refer to the activity of a particular enzyme which is reduced by using an inhibitor. In some embodiments, "inhibition" can refer to complete loss of function of an enzyme or a reduction of the activity of the enzyme (e.g., by about 1% or more). The level of reduction is compared to a comparable host cell of the same species which is not treated by the inhibitor.

In some embodiments, the polypeptides disclosed herein have an $IC_{50}$ of about 10 μM or less when measured for the NEMO-IKKα/β interaction, e.g., about 9 about 8 about 7 about 6 about 5 about 4 about 3 about 2 about 1 about 0.9 about 0.8 about 0.7 about 0.6 about 0.5 about 0.4 about 0.3 about 0.2 about 0.1 μM, about 0.09 about 0.08 about 0.07 about 0.06 about 0.05 about 0.04 about 0.03 about 0.02 or about 0.01 μM or less, inclusive of all values and subranges therebetween. In particular embodiments, polypeptides have an IC50 of about 1.0 μM or less when measured for the NEMO-IKKα/β interaction.

Methods of Making

The polypeptide conjugates described herein can be prepared in a variety of ways known to one skilled in the art of organic synthesis or variations thereon as appreciated by those skilled in the art. The compounds described herein can be prepared from readily available starting materials. Optimum reaction conditions can vary with the particular reactants or solvents used, but such conditions can be determined by one skilled in the art.

Variations on the compounds described herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

The starting materials and reagents used in preparing the disclosed compounds and compositions are either available from commercial suppliers such as Aldrich Chemical Co., (Milwaukee, WI), Acros Organics (Morris Plains, NJ), Fisher Scientific (Pittsburgh, PA), Sigma (St. Louis, MO), Pfizer (New York, NY), GlaxoSmithKline (Raleigh, NC), Merck (Whitehouse Station, NJ), Johnson & Johnson (New Brunswick, NJ), Aventis (Bridgewater, NJ), AstraZeneca (Wilmington, DE), Novartis (Basel, Switzerland), Wyeth (Madison, NJ), Bristol-Myers-Squibb (New York, NY), Roche (Basel, Switzerland), Lilly (Indianapolis, IN), Abbott (Abbott Park, Ill.), Schering Plough (Kenilworth, NJ), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the pharmaceutical carriers disclosed herein can be obtained from commercial sources.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high-performance liquid chromatography (HPLC) or thin layer chromatography.

The disclosed compounds can be prepared by solid phase peptide synthesis wherein the amino acid α-N-terminal is protected by an acid or base protecting group. Such protecting groups should have the properties of being stable to the conditions of peptide linkage formation while being readily removable without destruction of the growing peptide chain or racemization of any of the chiral centers contained therein. Suitable protecting groups are 9-fluorenylmethyloxycarbonyl (Fmoc), t-butyloxycarbonyl (Boc), benzyloxycarbonyl (Cbz), biphenylisopropyloxycarbonyl, t-amyloxycarbonyl, isobornyloxycarbonyl, α,α-dimethyl-3,5-dimethoxybenzyloxycarbonyl, o-nitrophenylsulfenyl, 2-cyano-t-butyloxycarbonyl, and the like. The 9-fluorenylmethyloxycarbonyl (Fmoc) protecting group is particularly preferred for the synthesis of the disclosed compounds. Other preferred side chain protecting groups are, for side chain amino groups like lysine and arginine, 2,2,5,7,8-pentamethylchroman-6-sulfonyl (pmc), nitro, p-toluenesulfonyl, 4-methoxybenzene-sulfonyl, Cbz, Boc, and adamantyloxycarbonyl; for tyrosine, benzyl, o-bromobenzyloxy-carbonyl, 2,6-dichlorobenzyl, isopropyl, t-butyl (t-Bu), cyclohexyl, cyclopenyl and acetyl (Ac); for serine, t-butyl, benzyl and tetrahydropyranyl; for histidine, trityl, benzyl, Cbz, p-toluenesulfonyl and 2,4-dinitrophenyl; for tryptophan, formyl; for asparticacid and glutamic acid, benzyl and t-butyl and for cysteine, triphenylmethyl (trityl). In the solid phase peptide synthesis method, the α-C-terminal amino acid is attached to a suitable solid support or resin. Suitable solid supports useful for the above synthesis are those materials which are inert to the reagents and reaction conditions of the stepwise condensation-deprotection reactions, as well as being insoluble in the media used. Solid supports for synthesis of α-C-terminal carboxy peptides is 4-hydroxymethylphenoxymethyl-copoly(styrene-1% divinylbenzene) or 4-(2',4'-dimethoxyphenyl-Fmoc-aminomethyl)phenoxyacetamidoethyl resin available from Applied Biosystems (Foster City, Calif). The α-C-terminal amino acid is coupled to the resin by means of N,N'-dicyclohexylcarbodiimide (DCC), N,N'-dii sopropylcarbo-diimide (DIC) or O-benzotriazol-1-yl-N,N,N',N'-tetramethyluroniumhexafluorophosphate (HBTU), with or without 4-dimethylaminopyridine (DMAP), 1-hydroxybenzotriazole (HOBT), benzotriazol-1-yloxy-tris(dimethylamino)phosphoniumhexafluorophosphate (BOP) or bis(2-oxo-3-oxazo-lidinyl)phosphine chloride (BOPCl), mediated coupling for from about 1 to about 24 hours at a temperature of between 10° C. and 50° C. in a solvent such as dichloromethane or DMF. When the solid support is 4-(2',4'-dimethoxyphenyl-Fmoc-aminomethyl)phenoxy-acetamidoethyl resin, the Fmoc group is cleaved with a secondary amine, preferably piperidine, prior to coupling with the α-C-terminal amino acid as described above. One method for coupling to the deprotected 4 (2',4'-dimethoxyphenyl-Fmoc-aminomethyl) phenoxy-acetamidoethyl resin is O-benzotriazol-1-yl-N,N, N',N'-tetramethyluroniumhexafluorophosphate (HBTU, 1 equiv.) and 1-hydroxybenzotriazole (HOBT, 1 equiv.) in DMF. The coupling of successive protected amino acids can be carried out in an automatic polypeptide synthesizer. In one example, the α-N-terminal in the amino acids of the growing peptide chain are protected with Fmoc. The removal of the Fmoc protecting group from the α-N-terminal side of the growing peptide is accomplished by treatment with a secondary amine, preferably piperidine. Each protected amino acid is then introduced in about 3-fold molar excess, and the coupling is preferably carried out in DMF. The coupling agent can be O-benzotriazol-1-yl-N,N,N',N'-tetramethyluroniumhexafluorophosphate (HBTU, 1 equiv.) and 1-hydroxybenzotriazole (HOBT, 1 equiv.). At the end of the solid phase synthesis, the polypeptide is removed from the resin and deprotected, either in successively or in a single operation. Removal of the polypeptide and deprotection can be accomplished in a single operation by treating the resin-bound polypeptide with a cleavage reagent comprising thianisole, water, ethanedithiol and trifluoroacetic acid. In cases wherein the α-C-terminal of the polypeptide is an alkylamide, the resin is cleaved by aminolysis with an alkylamine. Alternatively, the peptide can be removed by transesterification, e.g. with methanol, followed by aminolysis or by direct transamidation. The protected peptide can be purified at this point or taken to the next step directly. The removal of the side chain protecting groups can be accomplished using the cleavage cocktail described above. The fully deprotected peptide can be purified by a sequence of chromatographic steps employing any or all of the following types: ion exchange on a weakly basic resin (acetate form); hydrophobic adsorption chromatography on underivitized polystyrene-divinylbenzene (for example, Amberlite XAD); silica gel adsorption chromatography; ion exchange chromatography on carboxymethylcellulose; partition chromatography, e.g. on Sephadex G-25, LH-20 or countercurrent distribution; high performance liquid chromatography (HPLC), especially reverse-phase HPLC on octyl- or octadecylsilyl-silica bonded phase column packing.

Methods of Administration

In vivo application of the disclosed polypeptide conjugates, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, intranasal, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 100% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer for intracranial tumors; poly[bis(p-carboxyphenoxy) propane: sebacic acid] in a 20:80 molar ratio (as used in GLIADEL); chondroitin; chitin; and chitosan.

Compounds and compositions disclosed herein, including pharmaceutically acceptable salts or prodrugs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze-drying techniques, which yield a powder of the active ingredient plus any additional desired ingredient present in the previously sterile-filtered solutions.

Useful dosages of the compounds and agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counter indications. Dosage can vary, and can be administered in one or more dose administrations daily, for one or several days.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

Also disclosed are kits that comprise a compound disclosed herein in one or more containers. The disclosed kits can optionally include pharmaceutically acceptable carriers and/or diluents. In one embodiment, a kit includes one or more other components, adjuncts, or adjuvants as described herein. In another embodiment, a kit includes one or more anti-cancer agents, such as those agents described herein. In one embodiment, a kit includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent disclosed herein is provided in the kit as a solid, such as a tablet, pill, or powder form. In another embodiment, a compound and/or agent disclosed herein is provided in the kit as a liquid or solution. In one embodiment, the kit comprises an ampoule or syringe containing a compound and/or agent disclosed herein in liquid or solution form.

A number of embodiments of the invention have been described. Nevertheless, it will be understood that various modifications may be made without departing from the spirit and scope of the invention. Accordingly, other embodiments are within the scope of the following claims.

EXAMPLES

Example 1. Design and Synthesis of Combinatorial Library of Cell-Permeable Bicyclic Peptides A bicyclic peptide library featuring random peptide sequences of 3-6 residues in the first ring (A ring) and 12 different CPP sequences in the second ring (B ring) was designed and prepared (FIG. 1). The peptide library was synthesized on 2 g of TentaGel S NH2 resin (130 μm) by modifying a previously reported protocol disclosed in Lian et al. (Am. Chem. Soc. 2013, 135, 11990-11995), which is incorporated by reference herein in its entirety. Library screening was also performed according to previously established protocols in Lian et al. (Am. Chem. Soc. 2013, 135, 11990-11995). In brief, approximately 600 mg of the bicyclic peptide library was swollen in DCM and washed extensively with DMF, ddH$_2$O and finally incubated overnight at 4° C. in 1.0 mL of blocking buffer (30 mM sodium phosphate, pH 7.4, 150 mM NaCl, 0.05% Tween 20, 3% BSA and 0.1% gelatin). The solution was drained and the resin was resuspended in blocking buffer containing 1.0 μM biotinylated GST-NEMO for 4 hours at 4° C. Unbound NEMO was washed away with blocking buffer and the beads were resuspended in 10 mL of blocking buffer. Twenty μL of M280 streptavidin-coated Dynabeads (Invitrogen) was added to the solution and allowed to incubate on a rotary wheel for 1 hour at 4° C. The magnetic beads were isolated from the bulk by using a TA Dynal MPC-1 magnetic particle concentrator (Invitrogen). Hit beads were transferred to a Bio-Spin column (0.8 mL, BioRad) and incubated in blocking buffer containing 1.0 μM biotinylated GST-NEMO for 4 hours at 4° C. The solution was drained and the resin was washed with blocking buffer to remove unbound protein. The resin was resuspended in 1 mL of blocking buffer and streptavidin-alkaline phosphatase (SA-AP) conjugate was added to the tube (1 mg/mL final concentration). After 10 minutes at 4° C. the solution was drained and the beads were quickly washed with 1 mL of blocking buffer (3×) and 1 mL of staining buffer (30 mM Tris pH 8.5, 100 mM NaCl, 5 mM MgCl$_2$, and 20 μM ZnCl$_2$) (3×). The resin was resuspended in 1.5 mL of staining buffer in a petri dish and 150 μL of a 5-bromo-4-chloro-3-indolyl-phosphate (BCIP) solution (5 mg/mL) was added. After 30 minutes, 50 μL of 1 M HCl was added to quench the reaction and the intensely turquoise positive beads were isolated under a dissecting microscope. The sequences of hit beads were determined using partial Edman degradation-mass spectrometry (PED-MS) as previously described in Thakkar et al. (Anal. Chem. 2006, 78, 5935-5939), which is incorporated by reference herein in its entirety.

The resulting peptide sequences in the A ring were constructed through combinatorial synthesis using a set of 24 proteinogenic and unnatural amino acids (e.g., D-amino acids). The 12 CPP sequences consisted of different combinations of two or three aromatic hydrophobic residues (L- or D-Phe and L- or D-naphthylalanine) and three or four L- or D-arginine residues and were prepared by parallel synthesis. Because the NEMO surface near the IKK-binding site is negatively charged (vide infra), in addition to ensuring cell penetration, some of the positively charged CPP sequences might also interact electrostatically with the negatively charged NEMO surface. The bicyclic library has a theoretical diversity of 2.4×10$^9$ and was synthesized on 130-μm TentaGel beads in the one bead-two compound (OBTC) format, with each bead displaying a unique bicyclic peptide on its surface layer and a linear peptide of identical sequence in its inner layer as an encoding tag. The library design also included a propargylglycine-β-alanine-hydroxylmethylbenzoyl ester (Pra-B-Hmb) linker, which was intended for selective on-bead fluorescent labeling and release of the bicyclic peptide for an additional round of in-solution screening, although the latter turned out to be unnecessary.

Approximately 600 mg of the library (about 600,000 different compounds) was screened for binding to NEMO in two different rounds as detailed under Methods, resulting in 12 unique hit sequences. Ten of these 12 peptides were resynthesized and tested for inhibition of the NEMO-IKKβ interaction by using a homogeneous time-resolved fluorescence (HTRF) assay. All 10 peptides inhibited the NEMO-IKKβ interaction with IC50 values of 3.4-28 µM. The three most potent compounds were labelled with fluorescein and their cellular uptake into HeLa cells was quantitated by flow cytometry analysis. All three peptides were cell-permeable and had similar cell entry efficiency. Peptide 2 (Table 5) was selected for further optimization, because it showed the highest potency in the HTRF assay, with an IC50 value of 3.4 µM (FIG. 2A).

For flow cytometry analysis, HeLa cells were seeded into 12-well plates ($1.5 \times 10^5$ cells per well) 24 hours before treatment. The next day, 5 µM FITC-labeled peptide in DMEM containing 10% FBS was added to each well and allowed to incubate at 37° c. for 2 hours. After compound treatment, the cells were washed with DPBS, detached from the plate with trypsin (0.25%), diluted in DMEM containing 10% FBS and pelleted at 250 g for 5 min. This washing process was repeated once to remove any free compound and left over trypsin. The washed pellet was resuspended in DPBS with 1% FBS and analyzed on a BD LSR II flow cytometer. Data presented were the mean±SD of three independent experiments.

Recombinant GST-NEMO (20 nM), biotin-IKKβKK/RR (701-745) (50 nM), streptavidin labeled with d2 acceptor (2.5 µg/mL), anti-GST monoclonal antibody labeled with Tb donor (2.5 µg/mL), and varying concentrations of peptide (0-100 µM) were mixed in PBS containing 1 mM TCEP and 0.01% Triton X-100 (total volume 20 µL) in a 384-well plate. The plate was incubated for 2 hOURS at room temperature to establish an equilibrium. The HTRF signals were measured on a Tecan Infinite M1000 Pro microplate reader and plotted as a function of the peptide concentration. The data was analyzed using GraphPad Prism 6.0 and IC50 values were obtained by fitting the data to the dose-response inhibition curves. Data presented were the mean±SD of three independent experiments.

In general, for protein expression and purification, *Escherichia coli* BL21(DE3) cells were transformed with a pGEX4T3-NEMO(1-196) plasmid and grown at 37° C. in Luria broth supplemented with 0.05 mg/mL ampicillin to an OD600 of 0.4. Expression of GST-NEMO was induced by the addition of isopropyl β-D-1-thiogalactopyranoside (150 µM final concentration). After five hours at 30° C., the cells were harvested by centrifugation. The cell pellet was suspended in 40 mL of lysis buffer (50 mM Tris-HCl, 100 mM NaCl, 0.5 mM MgCl2, 5 mM β-mercaptoethanol, 0.1% Triton-X-100, pH 8.0), 100 µg/mL lysozyme, 100 µL of DNAse I (New England BioLabs), and 100 µL of Halt Protease Inhibitor Cocktail (EDTA-free) (Thermo Scientific). This mixture was stirred at 4° C. for 30 min and briefly sonicated (2×10 s pulses). The crude lysate was centrifuged to yield a clear supernatant, which was directly loaded onto a glutathione-Sepharose 4B column (GE Healthcare). The bound protein was eluted from the column with 10 mM glutathione in 50 mM Tris-HCl (pH 8.0), concentrated to 0.5 mL with the use of Amicon Ultra-15 centrifugal filter units (MWCO 10 kDa), and dialyzed against PBS before flash freezing.

An engineered prokaryotic expression plasmid pJCC04a, which encodes a fusion protein containing an N-terminal six-histidine tag, thioredoxin, a TEV protease cleavage site, and the K703R/K704R mutant form of IKKβ C-terminal fragment (amino acids 701-745) [His-thx-IKKbKK/RR (701-745)]. His-thx-IKKbKK/RR(701-745) was similarly expressed in *E. coli* BL21 (DE3) cells and purified by affinity chromatography using a HisTrap FF column (GE Healthcare). The fusion protein was eluted with 50 mM Tris-HCl (pH 8.0), 300 mM NaCl, 250 mM imidazole, 2 mM β-mercaptoethanol and treated with TEV protease (150 units for 1 mg of fusion protein) for 16 hours at 4° C. to remove the thioredoxin (thx). The resulting protease digestion mixture was reloaded onto the HisTrap column. The flow-through fraction was collected and concentrated to about 2 mg/mL using Amicon Ultra-15 centrifugal filter units (MWCO 10 kDa). The IKKbKK/RR(701-745) peptide was biotinylated by treatment with a 10-fold molar excess of biotin-NHS at 4° C. overnight. The biotinylated IKKbKK/RR(701-745) was purified by reversed-phase HPLC equipped with a C18 column and stored frozen at −80° C.

In addition, a medicinal chemistry campaign was conducted to investigate the NEMO-binding affinity and/or cell-permeability of peptide 2. In brief, we first modified the CPP motif in the B ring to improve cellular uptake. Addition of a 4th arginine to the CPP motif, either inside (Table 5, peptide 3) or outside the B ring (peptides 4 and 5) slightly decreased the cellular entry efficiency. Replacement of the second arginine with D-arginine increased the uptake efficiency by 4.2-fold (peptide 6). Therefore, FΦRrR (where Φ is L-naphthylalanine and r is D-arginine (SEQ ID NO: 66)) was chosen as the CPP motif and modified the A ring to improve the NEMO-binding affinity. Insertion of an Ala immediately N-terminal to the internal Dap residue (with the intention of creating an additional site of diversification) increased the binding affinity by 5.9-fold (IC50=1.0 µM for peptide 7; FIGS. 1 and 2A-2E).

In a fluorescence anisotropy (FA) assay, fluorescently labeled peptide 7 bound directly to NEMO with a KD value of 220±80 nM, but only weakly to a panel of control proteins (KD>10 The proteolytic stability of peptide 7 was assessed by incubation in human serum at 37° C. and quantitation of the remaining peptide as a function of time by analytical HPLC. Peptide 7 showed minimal degradation (<1%) after 20 hours of incubation. Under the same conditions, Antp-NBD (Table 5, peptide 1) was rapidly degraded with a half-life of about 20 minutes. Given its excellent proteolytic stability and respectable potency and cell permeability (163% relative to CPP1, a previously reported and relatively efficient cyclic CPP; FIGS. 2A and 2b), we selected peptide 7 (FIG. 1) for further characterization.

To gain insight into how peptide 7 interacts with NEMO, in silico docking of peptide 7 to the NEMO protein was performed. The all-atom 3D structure of peptide 7 was prepared in Maestro from the 2D structure (Schrodinger, LLC ver. 11.1) and relaxed using Polak-Ribier conjugate gradient minimization to resolve steric and torsional strain introduced during conversion. To account for the complex conformational landscape of a bicyclic peptide, a conformational ensemble of structures was obtained for peptide 7 using molecular dynamics. In brief, peptide 7 was parameterized using the OPLS3 force-field and then solvated in an orthorhombic periodic box containing 1867 TIP3P water molecules. The system was neutralized with the addition of three Cl⁻ ions and then simulated for 1 ns at 303 K and 1.01 MPa, controlled using the Nose-Hoover thermostat and Martyna-Tobias-Klein barostat, respectively, through the Desmond software package. Structures corresponding to every 10 ps of the simulation were extracted using the Trajectory tool in Maestro. To ensure that the ensemble contains a diverse selection of initial compound geometries, the molecular dynamics structures were passed through the Macrocycle Conformational Sampling tool in MacroModel using the OPLS3 force-field. Generalized Born/Solvent Area water electrostatics were applied, sampling across a temperature range from 300 K to 1000 K using a global low-mode search over 50 simulation cycles. Redundant conformers (defined as a heavy-atom RMSD of <0.75 Å) were rejected, yielding an ensemble of 105 structures spanning an energy range of 20 kcal/mol, which were carried forward for docking.

The receptor was prepared from the reported crystal structure of a NEMO dimer (PDBID: 3V3B), by removing co-crystallized solvent and reconstructing incomplete side-chains using Prime (Schrodinger LLC). The binding site was defined as a 20-Å cube centered on the geometric mean of receptor residues Leu-93, Phe-97 and Val-104. Rigid-receptor/flexible-ligand docking was performed using extra-precision mode in Glide. Ligand flexibility was accounted for by applying a scaling factor of 0.8 to ligand atom van der Waals radii and the generation of 100,000 poses per ligand sampled, for a theoretical total of 100,000,000 poses sampled for peptide 7 during the combined docking runs. Top scoring poses were subjected to a brief round of energy minimization using Embrace (Schrodinger LLC) to remove any steric clashes resulting from van der Waals' radii scaling during docking. The final poses were analyzed and electrostatic potential surfaces generated using UCSF Chimera.

The best-scoring binding pose of peptide 7 shown in FIGS. 3A-3C. Peptide 7 binds to the canonical IKK-binding site on NEMO, with the peptide A ring partially inserted into a hydrophobic groove normally occupied by the NBD of IKKβ. The side chain of Tyr-4 is deeply inserted into a large hydrophobic pocket and excluded from the sol-vent (FIG. 3B). Ile-3 interacted intimately with a shallow hydrophobic pocket on the NEMO surface, whereas Trp-2 made surface contacts primarily through the pyrrole ring while the benzene ring was mostly solvent exposed.

The B ring (CPP ring) of peptide 7 made important interactions with NEMO. The three arginine residues of the CPP motif interact electrostatically with the acidic patch next to the NBD binding groove (FIG. 3B). Phe-7, which is a part of the CPP motif, was completely buried and made hydrophobic interaction with NEMO. Nal-8 was almost completely solvent exposed, although the naphthalene ring may make hydrophobic interactions with the NEMO surface.

To assess the validity of the molecular modeling results, we performed an "alanine scan" of peptide 7 by replacing each residue with an alanine (or D-alanine) and determining the IC50 values of the resulting peptides against the NEMO-IKKβ interaction (Table 5, peptides 11-19). Consistent with the modeling results, replacement of Trp-2, Ile-3, or Tyr-4 in the A ring with alanine significantly decreased the potency of the inhibitor (by 2- to 3-fold for peptides 12-14).

Substitution of Ala for Phe-7 (peptide 15), Nal-8 (peptide 16), or D-Arg at position 10 (peptide 18) also significantly de-creased the NEMO-binding affinity. Thus, both molecular modeling and alanine-scan results indicate that the CPP motif in the B ring also interacts with the NEMO protein and contributes to the overall binding affinity and specificity of peptide 7.

Based on the SAR data, we generated two negative control peptides by replacing two (Trp-2 and Tyr-4) or three of the NEMO-binding residues in the A ring (Trp-2, Ile-3, and Tyr-4) with Ala. The resulting peptides (peptides 20 and 21) have similar cellular entry efficiencies to peptide 7, but 16- and >100-fold lower NEMO-binding affinity, respectively (FIGS. 2A and 2B and Table 5). In general, the bicyclic peptide library strategy developed in this work should be applicable to the discovery of cell-permeable bicyclic peptides against numerous intracellular targets.

TABLE 5

Sequences, NEMO-binding affinities, and cell-permeability of peptide.

| Peptide ID | SEQ ID NO: | Sequence | IC$_{50}$ (μM) | Permeability (%) |
|---|---|---|---|---|
| 1 | 138 | RQIKIWPQNRRMKWKKGGTALDWSWLQTE | >40 | 35 |
| 2 | 139 | Tm(GWIY)Δ(FΦRRRΔ)-BBK | 3.4 ± 0.6 | 76 |
| 3 | 140 | Tm(GWIY)Δ(FΦRRRRΔ)-BBK | 1.5 ± 0.2 | 55 |
| 4 | 141 | Tm(GWIY)Δ(FΦRRRA)-RBK | 1.8 ± 0.3 | 71 |
| 5 | 142 | Tm(GWIY)Δ(FΦRRRA)-rBK | 1.3 ± 0.4 | 71 |
| 6 | 143 | Tm(GWIY)Δ(FΦRrRΔ)-BBK | 5.9 ± 0.6 | 322 |
| 7 | 144 | Tm(GWIYA)Δ(FΦRrRΔ)-BBK | 1.0 ± 0.1 | 163 |
| 8 | 145 | Tm(GWIYa)Δ(FΦRrRΔ)-BBK | 2.9 ± 0.1 | |
| 9 | 146 | Tm(AGWIY)Δ(FΦRrRΔ)-BBK | 2.2 ± 0.1 | |
| 10 | 147 | Tm(aGWIY)Δ(FΦRrRΔ)-BBK | 2.3 ± 0.3 | |
| 11 | 148 | Tm(AWIYA)Δ(FΦRrRΔ)-BBK | 1.2 ± 0.2 | |
| 12 | 149 | Tm(GAIYA)Δ(FΦRrRΔ)-BBK | 3.0 ± 0.3 | |
| 13 | 150 | Tm(GWAYA)Δ(FΦRrRΔ)-BBK | 1.7 ± 0.1 | |
| 14 | 151 | Tm(GWIAA)Δ(FΦRrRΔ)-BBK | 2.8 ± 0.3 | |

TABLE 5-continued

Sequences, NEMO-binding affinities, and cell-permeability of peptide.

| Peptide ID | SEQ ID NO: | Sequence | IC$_{50}$ (μM) | Permeability (%) |
|---|---|---|---|---|
| 15 | 152 | Tm(GWIYA)Δ(AΦRrRΔ)-BBK | 1.9 ± 0.2 | |
| 16 | 153 | Tm(GWIYA)Δ(FARrRΔ)-BBK | 2.8 ± 0.2 | |
| 17 | 154 | Tm(GWIYA)Δ(FΦArRΔ)-BBK | 1.1 ± 0.3 | |
| 18 | 155 | Tm(GWIYA)Δ(FΦRaRΔ)-BBK | 2.1 ± 0.2 | |
| 19 | 156 | Tm(GWIYA)Δ(FΦRrAΔ)-BBK | 1.2 ± 0.2 | |
| 20 | 157 | Tm(GAIAA)Δ(FΦRrRΔ)-BBK | 16 ± 2 | 176 |
| 21 | 158 | Tm(GAAAA)Δ(FΦRrRΔ)-BBK | >100 | 110 |

Tm, trimesic acid; Δ, L-2,3-diaminopropionic acid, Φ, L-2-naphthylalanine; B, L-β-alanine; r, D-arginine.
See FIG. S$_1$ for detailed structures.
Cell-permeability values are relative to that of CPP$_1$ (100%).

Example 2. Inhibition of NF-κB Signaling by Bicyclic Peptidyl Inhibitors

The ability of the bicyclic peptidyl inhibitors to inhibit NF-κB Signaling was analyzed. The ability of peptide 7 to enter the cell and block the intracellular NEMO-IKK interaction was assessed by using HEK293(Luc) cells, which harbor a luciferase gene under the transcriptional control of NF-κB. For the NF-κB Luciferase Assays, culture media was exchanged for DMEM containing 10% FBS and 1% penicillin/streptomycin the day before seeding to remove hygromycin B. HEK293(Luc) cells were seeded in 50 μL of assay medium (DMEM, 10% FBS, and 1% penicillin/streptomycin) in an opaque 96-well microplate (3000 cells per well) and incubated overnight. The peptide inhibitors were added to the cells the next day in 5 μL of assay medium and the plate was incubated at 37° c. for 2 h. After that, 5 μL of assay media containing recombinant TNFα (final concentration 5 ng/mL) was added to the wells. The plate was then returned to the incubator for 4 h at 37° c. Finally, 50 μL of ONE-Step luciferase assay reagent was added to each well and after 10 minutes the luminescence was measured on a Tecan Infinite M1000 Pro microplate reader. Data presented were the mean±SD of at least three independent experiments (n=6 for basal activities).

In the absence of any inhibitor, treatment of HEK 293 (Luc) cells with TNFα activated the IKK complex and nuclear translocation of NF-κB, resulting in a 15-fold increase in the luciferase activity (FIG. 2C). Prior incubation of the cells with peptide 7 dose-dependently inhibited the TNFα-induced NF-κB activation with an IC$_{50}$ value of 10 μM (FIGS. 2C and 2D). Antp-NBD (peptide 1) also inhibited NF-κB activation, but with an IC$_{50}$ of about 41 μM, in agreement with previous reports. The two negative control peptides (peptide 20 and peptide 21) decreased the luciferase activity only at high concentrations.

It is to be noted that at very high concentrations, cationic CPPs may cause nonspecific cytotoxicity to mammalian cells and reduce the expression of the luciferase gene. Further, at high concentrations (>10 μM), CPPs can directly cross the plasma membrane through a yet poorly defined "direct translocation" mechanism, in addition to endocytic uptake, resulting in much greater cytosolic entry efficiency. Both factors may cause artificially low cellular IC$_{50}$ values in the luciferase assay for poorly active peptides (such as Antp-NBD, peptide 20 and peptide 21). As discussed earlier, NEMO is not involved in the non-canonical NF-κB signaling pathway. A specific inhibitor against NEMO should not block the basal NF-κB activity, which has important physiological functions.

To test whether peptide 7 also affects the basal NF-κB activity, the luciferase assay was repeated in the absence of TNFα stimulation. As shown in FIG. 2C, peptide 7 did not inhibit the basal NF-κB activity. Instead, it caused a small but statistically significant increase in the basal NF-κB activity (about 1.5-fold). Such a small stimulatory effect was previously reported for Antp-NBD and attributed to increased availability of IKKα/β for the non-canonical NF-κB signaling pathway when the canonical pathway is blocked. To ascertain that inhibition of NF-κB signaling by peptide 7 is caused by disruption of the NEMO-IKK interaction, we treated HT29 colon cancer cells with peptide 7 and TNFα and examined the levels of phosphorylated (and activated) IKKβ and IκBα, which acts immediately downstream of the NEMO-IKK complex, by western blot analysis.

As expected, peptide 7 (0-25 μL) dose-dependently inhibited TNFα-induced phosphorylation of IKKβ, while the total intracellular IKKβ level was unchanged (FIG. 2E). For immunoblot analysis, HT29 cells were grown in a 6-well plate to 80-90% confluency in standard DMEM (Life Technologies) supplemented with 10% FBS and 1% penicillin-streptomycin sulfate at 37° C. in 5% CO2. The cells were treated with 0, 2, 10, or 25 μM peptide 7 for 2 hours followed by stimulation with TNFα (5 ng/ml) for 10 minutes. The cells were rapidly washed with cold PBS and trypsinized to detach from the plate. Following centrifugation and resuspension in PBS to remove any remaining trypsin the pelleted cells were lysed in 100 μl of Pierce™ RIPA Buffer (Thermo) containing protease and phosphatase inhibitors for 30 minutes on ice. Cell lysates were centrifuged at 15000 rpm for 20 minutes, and the extracted proteins in the supernatant were collected. After measuring the concentration of the samples using the BCA Protein Assay Kit (Thermo) and adjusting the total protein concentration to be the same for each sample, SDS-PAGE loading buffer was added and the samples were boiled for 5 minutes. Equal amounts of protein were loaded onto a 10% SDS-PAGE gel (130 V, 2.5 hours)

followed by electrophoretic transfer to a nitrocellulose membrane at 4° C. (90 V, 2.5 hours). The membrane was blocked using TBST buffer (20 mM Tris pH 7.5, 150 mM NaCl, 0.1% (v/v) Tween-20) containing 5% milk proteins (Bio-Rad) at room temperature for 1 h and finally the membrane was probed with the following rabbit monoclonal antibodies: p-IKKα (Ser176)/IKKβ (Ser177) (Cell Signaling Technologies, 2071), IKKβ (Cell Signaling Technologies, 8943), IκBα (Cell Signaling Technologies, 4812), and β-Actin (Sigma, A5441). Primary antibodies were diluted according to the suggestion of the manufacturer and incubated with the nitrocellulose mem-brane overnight at 4° C. After washing, the appropriate HRP conjugated secondary antibody was added to each membrane and incu-bated at room temperature for 2 hours. The membrane was washed with TBST solution again and the signals were detected with the Chemiluminescent HRP Antibody Detection Reagent (Denville, E-2500) by following the manufacturer's protocol.

Concomitantly, peptide 7 increased the intracellular level of IκBα, presumably by inhibiting TNFα-induced proteasomal degradation. The same effects on NF-κB signaling had previously been reported for Antp-NBD. In agreement with the luciferase assay results (FIG. 2C), peptide 7 showed no effect on the phospho-IKKβ or IκBα level when cells were not stimulated with TNFα. Taken together, the above results indicate that peptide 7 efficiently enters the cytosol of mammalian cells and selectively inhibits the canonical NF-κB signaling pathway by blocking the NEMO-IKK interaction.

In general, peptide 7 selectively inhibits the canonical NF-κB signaling pathway but not the non-canonical NF-κB pathway. Consequently, peptide 7 inhibits the proliferation and survival of cancer cells with elevated NF-κB activities but has minimal cytotoxicity to normal cells. We have demonstrated the feasibility of designing cell-permeable bicyclic peptides whose CPP motif performs the dual function of cell penetration and target engagement. This strategy results in biologically active macrocycles that are relatively small in size and have more "drug-like" properties.

Example 3. Anticancer Activity by Bicyclic Peptidyl Inhibitors

The anticancer activity of the bicyclic peptidyl inhibitors was analyzed. Aberrant activation of NF-κB via the canonical signaling pathway plays critical roles during the initiation and progression of certain cancers. For example, NF-κB is excessively activated in ovarian cancer cell lines A2780 and CP70. Moreover, blocking canonical NF-κB activation in A2780 cells resulted in apoptosis. We therefore tested peptide 7 for potential anticancer activity against cell lines with hyperactivated NF-κB. We first examined the entry of peptide 7 into A2780 ovarian cancer cells by live-cell confocal microscopy. For confocal microscopy, A2780 cells were seeded into a glass-bottomed culture dish (MatTek) and cultured overnight at 37° c. ($5 \times 10^4$ cells/mL). The next day the cells were washed with DPBS (2×) and treated with 5 μM fluorescein-labeled peptide in RPMI media containing 10% FBS, and incubated at 37° c. for 2 h. The media containing the peptide was removed and the cells were washed twice with phenol-free RPMI media (2×). The cells were imaged on a Visitech Infinity 3 Hawk 2D-array live cell imaging confocal microscope equipped with a 60× oil objective.

Treatment of the cells with 5 μM FITC-labeled peptide 7 for 2 h resulted in intense green fluorescence inside all cells (FIG. 4A). Next, the effect of pep-tide 7 on the viability of A2780 and CP70 cells was assessed by a methylene blue cell viability assay. For the methylene blue cell viability assay, A2780 (2500 cells/well), CP70 (2000 cells/well) or OSE (3000 cells/well) were seeded into a 96-well microplate in 100 μL respective growth media and incubated at 37° c. overnight. The following day, the seeded cells were treated with increasing concentrations of peptide for 72 hours. The treated cells were washed with DPBS and fixed to the plate by treating with 3.7% formaldehyde solution for 1 hour. Fixation solution was removed and the fixed cells were treated with 1.0% methylene blue solution for 30 minutes. Following staining, the plate was rinsed under running water for approximately five min and left to dry. Finally, 100 μL of solubilization buffer (10% acetic acid, 50% methanol, and 40% $H_2O$) was added to each well and the absorbance was measured at 630 nm using a Tecan Infinite M1000 Pro microplate reader. Data presented were the mean±SD of five independent experiments.

Peptide 7 dose-dependently reduced the viability of both ovarian cancer cell lines, with LD50 values of about 20 and 10 μM for A2780 and CP70 cells, respectively (FIG. 4B). In contrast, peptide 7 had no significant effect on ovarian surface epithelial cells (OSE), a non-cancerous ovarian cell line with normal NF-κB activity. The greater sensitivity of CP70 cells to peptide 7 than A2780 cells is consistent with the greater dependency on NF-κB activity by the former. CP70 cells were derived from A2780 cells by subjecting the latter to low, repeated doses of cisplatin and selecting for cisplatin resistant clones. Peptide 7 also reduced the viability of A375 melanoma cells, which have constitutively activated NF-κB. The treatment of A375 cells with Antp-NBD decreased the NF-κB activity and induced growth arrest and apoptosis was previously disclosed in Ianaro et al. (Cancer Lett. 2009, 274, 331-336), which contents is incorporated by reference in its entirety.

To determine whether the observed anticancer activity of peptide 7 is correlated with specific inhibition of the NEMO-IKK interaction, we also tested the effect of peptides 1, 20, and 21 on A2780 cells by using the MTT cell viability assay. For the MTT cell viability assay, HeLa, HEK293, A2780, OSE or A375 cells were seeded into a 96-well microplate (3000 cells/well) in 100 μl of respective growth media and incubated at 37° c. overnight. The next day, a serial dilution of peptide was added to each well in 10 μL of assay medium. The treated cells were incubated at 37° c. with 5% CO2 for 72 hours. Following compound treatment, 10 μL of MTT stock solution (Roche) was added to each well. After an additional 4 h at 37° C., 100 μL of SDS-HCl solubilizing solution was added to each well and the plate was returned to the incubator overnight at 37° c. A Tecan Infinite M1000 Pro microplate reader was used the following morning to measure the absorbance of the formazan product at 565 nm. Data presented were the mean±SD of three independent experiments.

Although Antp-NBD also reduced the viability of A2780 cells in a dose-dependent manner, it was less active than peptide 7 (LD50 values of about 30 μM and >80 μM for peptide 7 and Antp-NBD, respectively; FIG. 4C). This is consistent with the fact that Antp-NBD is less potent in NEMO binding, less cell-permeable, and less metabolically stable than peptide 7. As expected, peptides 20 and 21 were also much less active than peptide 7 in this assay. Under the same conditions, none of the four peptides had significant effect on the viability of non-cancerous OSE cells (FIG. 4D). These results strongly suggest that the observed anticancer activity of peptide 7 (and Antp-NBD) is caused by their inhibition of the NEMO-IKK interaction and NF-κB activation.

INCORPORATION BY REFERENCE

All publications cited herein are incorporated by reference in its entirety for all purposes.

The invention claimed is:

1. A bicyclic polypeptide according to Formula 1A or 1B:

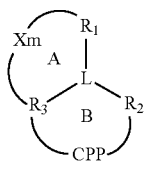
(1A)

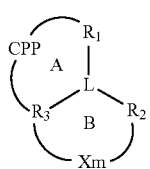
(1B)

wherein:
CPP is a cell-penetrating peptide sequence selected from any one of SEQ ID NO.: 11-48 or 66-99;
Xm is a peptide sequence that binds NF-κB essential modulator (NEMO) protein and is a 4-7 amino acid sequence comprising a sequence selected from any one of GWIY (SEQ ID NO: 1); GWIYA (SEQ ID NO:2); GWIYa (SEQ ID NO:50); AGWIY (SEQ ID NO:3); aGWIY (SEQ ID NO:51); AWIYA (SEQ ID NO:4); GAIYA (SEQ ID NO:5); GWAYA (SEQ ID NO: 6); GWIAA (SEQ ID NO:7); GWIYA (SEQ ID NO:8); GAIAA (SEQ ID NO:9); and GAAAA (SEQ ID NO:10), and the inverse of the aforementioned Xm sequences (SEQ ID Nos: 52-63);
L is a linker moiety; and
each of $R_1$, $R_2$, and $R_3$ are independently, a bonding moiety,
wherein the bonding moiety is formed when Xm, CPP, or a combination thereof, covalently bind to L to form the bicyclic polypeptide.

2. A bicyclic polypeptide according to Formula 1C or 1D:

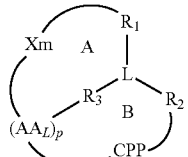
(1C)

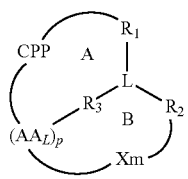
(1D)

wherein:
CPP is a cell-penetrating peptide sequence selected from any one of SEQ ID NO.: 11-48 or 66-99;
Xm is a peptide sequence that binds to a NF-κB essential modulator (NEMO) protein and is a 4-7 amino acid sequence comprising a sequence selected from any one of GWIY (SEQ ID NO:1); GWIYA (SEQ ID NO:2); GWIYa (SEQ ID NO:50); AGWIY (SEQ ID NO:3); aGWIY (SEQ ID NO:51); AWIYA (SEQ ID NO:4); GAIYA (SEQ ID NO:5); GWAYA (SEQ ID NO:6); GWIAA (SEQ ID NO:7); GWIYA (SEQ ID NO:8); GAIAA (SEQ ID NO:9); and GAAAA (SEQ ID NO: 10), and the inverse of the aforementioned Xm sequences (SEQ ID Nos: 52-63);
$AA_L$ at each instance is an amino acid;
p is selected from a number from 0 to 3;
L is a linker moiety; and
each of $R_1$, $R_2$, and $R_3$ are independently, a bonding moiety,
wherein the bonding moiety is formed when Xm, CPP, or a combination thereof, covalently bind to L to form the bicyclic polypeptide.

3. The bicyclic polypeptide of claim 1, wherein both the CPP sequence and the Xm sequence participate in binding to NEMO.

4. The bicyclic polypeptide of claim 1, wherein the polypeptide binds to the IKKα/β-binding domain on NEMO.

5. The bicyclic polypeptide of claim 1, wherein the polypeptide inhibits NEMO-IKKα/β interaction by at least about 10%.

6. The bicyclic polypeptide of claim 1, wherein the polypeptide has an IC50 of about 10 UM or less when measured for the NEMO-IKKα/β interaction.

7. The bicyclic polypeptide of claim 1, wherein the polypeptide has an IC50 of about 1.0 uM or less when measured for the NEMO-IKKα/β interaction.

8. The bicyclic polypeptide of claim 1, wherein each of $R_1$, $R_2$, and $R_3$ are independently selected from an amide, an ester, and triazole, and combinations thereof.

9. A pharmaceutical composition comprising the bicyclic polypeptide of claim 1 and one or more pharmaceutically acceptable excipients.

* * * * *

SEQUENCE LISTING

```
Sequence total quantity: 158
SEQ ID NO: 1                 moltype = AA  length = 4
FEATURE                      Location/Qualifiers
REGION                       1..4
                             note = synthetic construct
source                       1..4
                             mol_type = protein
                             organism = synthetic construct
SEQUENCE: 1
GWIY                                                                        4

SEQ ID NO: 2                 moltype = AA  length = 5
FEATURE                      Location/Qualifiers
REGION                       1..5
                             note = synthetic construct
source                       1..5
                             mol_type = protein
                             organism = synthetic construct
SEQUENCE: 2
GWIYA                                                                       5

SEQ ID NO: 3                 moltype = AA  length = 5
FEATURE                      Location/Qualifiers
REGION                       1..5
                             note = synthetic construct
source                       1..5
                             mol_type = protein
                             organism = synthetic construct
SEQUENCE: 3
AGWIY                                                                       5

SEQ ID NO: 4                 moltype = AA  length = 5
FEATURE                      Location/Qualifiers
REGION                       1..5
                             note = synthetic construct
source                       1..5
                             mol_type = protein
                             organism = synthetic construct
SEQUENCE: 4
AWIYA                                                                       5

SEQ ID NO: 5                 moltype = AA  length = 5
FEATURE                      Location/Qualifiers
REGION                       1..5
                             note = synthetic construct
source                       1..5
                             mol_type = protein
                             organism = synthetic construct
SEQUENCE: 5
GAIYA                                                                       5

SEQ ID NO: 6                 moltype = AA  length = 5
FEATURE                      Location/Qualifiers
REGION                       1..5
                             note = synthetic construct
source                       1..5
                             mol_type = protein
                             organism = synthetic construct
SEQUENCE: 6
GWAYA                                                                       5

SEQ ID NO: 7                 moltype = AA  length = 5
FEATURE                      Location/Qualifiers
REGION                       1..5
                             note = synthetic construct
source                       1..5
                             mol_type = protein
                             organism = synthetic construct
SEQUENCE: 7
GWIAA                                                                       5

SEQ ID NO: 8                 moltype = AA  length = 5
FEATURE                      Location/Qualifiers
REGION                       1..5
                             note = synthetic construct
source                       1..5
                             mol_type = protein
                             organism = synthetic construct
```

-continued

```
SEQUENCE: 8
GWIYA                                                                             5

SEQ ID NO: 9              moltype = AA  length = 5
FEATURE                   Location/Qualifiers
REGION                    1..5
                          note = synthetic construct
source                    1..5
                          mol_type = protein
                          organism = synthetic construct
SEQUENCE: 9
GAIAA                                                                             5

SEQ ID NO: 10             moltype = AA  length = 5
FEATURE                   Location/Qualifiers
REGION                    1..5
                          note = synthetic construct
source                    1..5
                          mol_type = protein
                          organism = synthetic construct
SEQUENCE: 10
GAAAA                                                                             5

SEQ ID NO: 11             moltype = AA  length = 7
FEATURE                   Location/Qualifiers
REGION                    1..7
                          note = synthetic construct
source                    1..7
                          mol_type = protein
                          organism = synthetic construct
SEQUENCE: 11
CRRRRFW                                                                           7

SEQ ID NO: 12             moltype = AA  length = 7
FEATURE                   Location/Qualifiers
REGION                    1..7
                          note = synthetic construct
source                    1..7
                          mol_type = protein
                          organism = synthetic construct
SEQUENCE: 12
URRRRFW                                                                           7

SEQ ID NO: 13             moltype = AA  length = 7
FEATURE                   Location/Qualifiers
REGION                    1..7
                          note = synthetic construct
source                    1..7
                          mol_type = protein
                          organism = synthetic construct
SEQUENCE: 13
CRRRRFW                                                                           7

SEQ ID NO: 14             moltype = AA  length = 5
FEATURE                   Location/Qualifiers
REGION                    1..5
                          note = synthetic construct
source                    1..5
                          mol_type = protein
                          organism = synthetic construct
SEQUENCE: 14
FWRRR                                                                             5

SEQ ID NO: 15             moltype = AA  length = 5
FEATURE                   Location/Qualifiers
REGION                    1..5
                          note = synthetic construct
source                    1..5
                          mol_type = protein
                          organism = synthetic construct
SEQUENCE: 15
RRRWF                                                                             5

SEQ ID NO: 16             moltype = AA  length = 5
FEATURE                   Location/Qualifiers
REGION                    1..5
                          note = synthetic construct
source                    1..5
                          mol_type = protein
```

```
                          -continued organism = synthetic construct
SEQUENCE: 16
FFRRR                                                                    5

SEQ ID NO: 17          moltype = AA  length = 5
FEATURE                Location/Qualifiers
REGION                 1..5
                       note = synthetic construct
source                 1..5
                       mol_type = protein
                       organism = synthetic construct
SEQUENCE: 17
FRFRR                                                                    5

SEQ ID NO: 18          moltype = AA  length = 5
FEATURE                Location/Qualifiers
REGION                 1..5
                       note = synthetic construct
source                 1..5
                       mol_type = protein
                       organism = synthetic construct
SEQUENCE: 18
FRRFR                                                                    5

SEQ ID NO: 19          moltype = AA  length = 5
FEATURE                Location/Qualifiers
REGION                 1..5
                       note = synthetic construct
source                 1..5
                       mol_type = protein
                       organism = synthetic construct
SEQUENCE: 19
FRRRF                                                                    5

SEQ ID NO: 20          moltype = AA  length = 5
FEATURE                Location/Qualifiers
REGION                 1..5
                       note = synthetic construct
source                 1..5
                       mol_type = protein
                       organism = synthetic construct
SEQUENCE: 20
FFFRA                                                                    5

SEQ ID NO: 21          moltype = AA  length = 5
FEATURE                Location/Qualifiers
REGION                 1..5
                       note = synthetic construct
source                 1..5
                       mol_type = protein
                       organism = synthetic construct
SEQUENCE: 21
FFFRR                                                                    5

SEQ ID NO: 22          moltype = AA  length = 6
FEATURE                Location/Qualifiers
REGION                 1..6
                       note = synthetic construct
source                 1..6
                       mol_type = protein
                       organism = synthetic construct
SEQUENCE: 22
FFRRRR                                                                   6

SEQ ID NO: 23          moltype = AA  length = 6
FEATURE                Location/Qualifiers
REGION                 1..6
                       note = synthetic construct
source                 1..6
                       mol_type = protein
                       organism = synthetic construct
SEQUENCE: 23
FRRFRR                                                                   6

SEQ ID NO: 24          moltype = AA  length = 6
FEATURE                Location/Qualifiers
REGION                 1..6
                       note = synthetic construct
source                 1..6
```

```
                        mol_type = protein
                        organism = synthetic construct
SEQUENCE: 24
FRRRFR                                                                    6

SEQ ID NO: 25           moltype = AA   length = 6
FEATURE                 Location/Qualifiers
REGION                  1..6
                        note = synthetic construct
source                  1..6
                        mol_type = protein
                        organism = synthetic construct
SEQUENCE: 25
RFFRRR                                                                    6

SEQ ID NO: 26           moltype = AA   length = 6
FEATURE                 Location/Qualifiers
REGION                  1..6
                        note = synthetic construct
source                  1..6
                        mol_type = protein
                        organism = synthetic construct
SEQUENCE: 26
RFRRFR                                                                    6

SEQ ID NO: 27           moltype = AA   length = 6
FEATURE                 Location/Qualifiers
REGION                  1..6
                        note = synthetic construct
source                  1..6
                        mol_type = protein
                        organism = synthetic construct
SEQUENCE: 27
FRFRRR                                                                    6

SEQ ID NO: 28           moltype = AA   length = 6
FEATURE                 Location/Qualifiers
REGION                  1..6
                        note = synthetic construct
source                  1..6
                        mol_type = protein
                        organism = synthetic construct
SEQUENCE: 28
FFFRRR                                                                    6

SEQ ID NO: 29           moltype = AA   length = 6
FEATURE                 Location/Qualifiers
REGION                  1..6
                        note = synthetic construct
source                  1..6
                        mol_type = protein
                        organism = synthetic construct
SEQUENCE: 29
FFRRRF                                                                    6

SEQ ID NO: 30           moltype = AA   length = 6
FEATURE                 Location/Qualifiers
REGION                  1..6
                        note = synthetic construct
source                  1..6
                        mol_type = protein
                        organism = synthetic construct
SEQUENCE: 30
FRFFRR                                                                    6

SEQ ID NO: 31           moltype = AA   length = 6
FEATURE                 Location/Qualifiers
REGION                  1..6
                        note = synthetic construct
source                  1..6
                        mol_type = protein
                        organism = synthetic construct
SEQUENCE: 31
RRFFFR                                                                    6

SEQ ID NO: 32           moltype = AA   length = 6
FEATURE                 Location/Qualifiers
REGION                  1..6
                        note = synthetic construct
```

```
source                      1..6
                            mol_type = protein
                            organism = synthetic construct
SEQUENCE: 32
FFRFRR                                                                    6

SEQ ID NO: 33               moltype = AA  length = 6
FEATURE                     Location/Qualifiers
REGION                      1..6
                            note = synthetic construct
source                      1..6
                            mol_type = protein
                            organism = synthetic construct
SEQUENCE: 33
FFRRFR                                                                    6

SEQ ID NO: 34               moltype = AA  length = 6
FEATURE                     Location/Qualifiers
REGION                      1..6
                            note = synthetic construct
source                      1..6
                            mol_type = protein
                            organism = synthetic construct
SEQUENCE: 34
FRRFFR                                                                    6

SEQ ID NO: 35               moltype = AA  length = 6
FEATURE                     Location/Qualifiers
REGION                      1..6
                            note = synthetic construct
source                      1..6
                            mol_type = protein
                            organism = synthetic construct
SEQUENCE: 35
FRRFRF                                                                    6

SEQ ID NO: 36               moltype = AA  length = 6
FEATURE                     Location/Qualifiers
REGION                      1..6
                            note = synthetic construct
source                      1..6
                            mol_type = protein
                            organism = synthetic construct
SEQUENCE: 36
FRFRFR                                                                    6

SEQ ID NO: 37               moltype = AA  length = 6
FEATURE                     Location/Qualifiers
REGION                      1..6
                            note = synthetic construct
source                      1..6
                            mol_type = protein
                            organism = synthetic construct
SEQUENCE: 37
RFFRFR                                                                    6

SEQ ID NO: 38               moltype = AA  length = 7
FEATURE                     Location/Qualifiers
REGION                      1..7
                            note = synthetic construct
source                      1..7
                            mol_type = protein
                            organism = synthetic construct
SEQUENCE: 38
FFFRRRR                                                                   7

SEQ ID NO: 39               moltype = AA  length = 7
FEATURE                     Location/Qualifiers
REGION                      1..7
                            note = synthetic construct
source                      1..7
                            mol_type = protein
                            organism = synthetic construct
SEQUENCE: 39
RFFRRRR                                                                   7

SEQ ID NO: 40               moltype = AA  length = 7
FEATURE                     Location/Qualifiers
REGION                      1..7
```

```
                    note = synthetic construct
source              1..7
                    mol_type = protein
                    organism = synthetic construct
SEQUENCE: 40
RRFFRRR                                                                        7

SEQ ID NO: 41       moltype = AA   length = 7
FEATURE             Location/Qualifiers
REGION              1..7
                    note = synthetic construct
source              1..7
                    mol_type = protein
                    organism = synthetic construct
SEQUENCE: 41
RFFFRRR                                                                        7

SEQ ID NO: 42       moltype = AA   length = 7
FEATURE             Location/Qualifiers
REGION              1..7
                    note = synthetic construct
source              1..7
                    mol_type = protein
                    organism = synthetic construct
SEQUENCE: 42
RRFFFRR                                                                        7

SEQ ID NO: 43       moltype = AA   length = 7
FEATURE             Location/Qualifiers
REGION              1..7
                    note = synthetic construct
source              1..7
                    mol_type = protein
                    organism = synthetic construct
SEQUENCE: 43
FFRRFRR                                                                        7

SEQ ID NO: 44       moltype = AA   length = 7
FEATURE             Location/Qualifiers
REGION              1..7
                    note = synthetic construct
source              1..7
                    mol_type = protein
                    organism = synthetic construct
SEQUENCE: 44
FFRRRRF                                                                        7

SEQ ID NO: 45       moltype = AA   length = 7
FEATURE             Location/Qualifiers
REGION              1..7
                    note = synthetic construct
source              1..7
                    mol_type = protein
                    organism = synthetic construct
SEQUENCE: 45
FRRFFRR                                                                        7

SEQ ID NO: 46       moltype = AA   length = 8
FEATURE             Location/Qualifiers
REGION              1..8
                    note = synthetic construct
source              1..8
                    mol_type = protein
                    organism = synthetic construct
SEQUENCE: 46
FFFRRRRR                                                                       8

SEQ ID NO: 47       moltype = AA   length = 9
FEATURE             Location/Qualifiers
REGION              1..9
                    note = synthetic construct
source              1..9
                    mol_type = protein
                    organism = synthetic construct
SEQUENCE: 47
FFFRRRRRR                                                                      9

SEQ ID NO: 48       moltype = AA   length = 6
FEATURE             Location/Qualifiers
```

```
REGION            1..6
                  note = synthetic construct
VARIANT           1..2
                  note = Xaa is any amino acid
source            1..6
                  mol_type = protein
                  organism = synthetic construct
SEQUENCE: 48
XXRRRR                                                                          6

SEQ ID NO: 49     moltype = AA   length = 8
FEATURE           Location/Qualifiers
REGION            1..8
                  note = synthetic construct
source            1..8
                  mol_type = protein
                  organism = synthetic construct
SEQUENCE: 49
WRWRWRWR                                                                        8

SEQ ID NO: 50     moltype = AA   length = 5
FEATURE           Location/Qualifiers
REGION            1..5
                  note = synthetic construct
MOD_RES           5
                  note = D-alanine
source            1..5
                  mol_type = protein
                  organism = synthetic construct
SEQUENCE: 50
GWIYA                                                                           5

SEQ ID NO: 51     moltype = AA   length = 5
FEATURE           Location/Qualifiers
REGION            1..5
                  note = synthetic construct
MOD_RES           1
                  note = D-alanine
source            1..5
                  mol_type = protein
                  organism = synthetic construct
SEQUENCE: 51
AGWIY                                                                           5

SEQ ID NO: 52     moltype = AA   length = 4
FEATURE           Location/Qualifiers
REGION            1..4
                  note = synthetic construct
source            1..4
                  mol_type = protein
                  organism = synthetic construct
SEQUENCE: 52
YIWG                                                                            4

SEQ ID NO: 53     moltype = AA   length = 5
FEATURE           Location/Qualifiers
REGION            1..5
                  note = synthetic construct
source            1..5
                  mol_type = protein
                  organism = synthetic construct
SEQUENCE: 53
AYIWG                                                                           5

SEQ ID NO: 54     moltype = AA   length = 5
FEATURE           Location/Qualifiers
REGION            1..5
                  note = synthetic construct
MOD_RES           1
                  note = D-alanine
source            1..5
                  mol_type = protein
                  organism = synthetic construct
SEQUENCE: 54
AYIWG                                                                           5

SEQ ID NO: 55     moltype = AA   length = 5
FEATURE           Location/Qualifiers
REGION            1..5
```

```
                          note = synthetic construct
source                    1..5
                          mol_type = protein
                          organism = synthetic construct
SEQUENCE: 55
YIWGA                                                                     5

SEQ ID NO: 56             moltype = AA  length = 5
FEATURE                   Location/Qualifiers
REGION                    1..5
                          note = synthetic construct
MOD_RES                   5
                          note = D-alanine
source                    1..5
                          mol_type = protein
                          organism = synthetic construct
SEQUENCE: 56
YIWGA                                                                     5

SEQ ID NO: 57             moltype = AA  length = 5
FEATURE                   Location/Qualifiers
REGION                    1..5
                          note = synthetic construct
source                    1..5
                          mol_type = protein
                          organism = synthetic construct
SEQUENCE: 57
AYIWA                                                                     5

SEQ ID NO: 58             moltype = AA  length = 5
FEATURE                   Location/Qualifiers
REGION                    1..5
                          note = synthetic construct
source                    1..5
                          mol_type = protein
                          organism = synthetic construct
SEQUENCE: 58
AYIAG                                                                     5

SEQ ID NO: 59             moltype = AA  length = 5
FEATURE                   Location/Qualifiers
REGION                    1..5
                          note = synthetic construct
source                    1..5
                          mol_type = protein
                          organism = synthetic construct
SEQUENCE: 59
AYAWG                                                                     5

SEQ ID NO: 60             moltype = AA  length = 5
FEATURE                   Location/Qualifiers
REGION                    1..5
                          note = synthetic construct
source                    1..5
                          mol_type = protein
                          organism = synthetic construct
SEQUENCE: 60
AAIWG                                                                     5

SEQ ID NO: 61             moltype = AA  length = 5
FEATURE                   Location/Qualifiers
REGION                    1..5
                          note = synthetic construct
source                    1..5
                          mol_type = protein
                          organism = synthetic construct
SEQUENCE: 61
AYIWG                                                                     5

SEQ ID NO: 62             moltype = AA  length = 5
FEATURE                   Location/Qualifiers
REGION                    1..5
                          note = synthetic construct
source                    1..5
                          mol_type = protein
                          organism = synthetic construct
SEQUENCE: 62
AAIAG                                                                     5
```

-continued

| | | |
|---|---|---|
| SEQ ID NO: 63 | moltype = AA  length = 5 | |
| FEATURE | Location/Qualifiers | |
| REGION | 1..5 | |
| | note = synthetic construct | |
| source | 1..5 | |
| | mol_type = protein | |
| | organism = synthetic construct | |
| SEQUENCE: 63 | | |
| AAAAG | | 5 |
| | | |
| SEQ ID NO: 64 | moltype = AA  length = 10 | |
| FEATURE | Location/Qualifiers | |
| REGION | 1..10 | |
| | note = synthetic construct | |
| VARIANT | 1..10 | |
| | note = Amino acid may be glycine, D-glycine, tryptophan, D-tryptophan, isoleucine, D-isoleucine, tyrosine, D-tyrosine, alanine or D-alanine | |
| MOD_RES | 1..10 | |
| | note = Amino acid may be D-glycine, D-tryptophan, D-isoleucine, D-tyrosine or D-alanine | |
| VARIANT | 4..10 | |
| | note = Individual residues may be present or absent | |
| source | 1..10 | |
| | mol_type = protein | |
| | organism = synthetic construct | |
| SEQUENCE: 64 | | |
| GGGGGGGGGG | | 10 |
| | | |
| SEQ ID NO: 65 | moltype = AA  length = 7 | |
| FEATURE | Location/Qualifiers | |
| REGION | 1..7 | |
| | note = synthetic construct | |
| SITE | 1..7 | |
| | note = cyclic peptide | |
| MOD_RES | 2 | |
| | note = Xaa is napthylalanine | |
| source | 1..7 | |
| | mol_type = protein | |
| | organism = synthetic construct | |
| SEQUENCE: 65 | | |
| FXRRRRQ | | 7 |
| | | |
| SEQ ID NO: 66 | moltype = AA  length = 5 | |
| FEATURE | Location/Qualifiers | |
| REGION | 1..5 | |
| | note = Synthetic Construct | |
| MOD_RES | 2 | |
| | note = L-2-naphthylalanine | |
| source | 1..5 | |
| | mol_type = protein | |
| | organism = synthetic construct | |
| SEQUENCE: 66 | | |
| FXRRR | | 5 |
| | | |
| SEQ ID NO: 67 | moltype = AA  length = 6 | |
| FEATURE | Location/Qualifiers | |
| REGION | 1..6 | |
| | note = Synthetic Construct | |
| MOD_RES | 2 | |
| | note = L-2-naphthylalanine | |
| source | 1..6 | |
| | mol_type = protein | |
| | organism = synthetic construct | |
| SEQUENCE: 67 | | |
| FXRRRC | | 6 |
| | | |
| SEQ ID NO: 68 | moltype = AA  length = 6 | |
| FEATURE | Location/Qualifiers | |
| REGION | 1..6 | |
| | note = Synthetic Construct | |
| MOD_RES | 2 | |
| | note = L-2-naphthylalanine | |
| source | 1..6 | |
| | mol_type = protein | |
| | organism = synthetic construct | |
| SEQUENCE: 68 | | |
| FXRRRU | | 6 |

```
SEQ ID NO: 69           moltype = AA   length = 5
FEATURE                 Location/Qualifiers
REGION                  1..5
                        note = Synthetic Construct
MOD_RES                 4
                        note = L-2-naphthylalanine
source                  1..5
                        mol_type = protein
                        organism = synthetic construct
SEQUENCE: 69
RRRXF                                                                    5

SEQ ID NO: 70           moltype = AA   length = 6
FEATURE                 Location/Qualifiers
REGION                  1..6
                        note = Synthetic Construct
MOD_RES                 5
                        note = L-2-naphthylalanine
source                  1..6
                        mol_type = protein
                        organism = synthetic construct
SEQUENCE: 70
RRRRXF                                                                   6

SEQ ID NO: 71           moltype = AA   length = 6
FEATURE                 Location/Qualifiers
REGION                  1..6
                        note = Synthetic Construct
MOD_RES                 2
                        note = L-2-naphthylalanine
source                  1..6
                        mol_type = protein
                        organism = synthetic construct
SEQUENCE: 71
FXRRRR                                                                   6

SEQ ID NO: 72           moltype = AA   length = 6
FEATURE                 Location/Qualifiers
REGION                  1..6
                        note = Synthetic Construct
MOD_RES                 2
                        note = D-2-naphthylalanine
MOD_RES                 3
                        note = D-arginine
MOD_RES                 5
                        note = D-arginine
source                  1..6
                        mol_type = protein
                        organism = synthetic construct
SEQUENCE: 72
FXRRRR                                                                   6

SEQ ID NO: 73           moltype = AA   length = 6
FEATURE                 Location/Qualifiers
REGION                  1..6
                        note = Synthetic Construct
MOD_RES                 1
                        note = D-phenylalanine
MOD_RES                 2
                        note = L-2-naphthylalanine
MOD_RES                 4
                        note = D-arginine
MOD_RES                 6
                        note = D-arginine
source                  1..6
                        mol_type = protein
                        organism = synthetic construct
SEQUENCE: 73
FXRRRR                                                                   6

SEQ ID NO: 74           moltype = AA   length = 6
FEATURE                 Location/Qualifiers
REGION                  1..6
                        note = Synthetic Construct
MOD_RES                 5
                        note = L-2-naphthylalanine
source                  1..6
                        mol_type = protein
                        organism = synthetic construct
```

```
SEQUENCE: 74
RRFRXR                                                                        6

SEQ ID NO: 75           moltype = AA  length = 6
FEATURE                 Location/Qualifiers
REGION                  1..6
                        note = Synthetic Construct
MOD_RES                 6
                        note = L-2-naphthylalanine
source                  1..6
                        mol_type = protein
                        organism = synthetic construct
SEQUENCE: 75
FRRRRX                                                                        6

SEQ ID NO: 76           moltype = AA  length = 6
FEATURE                 Location/Qualifiers
REGION                  1..6
                        note = Synthetic Construct
MOD_RES                 1
                        note = D-arginine
MOD_RES                 5
                        note = L-2-naphthylalanine
source                  1..6
                        mol_type = protein
                        organism = synthetic construct
SEQUENCE: 76
RRFRXR                                                                        6

SEQ ID NO: 77           moltype = AA  length = 6
FEATURE                 Location/Qualifiers
REGION                  1..6
                        note = Synthetic Construct
MOD_RES                 3
                        note = L-2-naphthylalanine
source                  1..6
                        mol_type = protein
                        organism = synthetic construct
SEQUENCE: 77
RRXFRR                                                                        6

SEQ ID NO: 78           moltype = AA  length = 7
FEATURE                 Location/Qualifiers
REGION                  1..7
                        note = Synthetic Construct
MOD_RES                 2
                        note = D-phenylalanine
MOD_RES                 3
                        note = L-2-naphthylalanine
MOD_RES                 5
                        note = D-arginine
MOD_RES                 7
                        note = D-arginine
source                  1..7
                        mol_type = protein
                        organism = synthetic construct
SEQUENCE: 78
FFXRRRR                                                                       7

SEQ ID NO: 79           moltype = AA  length = 7
FEATURE                 Location/Qualifiers
REGION                  1..7
                        note = Synthetic Construct
MOD_RES                 3
                        note = L-2-naphthylalanine
source                  1..7
                        mol_type = protein
                        organism = synthetic construct
SEQUENCE: 79
FFXRRRR                                                                       7

SEQ ID NO: 80           moltype = AA  length = 7
FEATURE                 Location/Qualifiers
REGION                  1..7
                        note = Synthetic Construct
MOD_RES                 6
                        note = L-2-naphthylalanine
source                  1..7
                        mol_type = protein
```

```
                        organism = synthetic construct
SEQUENCE: 80
RFRFRXR                                                                 7

SEQ ID NO: 81           moltype = AA   length = 8
FEATURE                 Location/Qualifiers
REGION                  1..8
                        note = Synthetic Construct
MOD_RES                 2
                        note = L-2-naphthylalanine
source                  1..8
                        mol_type = protein
                        organism = synthetic construct
SEQUENCE: 81
FXRRRRQK                                                                8

SEQ ID NO: 82           moltype = AA   length = 8
FEATURE                 Location/Qualifiers
REGION                  1..8
                        note = Synthetic Construct
MOD_RES                 2
                        note = L-2-naphthylalanine
source                  1..8
                        mol_type = protein
                        organism = synthetic construct
SEQUENCE: 82
FXRRRRQC                                                                8

SEQ ID NO: 83           moltype = AA   length = 7
FEATURE                 Location/Qualifiers
REGION                  1..7
                        note = Synthetic Construct
MOD_RES                 1
                        note = D-phenylalanine
MOD_RES                 2
                        note = L-2-naphthylalanine
MOD_RES                 4
                        note = D-arginine
MOD_RES                 6
                        note = D-arginine
source                  1..7
                        mol_type = protein
                        organism = synthetic construct
SEQUENCE: 83
FXRRRRR                                                                 7

SEQ ID NO: 84           moltype = AA   length = 7
FEATURE                 Location/Qualifiers
REGION                  1..7
                        note = Synthetic Construct
MOD_RES                 2
                        note = L-2-naphthylalanine
source                  1..7
                        mol_type = protein
                        organism = synthetic construct
SEQUENCE: 84
FXRRRRR                                                                 7

SEQ ID NO: 85           moltype = AA   length = 9
FEATURE                 Location/Qualifiers
REGION                  1..9
                        note = Synthetic Construct
MOD_RES                 5
                        note = L-2-naphthylalanine
MOD_RES                 8
                        note = Nle
source                  1..9
                        mol_type = protein
                        organism = synthetic construct
SEQUENCE: 85
RRRRXFDXC                                                               9

SEQ ID NO: 86           moltype = AA   length = 5
FEATURE                 Location/Qualifiers
REGION                  1..5
                        note = Synthetic Construct
MOD_RES                 3
                        note = D-arginine
MOD_RES                 5
```

```
                        note = D-arginine
source                  1..5
                        mol_type = protein
                        organism = synthetic construct
SEQUENCE: 86
FFRRR                                                                      5

SEQ ID NO: 87           moltype = AA  length = 5
FEATURE                 Location/Qualifiers
REGION                  1..5
                        note = Synthetic Construct
MOD_RES                 4
                        note = D-arginine
source                  1..5
                        mol_type = protein
                        organism = synthetic construct
SEQUENCE: 87
FFRRR                                                                      5

SEQ ID NO: 88           moltype = AA  length = 5
FEATURE                 Location/Qualifiers
REGION                  1..5
                        note = Synthetic Construct
MOD_RES                 2
                        note = L-2-naphthylalanine
source                  1..5
                        mol_type = protein
                        organism = synthetic construct
SEQUENCE: 88
GXRRR                                                                      5

SEQ ID NO: 89           moltype = AA  length = 6
FEATURE                 Location/Qualifiers
REGION                  1..6
                        note = Synthetic Construct
MOD_RES                 2
                        note = L-2-naphthylalanine
source                  1..6
                        mol_type = protein
                        organism = synthetic construct
SEQUENCE: 89
GXRRRR                                                                     6

SEQ ID NO: 90           moltype = AA  length = 6
FEATURE                 Location/Qualifiers
REGION                  1..6
                        note = Synthetic Construct
MOD_RES                 2
                        note = L-2-naphthylalanine
MOD_RES                 4
                        note = D-arginine
MOD_RES                 6
                        note = D-arginine
source                  1..6
                        mol_type = protein
                        organism = synthetic construct
SEQUENCE: 90
FXRRRR                                                                     6

SEQ ID NO: 91           moltype = AA  length = 6
FEATURE                 Location/Qualifiers
REGION                  1..6
                        note = Synthetic Construct
MOD_RES                 2
                        note = D-phenylalanine
MOD_RES                 5
                        note = D-arginine
source                  1..6
                        mol_type = protein
                        organism = synthetic construct
SEQUENCE: 91
FFFRRR                                                                     6

SEQ ID NO: 92           moltype = AA  length = 6
FEATURE                 Location/Qualifiers
REGION                  1..6
                        note = Synthetic Construct
MOD_RES                 1
                        note = D-phenylalanine
```

```
MOD_RES          3
                 note = D-phenylalanine
MOD_RES          4
                 note = D-arginine
MOD_RES          6
                 note = D-arginine
source           1..6
                 mol_type = protein
                 organism = synthetic construct
SEQUENCE: 92
FFFRRR                                                                           6

SEQ ID NO: 93    moltype = AA  length = 6
FEATURE          Location/Qualifiers
REGION           1..6
                 note = Synthetic Construct
MOD_RES          1
                 note = D-phenylalanine
MOD_RES          3
                 note = D-phenylalanine
MOD_RES          5
                 note = D-arginine
source           1..6
                 mol_type = protein
                 organism = synthetic construct
SEQUENCE: 93
FFFRRR                                                                           6

SEQ ID NO: 94    moltype = AA  length = 6
FEATURE          Location/Qualifiers
REGION           1..6
                 note = Synthetic Construct
MOD_RES          2
                 note = D-phenylalanine
MOD_RES          4
                 note = D-arginine
MOD_RES          6
                 note = D-arginine
source           1..6
                 mol_type = protein
                 organism = synthetic construct
SEQUENCE: 94
FFFRRR                                                                           6

SEQ ID NO: 95    moltype = AA  length = 6
FEATURE          Location/Qualifiers
REGION           1..6
                 note = Synthetic Construct
MOD_RES          1
                 note = D-phenylalanine
MOD_RES          3
                 note = D-2-naphthylalanine
MOD_RES          4
                 note = D-arginine
MOD_RES          6
                 note = D-arginine
source           1..6
                 mol_type = protein
                 organism = synthetic construct
SEQUENCE: 95
FFXRRR                                                                           6

SEQ ID NO: 96    moltype = AA  length = 6
FEATURE          Location/Qualifiers
REGION           1..6
                 note = Synthetic Construct
MOD_RES          1
                 note = D-phenylalanine
MOD_RES          2
                 note = L-2-naphthylalanine
MOD_RES          3
                 note = D-phenylalanine
MOD_RES          4
                 note = D-arginine
MOD_RES          6
                 note = D-arginine
source           1..6
                 mol_type = protein
                 organism = synthetic construct
```

```
SEQUENCE: 96
FXFRRR                                                                     6

SEQ ID NO: 97           moltype = AA   length = 6
FEATURE                 Location/Qualifiers
REGION                  1..6
                        note = Synthetic Construct
MOD_RES                 1
                        note = D-2-naphthylalanine
MOD_RES                 3
                        note = D-phenylalanine
MOD_RES                 4
                        note = D-arginine
MOD_RES                 6
                        note = D-arginine
source                  1..6
                        mol_type = protein
                        organism = synthetic construct
SEQUENCE: 97
XFFRRR                                                                     6

SEQ ID NO: 98           moltype = AA   length = 5
FEATURE                 Location/Qualifiers
REGION                  1..5
                        note = Synthetic Construct
MOD_RES                 2
                        note = L-2-naphthylalanine
MOD_RES                 3
                        note = D-arginine
MOD_RES                 5
                        note = D-arginine
source                  1..5
                        mol_type = protein
                        organism = synthetic construct
SEQUENCE: 98
FXRRR                                                                      5

SEQ ID NO: 99           moltype = AA   length = 5
FEATURE                 Location/Qualifiers
REGION                  1..5
                        note = Synthetic Construct
MOD_RES                 1
                        note = D-phenylalanine
MOD_RES                 2
                        note = L-2-naphthylalanine
MOD_RES                 3
                        note = D-arginine
MOD_RES                 5
                        note = D-arginine
source                  1..5
                        mol_type = protein
                        organism = synthetic construct
SEQUENCE: 99
FXRRR                                                                      5

SEQ ID NO: 100          moltype = AA   length = 8
FEATURE                 Location/Qualifiers
REGION                  1..8
                        note = Synthetic Construct
MOD_RES                 1
                        note = Amino acid is acetylated
MOD_RES                 2
                        note = D-phenylalanine
MOD_RES                 5
                        note = D-arginine
MOD_RES                 7
                        note = D-arginine
source                  1..8
                        mol_type = protein
                        organism = synthetic construct
SEQUENCE: 100
KFFRRRRD                                                                   8

SEQ ID NO: 101          moltype = AA   length = 8
FEATURE                 Location/Qualifiers
REGION                  1..8
                        note = Synthetic Construct
MOD_RES                 1
                        note = Amino acid is acetylated
```

```
MOD_RES              1
                     note = L-2,3-diaminopropionic acid
MOD_RES              2
                     note = D-phenylalanine
MOD_RES              5
                     note = D-arginine
MOD_RES              7
                     note = D-arginine
source               1..8
                     mol_type = protein
                     organism = synthetic construct
SEQUENCE: 101
XFFRRRRD                                                                         8

SEQ ID NO: 102       moltype = AA  length = 8
FEATURE              Location/Qualifiers
REGION               1..8
                     note = Synthetic Construct
DISULFID             1..8
                     note = disulfide bond
source               1..8
                     mol_type = protein
                     organism = synthetic construct
SEQUENCE: 102
CWWRRRRC                                                                         8

SEQ ID NO: 103       moltype = AA  length = 9
FEATURE              Location/Qualifiers
REGION               1..9
                     note = Synthetic Construct
DISULFID             1..9
                     note = disulfide bond
source               1..9
                     mol_type = protein
                     organism = synthetic construct
SEQUENCE: 103
CWWWRRRRC                                                                        9

SEQ ID NO: 104       moltype = AA  length = 8
FEATURE              Location/Qualifiers
REGION               1..8
                     note = Synthetic Construct
DISULFID             1..8
                     note = disulfide bond
source               1..8
                     mol_type = protein
                     organism = synthetic construct
SEQUENCE: 104
CFWRRRRC                                                                         8

SEQ ID NO: 105       moltype = AA  length = 8
FEATURE              Location/Qualifiers
REGION               1..8
                     note = Synthetic Construct
DISULFID             1..8
                     note = disulfide bond
source               1..8
                     mol_type = protein
                     organism = synthetic construct
SEQUENCE: 105
CWWWRRRC                                                                         8

SEQ ID NO: 106       moltype = AA  length = 7
FEATURE              Location/Qualifiers
REGION               1..7
                     note = Synthetic Construct
MOD_RES              1
                     note = L-homoproline
MOD_RES              2
                     note = L-2-naphthylalanine
MOD_RES              5..6
                     note = D-arginine
MOD_RES              7
                     note = D-glutamate
source               1..7
                     mol_type = protein
                     organism = synthetic construct
SEQUENCE: 106
XXRERRE                                                                          7
```

```
SEQ ID NO: 107        moltype = AA  length = 7
FEATURE               Location/Qualifiers
REGION                1..7
                      note = Synthetic Construct
MOD_RES               1
                      note = L-homoproline
MOD_RES               2
                      note = L-2-naphthylalanine
MOD_RES               5..6
                      note = D-arginine
MOD_RES               7
                      note = D-glutamate
source                1..7
                      mol_type = protein
                      organism = synthetic construct
SEQUENCE: 107
XXRRRRE                                                                    7

SEQ ID NO: 108        moltype = AA  length = 7
FEATURE               Location/Qualifiers
REGION                1..7
                      note = Synthetic Construct
MOD_RES               1
                      note = L-homoproline
MOD_RES               2..3
                      note = L-2-naphthylalanine
MOD_RES               5..6
                      note = D-arginine
MOD_RES               7
                      note = D-glutamate
source                1..7
                      mol_type = protein
                      organism = synthetic construct
SEQUENCE: 108
XXXRRRE                                                                    7

SEQ ID NO: 109        moltype = AA  length = 7
FEATURE               Location/Qualifiers
REGION                1..7
                      note = Synthetic Construct
MOD_RES               1
                      note = L-homoproline
MOD_RES               2..3
                      note = L-2-naphthylalanine
MOD_RES               5..6
                      note = D-arginine
source                1..7
                      mol_type = protein
                      organism = synthetic construct
SEQUENCE: 109
XXXRRRE                                                                    7

SEQ ID NO: 110        moltype = AA  length = 7
FEATURE               Location/Qualifiers
REGION                1..7
                      note = Synthetic Construct
MOD_RES               1
                      note = L-homoproline
MOD_RES               2
                      note = L-2-naphthylalanine
MOD_RES               5..6
                      note = D-arginine
MOD_RES               7
                      note = D-glutamate
source                1..7
                      mol_type = protein
                      organism = synthetic construct
SEQUENCE: 110
XXFRRRE                                                                    7

SEQ ID NO: 111        moltype = AA  length = 7
FEATURE               Location/Qualifiers
REGION                1..7
                      note = Synthetic Construct
MOD_RES               1
                      note = L-homoproline
MOD_RES               2
                      note = L-2-naphthylalanine
```

```
MOD_RES                 5..6
                        note = D-arginine
source                  1..7
                        mol_type = protein
                        organism = synthetic construct
SEQUENCE: 111
XXFRRRE                                                                            7

SEQ ID NO: 112          moltype = AA  length = 7
FEATURE                 Location/Qualifiers
REGION                  1..7
                        note = Synthetic Construct
MOD_RES                 1
                        note = L-homoproline
MOD_RES                 2
                        note = L-2-naphthylalanine
MOD_RES                 3
                        note = D-phenylalanine
MOD_RES                 5..6
                        note = D-arginine
MOD_RES                 7
                        note = D-glutamate
source                  1..7
                        mol_type = protein
                        organism = synthetic construct
SEQUENCE: 112
XXFRRRE                                                                            7

SEQ ID NO: 113          moltype = AA  length = 7
FEATURE                 Location/Qualifiers
REGION                  1..7
                        note = Synthetic Construct
MOD_RES                 1
                        note = L-homoproline
MOD_RES                 2
                        note = L-2-naphthylalanine
MOD_RES                 3
                        note = D-phenylalanine
MOD_RES                 5..6
                        note = D-arginine
source                  1..7
                        mol_type = protein
                        organism = synthetic construct
SEQUENCE: 113
XXFRRRE                                                                            7

SEQ ID NO: 114          moltype = AA  length = 7
FEATURE                 Location/Qualifiers
REGION                  1..7
                        note = Synthetic Construct
MOD_RES                 1
                        note = L-homoproline
MOD_RES                 2
                        note = L-2-naphthylalanine
MOD_RES                 3
                        note = D-2-naphthylalanine
MOD_RES                 5..6
                        note = D-arginine
source                  1..7
                        mol_type = protein
                        organism = synthetic construct
SEQUENCE: 114
XXXRRRE                                                                            7

SEQ ID NO: 115          moltype = AA  length = 7
FEATURE                 Location/Qualifiers
REGION                  1..7
                        note = Synthetic Construct
MOD_RES                 1
                        note = L-homoproline
MOD_RES                 2
                        note = L-2-naphthylalanine
MOD_RES                 3
                        note = D-2-naphthylalanine
MOD_RES                 5..6
                        note = D-arginine
MOD_RES                 7
                        note = D-glutamate
source                  1..7
```

```
                           mol_type = protein
                           organism = synthetic construct
SEQUENCE: 115
XXXRRRE                                                                    7

SEQ ID NO: 116             moltype = AA  length = 8
FEATURE                    Location/Qualifiers
REGION                     1..8
                           note = synthetic construct
MOD_RES                    1
                           note = Arg is modified with pimelic acid
SITE                       1..4
                           note = Cyclization between Arg is modified with pimelic
                            acid and Arg is modified with lysine peptoid residue
MOD_RES                    4
                           note = Arg is modified with lysine peptoid residue
source                     1..8
                           mol_type = protein
                           organism = synthetic construct
SEQUENCE: 116
RQRRGRRR                                                                   8

SEQ ID NO: 117             moltype = AA  length = 19
FEATURE                    Location/Qualifiers
REGION                     1..19
                           note = synthetic construct
DISULFID                   2..19
                           note = Cys residues joined by disulfide bond
source                     1..19
                           mol_type = protein
                           organism = synthetic construct
SEQUENCE: 117
KCFQWQRNMR KVRGPPVSC                                                      19

SEQ ID NO: 118             moltype = AA  length = 11
FEATURE                    Location/Qualifiers
REGION                     1..11
                           note = synthetic construct
SITE                       1..11
                           note = Cyclization between Lys and Glu
MOD_RES                    2
                           note = D-arginine
MOD_RES                    4
                           note = D-arginine
MOD_RES                    6
                           note = D-arginine
MOD_RES                    8
                           note = D-lysine
MOD_RES                    10
                           note = D-arginine
source                     1..11
                           mol_type = protein
                           organism = synthetic construct
SEQUENCE: 118
KRRRGRKKRR E                                                              11

SEQ ID NO: 119             moltype = AA  length = 12
FEATURE                    Location/Qualifiers
REGION                     1..12
                           note = synthetic construct
SITE                       1..12
                           note = Cyclization between Lys and Glu
MOD_RES                    2
                           note = D-arginine
MOD_RES                    4
                           note = D-arginine
MOD_RES                    6
                           note = D-arginine
MOD_RES                    8
                           note = D-arginine
MOD_RES                    10
                           note = D-arginine
source                     1..12
                           mol_type = protein
                           organism = synthetic construct
SEQUENCE: 119
KRRRRRRRRR RE                                                             12

SEQ ID NO: 120             moltype = AA  length = 14
```

```
FEATURE                 Location/Qualifiers
REGION                  1..14
                        note = synthetic construct
MOD_RES                 13
                        note = D-proline
source                  1..14
                        mol_type = protein
                        organism = synthetic construct
SEQUENCE: 120
RVRTRGKRRI RRPP                                                              14

SEQ ID NO: 121          moltype = AA  length = 14
FEATURE                 Location/Qualifiers
REGION                  1..14
                        note = synthetic construct
MOD_RES                 13
                        note = D-proline
source                  1..14
                        mol_type = protein
                        organism = synthetic construct
SEQUENCE: 121
RTRTRGKRRI RVPP                                                              14

SEQ ID NO: 122          moltype = AA  length = 34
FEATURE                 Location/Qualifiers
REGION                  1..34
                        note = synthetic construct
DISULFID                4..21
                        note = Cys residues joined by disulfide bond
DISULFID                11..23
                        note = Cys residues joined by disulfide bond
DISULFID                17..29
                        note = Cys residues joined by disulfide bond
source                  1..34
                        mol_type = protein
                        organism = synthetic construct
SEQUENCE: 122
GGVCPKILKK CRRDSDCPGA CICRGNGYCG SGSD                                        34

SEQ ID NO: 123          moltype = AA  length = 10
FEATURE                 Location/Qualifiers
REGION                  1..10
                        note = synthetic construct
SITE                    1..10
                        note = Macrocyclization by multicomponent reaction with
                         aziridine aldehyde and isocyanide
MOD_RES                 2
                        note = L-3-cyclohexyl-alanine
MOD_RES                 3
                        note = D-arginine
MOD_RES                 4
                        note = L-cyclohexylalanine
MOD_RES                 5
                        note = D-arginine
MOD_RES                 6
                        note = L-cyclohexylalanine
MOD_RES                 7
                        note = D-arginine
MOD_RES                 8
                        note = L-cyclohexylalanine
MOD_RES                 9
                        note = D-arginine
source                  1..10
                        mol_type = protein
                        organism = synthetic construct
SEQUENCE: 123
PXRXRXRXRG                                                                   10

SEQ ID NO: 124          moltype = AA  length = 13
FEATURE                 Location/Qualifiers
REGION                  1..13
                        note = synthetic construct
MOD_RES                 1
                        note = Ser is modified with trimesic acid
SITE                    1..13
                        note = N-terminal amine and side chains of two
                         L-2,3-diaminopropionic acid residues bicyclized with
                         trimesic acid
MOD_RES                 2
```

```
                        note = D-valine
MOD_RES                 4
                        note = L-4-(phosphonodifluoromethyl)phenylalanine
MOD_RES                 6
                        note = L-2,3-diaminopropionic acid
MOD_RES                 8
                        note = L-naphthylalanine
MOD_RES                 13
                        note = L-2,3-diaminopropionic acid
source                  1..13
                        mol_type = protein
                        organism = synthetic construct
SEQUENCE: 124
SVPXHXFXRR RRX                                                                 13

SEQ ID NO: 125          moltype = AA  length = 17
FEATURE                 Location/Qualifiers
REGION                  1..17
                        note = synthetic construct
MOD_RES                 1
                        note = D-alanine is modified with trimesic acid
MOD_RES                 1
                        note = D-amino acid
SITE                    1..17
                        note = N-terminal amine and side chains of two
                         L-2,3-diaminopropionic acid residues bicyclized with
                         trimesic acid
MOD_RES                 2
                        note = sarcosine
MOD_RES                 4
                        note = D-phosphothreonine
MOD_RES                 5
                        note = L-homoproline
MOD_RES                 6
                        note = L-naphthylalanine
MOD_RES                 9
                        note = D-alanine
MOD_RES                 10
                        note = L-2,3-diaminopropionic acid
MOD_RES                 12
                        note = L-naphthylalanine
MOD_RES                 17
                        note = L-2,3-diaminopropionic acid
source                  1..17
                        mol_type = protein
                        organism = synthetic construct
SEQUENCE: 125
AXDXXXRAXX FXRRRRX                                                             17

SEQ ID NO: 126          moltype = AA  length = 16
FEATURE                 Location/Qualifiers
REGION                  1..16
                        note = synthetic construct
SITE                    1..15
                        note = Three Cys side chains bicyclized with
                         tris(bromomethyl)benzene
source                  1..16
                        mol_type = protein
                        organism = synthetic construct
SEQUENCE: 126
CRRSRRGCGR RSRRCG                                                              16

SEQ ID NO: 127          moltype = AA  length = 16
FEATURE                 Location/Qualifiers
REGION                  1..16
                        note = synthetic construct
SITE                    1..15
                        note = Three Cys side chains bicyclized with
                         tris(bromomethyl)benzene
source                  1..16
                        mol_type = protein
                        organism = synthetic construct
SEQUENCE: 127
CRRSRRGCGR RSRRCG                                                              16

SEQ ID NO: 128          moltype = AA  length = 5
FEATURE                 Location/Qualifiers
REGION                  1..5
                        note = synthetic construct
```

```
SITE                     1..2
                         note = linked by dodecanoyl moiety
source                   1..5
                         mol_type = protein
                         organism = synthetic construct
SEQUENCE: 128
KRRRR                                                                   5

SEQ ID NO: 129           moltype = AA   length = 16
FEATURE                  Location/Qualifiers
REGION                   1..16
                         note = synthetic construct
source                   1..16
                         mol_type = protein
                         organism = synthetic construct
SEQUENCE: 129
LKKLCKLLKK LCKLAG                                                      16

SEQ ID NO: 130           moltype = AA   length = 9
FEATURE                  Location/Qualifiers
REGION                   1..9
                         note = synthetic construct
SITE                     5..9
                         note = Cyclization between Lys and Glu
source                   1..9
                         mol_type = protein
                         organism = synthetic construct
SEQUENCE: 130
RRRRKRRRE                                                               9

SEQ ID NO: 131           moltype = AA   length = 9
FEATURE                  Location/Qualifiers
REGION                   1..9
                         note = synthetic construct
SITE                     4..9
                         note = Cyclization between Lys and Glu
source                   1..9
                         mol_type = protein
                         organism = synthetic construct
SEQUENCE: 131
RRRKRRRRE                                                               9

SEQ ID NO: 132           moltype = AA   length = 9
FEATURE                  Location/Qualifiers
REGION                   1..9
                         note = synthetic construct
SITE                     3..9
                         note = Cyclization between Lys and Glu
source                   1..9
                         mol_type = protein
                         organism = synthetic construct
SEQUENCE: 132
RRKRRRRRE                                                               9

SEQ ID NO: 133           moltype = AA   length = 9
FEATURE                  Location/Qualifiers
REGION                   1..9
                         note = synthetic construct
SITE                     2..9
                         note = Cyclization between Lys and Glu
source                   1..9
                         mol_type = protein
                         organism = synthetic construct
SEQUENCE: 133
RKRRRRRRE                                                               9

SEQ ID NO: 134           moltype = AA   length = 8
FEATURE                  Location/Qualifiers
REGION                   1..8
                         note = synthetic construct
source                   1..8
                         mol_type = protein
                         organism = synthetic construct
SEQUENCE: 134
CRCRCRCR                                                                8

SEQ ID NO: 135           moltype = AA   length = 12
FEATURE                  Location/Qualifiers
REGION                   1..12
```

|   |   |   |
|---|---|---|
| MOD_RES | 1 | |
| | note = L-propargylglycine | |
| SITE | 1..12 | |
| | note = Cyclization by the click reaction between L-propargylglycine and L-6-Azido-2-amino-hexanoic | |
| MOD_RES | 12 | |
| | note = L-6-Azido-2-amino-hexanoic | |
| source | 1..12 | |
| | mol_type = protein | |
| | organism = synthetic construct | |
| SEQUENCE: 135 | | |
| XLRKRLRKFR NX | | 12 |
| | | |
| SEQ ID NO: 136 | moltype = AA  length = 9 | |
| FEATURE | Location/Qualifiers | |
| REGION | 1..9 | |
| | note = synthetic construct | |
| MOD_RES | 2..4 | |
| | note = L-2,3-diaminopropionic acid | |
| MOD_RES | 5 | |
| | note = D-amino acid | |
| MOD_RES | 7..8 | |
| | note = L-2,3-diaminopropionic acid | |
| source | 1..9 | |
| | mol_type = protein | |
| | organism = synthetic construct | |
| SEQUENCE: 136 | | |
| TXXXFLXXT | | 9 |
| | | |
| SEQ ID NO: 137 | moltype = AA  length = 9 | |
| FEATURE | Location/Qualifiers | |
| REGION | 1..9 | |
| | note = synthetic construct | |
| MOD_RES | 2 | |
| | note = L-2-amino-3-guanidinylpropionic acid | |
| MOD_RES | 3 | |
| | note = L-2,3-diaminopropionic acid | |
| MOD_RES | 4 | |
| | note = L-2-amino-3-guanidinylpropionic acid | |
| MOD_RES | 5 | |
| | note = D-phenylalanine | |
| MOD_RES | 7..8 | |
| | note = L-2-amino-3-guanidinylpropionic acid | |
| source | 1..9 | |
| | mol_type = protein | |
| | organism = synthetic construct | |
| SEQUENCE: 137 | | |
| TXXXFLXXT | | 9 |
| | | |
| SEQ ID NO: 138 | moltype = AA  length = 29 | |
| FEATURE | Location/Qualifiers | |
| REGION | 1..29 | |
| | note = synthetic construct | |
| source | 1..29 | |
| | mol_type = protein | |
| | organism = synthetic construct | |
| SEQUENCE: 138 | | |
| RQIKIWFQNR RMKWKKGGTA LDWSWLQTE | | 29 |
| | | |
| SEQ ID NO: 139 | moltype = AA  length = 14 | |
| FEATURE | Location/Qualifiers | |
| REGION | 1..14 | |
| | note = synthetic construct | |
| MOD_RES | 1 | |
| | note = Glycine is modified with trimesic acid | |
| MOD_RES | 5 | |
| | note = L-2,3-diaminopropionic acid | |
| MOD_RES | 7 | |
| | note = L-2-naphthylalanine | |
| MOD_RES | 11 | |
| | note = L-2,3-diaminopropionic acid | |
| MOD_RES | 12..13 | |
| | note = bAla | |
| source | 1..14 | |
| | mol_type = protein | |
| | organism = synthetic construct | |
| SEQUENCE: 139 | | |
| GWIYXFXRRR XXXK | | 14 |

```
SEQ ID NO: 140          moltype = AA  length = 15
FEATURE                 Location/Qualifiers
REGION                  1..15
                        note = synthetic construct
MOD_RES                 1
                        note = Glycine is modified with trimesic acid
MOD_RES                 5
                        note = L-2,3-diaminopropionic acid
MOD_RES                 7
                        note = L-2-naphthylalanine
MOD_RES                 12
                        note = L-2,3-diaminopropionic acid
MOD_RES                 13..14
                        note = bAla
source                  1..15
                        mol_type = protein
                        organism = synthetic construct
SEQUENCE: 140
GWIYXFXRRR RXXXK                                                            15

SEQ ID NO: 141          moltype = AA  length = 14
FEATURE                 Location/Qualifiers
REGION                  1..14
                        note = synthetic construct
MOD_RES                 1
                        note = Glycine is modified with trimesic acid
MOD_RES                 5
                        note = L-2,3-diaminopropionic acid
MOD_RES                 7
                        note = L-2-naphthylalanine
MOD_RES                 11
                        note = L-2,3-diaminopropionic acid
MOD_RES                 13
                        note = bAla
source                  1..14
                        mol_type = protein
                        organism = synthetic construct
SEQUENCE: 141
GWIYXFXRRR XRXK                                                             14

SEQ ID NO: 142          moltype = AA  length = 14
FEATURE                 Location/Qualifiers
REGION                  1..14
                        note = synthetic construct
MOD_RES                 1
                        note = Glycine is modified with trimesic acid
MOD_RES                 5
                        note = L-2,3-diaminopropionic acid
MOD_RES                 7
                        note = L-2-naphthylalanine
MOD_RES                 11
                        note = L-2,3-diaminopropionic acid
MOD_RES                 12
                        note = D-arginine
MOD_RES                 13
                        note = bAla
source                  1..14
                        mol_type = protein
                        organism = synthetic construct
SEQUENCE: 142
GWIYXFXRRR XRXK                                                             14

SEQ ID NO: 143          moltype = AA  length = 14
FEATURE                 Location/Qualifiers
REGION                  1..14
                        note = synthetic construct
MOD_RES                 1
                        note = Glycine is modified with trimesic acid
MOD_RES                 5
                        note = L-2,3-diaminopropionic acid
MOD_RES                 7
                        note = L-2-naphthylalanine
MOD_RES                 9
                        note = D-arginine
MOD_RES                 11
                        note = L-2,3-diaminopropionic acid
MOD_RES                 12..13
                        note = bAla
```

```
source                   1..14
                         mol_type = protein
                         organism = synthetic construct
SEQUENCE: 143
GWIYXFXRRR XXXK                                                              14

SEQ ID NO: 144           moltype = AA  length = 15
FEATURE                  Location/Qualifiers
REGION                   1..15
                         note = synthetic construct
MOD_RES                  1
                         note = Glycine is modified with trimesic acid
MOD_RES                  6
                         note = L-2,3-diaminopropionic acid
MOD_RES                  8
                         note = L-2-naphthylalanine
MOD_RES                  10
                         note = D-arginine
MOD_RES                  12
                         note = L-2,3-diaminopropionic acid
MOD_RES                  13..14
                         note = bAla
source                   1..15
                         mol_type = protein
                         organism = synthetic construct
SEQUENCE: 144
GWIYAXFXRR RXXXK                                                             15

SEQ ID NO: 145           moltype = AA  length = 15
FEATURE                  Location/Qualifiers
REGION                   1..15
                         note = synthetic construct
MOD_RES                  1
                         note = Glycine is modified with trimesic acid
MOD_RES                  6
                         note = L-2,3-diaminopropionic acid
MOD_RES                  8
                         note = L-2-naphthylalanine
MOD_RES                  10
                         note = D-arginine
MOD_RES                  12
                         note = L-2,3-diaminopropionic acid
MOD_RES                  13..14
                         note = bAla
source                   1..15
                         mol_type = protein
                         organism = synthetic construct
SEQUENCE: 145
GWIYAXFXRR RXXXK                                                             15

SEQ ID NO: 146           moltype = AA  length = 15
FEATURE                  Location/Qualifiers
REGION                   1..15
                         note = synthetic construct
MOD_RES                  1
                         note = Alanine is modified with trimesic acid
MOD_RES                  6
                         note = L-2,3-diaminopropionic acid
MOD_RES                  8
                         note = L-2-naphthylalanine
MOD_RES                  10
                         note = D-arginine
MOD_RES                  12
                         note = L-2,3-diaminopropionic acid
MOD_RES                  13..14
                         note = bAla
source                   1..15
                         mol_type = protein
                         organism = synthetic construct
SEQUENCE: 146
AGWIYXFXRR RXXXK                                                             15

SEQ ID NO: 147           moltype = AA  length = 15
FEATURE                  Location/Qualifiers
REGION                   1..15
                         note = synthetic construct
MOD_RES                  1
                         note = Alanine is modified with trimesic acid
MOD_RES                  1
```

```
                        note = D-alanine
MOD_RES                 6
                        note = L-2,3-diaminopropionic acid
MOD_RES                 8
                        note = L-2-naphthylalanine
MOD_RES                 10
                        note = D-arginine
MOD_RES                 12
                        note = L-2,3-diaminopropionic acid
MOD_RES                 13..14
                        note = bAla
source                  1..15
                        mol_type = protein
                        organism = synthetic construct
SEQUENCE: 147
AGWIYXFXRR RXXXK                                                          15

SEQ ID NO: 148          moltype = AA  length = 15
FEATURE                 Location/Qualifiers
REGION                  1..15
                        note = synthetic construct
MOD_RES                 1
                        note = Alanine is modified with trimesic acid
MOD_RES                 6
                        note = L-2,3-diaminopropionic acid
MOD_RES                 8
                        note = L-2-naphthylalanine
MOD_RES                 10
                        note = D-arginine
MOD_RES                 12
                        note = L-2,3-diaminopropionic acid
MOD_RES                 13..14
                        note = bAla
source                  1..15
                        mol_type = protein
                        organism = synthetic construct
SEQUENCE: 148
AWIYAXFXRR RXXXK                                                          15

SEQ ID NO: 149          moltype = AA  length = 15
FEATURE                 Location/Qualifiers
REGION                  1..15
                        note = synthetic construct
MOD_RES                 1
                        note = Glycine is modified with trimesic acid
MOD_RES                 6
                        note = L-2,3-diaminopropionic acid
MOD_RES                 8
                        note = L-2-naphthylalanine
MOD_RES                 10
                        note = D-arginine
MOD_RES                 12
                        note = L-2,3-diaminopropionic acid
MOD_RES                 13..14
                        note = bAla
source                  1..15
                        mol_type = protein
                        organism = synthetic construct
SEQUENCE: 149
GAIYAXFXRR RXXXK                                                          15

SEQ ID NO: 150          moltype = AA  length = 15
FEATURE                 Location/Qualifiers
REGION                  1..15
                        note = synthetic construct
MOD_RES                 1
                        note = Glycine is modified with trimesic acid
MOD_RES                 6
                        note = L-2,3-diaminopropionic acid
MOD_RES                 8
                        note = L-2-naphthylalanine
MOD_RES                 10
                        note = D-arginine
MOD_RES                 12
                        note = L-2,3-diaminopropionic acid
MOD_RES                 13..14
                        note = bAla
source                  1..15
                        mol_type = protein
```

```
                        organism = synthetic construct
SEQUENCE: 150
GWAYAXFXRR RXXXK                                                              15

SEQ ID NO: 151          moltype = AA   length = 15
FEATURE                 Location/Qualifiers
REGION                  1..15
                        note = synthetic construct
MOD_RES                 1
                        note = Glycine is modified with trimesic acid
MOD_RES                 6
                        note = L-2,3-diaminopropionic acid
MOD_RES                 8
                        note = L-2-naphthylalanine
MOD_RES                 10
                        note = D-arginine
MOD_RES                 12
                        note = L-2,3-diaminopropionic acid
MOD_RES                 13..14
                        note = bAla
source                  1..15
                        mol_type = protein
                        organism = synthetic construct
SEQUENCE: 151
GWIAAXFXRR RXXXK                                                              15

SEQ ID NO: 152          moltype = AA   length = 15
FEATURE                 Location/Qualifiers
REGION                  1..15
                        note = synthetic construct
MOD_RES                 1
                        note = Glycine is modified with trimesic acid
MOD_RES                 6
                        note = L-2,3-diaminopropionic acid
MOD_RES                 8
                        note = L-2-naphthylalanine
MOD_RES                 10
                        note = D-arginine
MOD_RES                 12
                        note = L-2,3-diaminopropionic acid
MOD_RES                 13..14
                        note = bAla
source                  1..15
                        mol_type = protein
                        organism = synthetic construct
SEQUENCE: 152
GWIYAXAXRR RXXXK                                                              15

SEQ ID NO: 153          moltype = AA   length = 15
FEATURE                 Location/Qualifiers
REGION                  1..15
                        note = synthetic construct
MOD_RES                 1
                        note = Glycine is modified with trimesic acid
MOD_RES                 6
                        note = L-2,3-diaminopropionic acid
MOD_RES                 10
                        note = D-arginine
MOD_RES                 12
                        note = L-2,3-diaminopropionic acid
MOD_RES                 13..14
                        note = bAla
source                  1..15
                        mol_type = protein
                        organism = synthetic construct
SEQUENCE: 153
GWIYAXFARR RXXXK                                                              15

SEQ ID NO: 154          moltype = AA   length = 15
FEATURE                 Location/Qualifiers
REGION                  1..15
                        note = synthetic construct
MOD_RES                 1
                        note = Glycine is modified with trimesic acid
MOD_RES                 6
                        note = L-2,3-diaminopropionic acid
MOD_RES                 8
                        note = L-2-naphthylalanine
MOD_RES                 10
```

```
                        note = D-arginine
MOD_RES                 12
                        note = L-2,3-diaminopropionic acid
MOD_RES                 13..14
                        note = bAla
source                  1..15
                        mol_type = protein
                        organism = synthetic construct
SEQUENCE: 154
GWIYAXFXAR RXXXK                                                             15

SEQ ID NO: 155          moltype = AA  length = 15
FEATURE                 Location/Qualifiers
REGION                  1..15
                        note = synthetic construct
MOD_RES                 1
                        note = Glycine is modified with trimesic acid
MOD_RES                 6
                        note = L-2,3-diaminopropionic acid
MOD_RES                 8
                        note = L-2-naphthylalanine
MOD_RES                 10
                        note = D-alanine
MOD_RES                 12
                        note = L-2,3-diaminopropionic acid
MOD_RES                 13..14
                        note = bAla
source                  1..15
                        mol_type = protein
                        organism = synthetic construct
SEQUENCE: 155
GWIYAXFXRA RXXXK                                                             15

SEQ ID NO: 156          moltype = AA  length = 15
FEATURE                 Location/Qualifiers
REGION                  1..15
                        note = synthetic construct
MOD_RES                 1
                        note = Glycine is modified with trimesic acid
MOD_RES                 6
                        note = L-2,3-diaminopropionic acid
MOD_RES                 8
                        note = L-2-naphthylalanine
MOD_RES                 10
                        note = D-arginine
MOD_RES                 12
                        note = L-2,3-diaminopropionic acid
MOD_RES                 13..14
                        note = bAla
source                  1..15
                        mol_type = protein
                        organism = synthetic construct
SEQUENCE: 156
GWIYAXFXRR AXXXK                                                             15

SEQ ID NO: 157          moltype = AA  length = 15
FEATURE                 Location/Qualifiers
REGION                  1..15
                        note = synthetic construct
MOD_RES                 1
                        note = Glycine is modified with trimesic acid
MOD_RES                 6
                        note = L-2,3-diaminopropionic acid
MOD_RES                 8
                        note = L-2-naphthylalanine
MOD_RES                 10
                        note = D-arginine
MOD_RES                 12
                        note = L-2,3-diaminopropionic acid
MOD_RES                 13..14
                        note = bAla
source                  1..15
                        mol_type = protein
                        organism = synthetic construct
SEQUENCE: 157
GAIAAXFXRR RXXXK                                                             15

SEQ ID NO: 158          moltype = AA  length = 15
FEATURE                 Location/Qualifiers
```

```
REGION          1..15
                note = synthetic construct
MOD_RES         1
                note = Glycine is modified with trimesic acid
MOD_RES         6
                note = L-2,3-diaminopropionic acid
MOD_RES         8
                note = L-2-naphthylalanine
MOD_RES         10
                note = D-arginine
MOD_RES         12
                note = L-2,3-diaminopropionic acid
MOD_RES         13..14
                note = bAla
source          1..15
                mol_type = protein
                organism = synthetic construct
SEQUENCE: 158
GAAAAXFXRR RXXXK                                              15
```